(12) United States Patent
Lam et al.

(10) Patent No.: US 9,000,038 B2
(45) Date of Patent: *Apr. 7, 2015

(54) METHODS AND DEVICES FOR PROVIDING PROLONGED DRUG THERAPY

(71) Applicant: ALZA Corporation, Vacaville, CA (US)

(72) Inventors: Andrew C. Lam, Palo Alto, CA (US); Padmaja Shivanand, Palo Alto, CA (US); Atul D Ayer, Palo Alto, CA (US); Zahedeh Hatamkhany, Palo Alto, CA (US); Richard G Weyers, Palo Alto, CA (US); Suneel K. Gupta, Palo Alto, CA (US); Diane R Guinta, Palo Alto, CA (US); Carol A. Christopher, Palo Alto, CA (US); Samuel R. Saks, Palo Alto, CA (US); Lawrence G. Hamel, Palo Alto, CA (US); Jeri D. Wright, Palo Alto, CA (US)

(73) Assignee: ALZA Corporation, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/800,869

(22) Filed: Mar. 13, 2013

(65) Prior Publication Data

US 2013/0209562 A1    Aug. 15, 2013

Related U.S. Application Data

(60) Division of application No. 10/638,977, filed on Aug. 12, 2003, which is a continuation of application No. 09/802,709, filed on Mar. 8, 2001, now Pat. No. 6,930,129, which is a continuation of application No. 09/253,317, filed on Feb. 19, 1999, now Pat. No. 6,919,373, which is a continuation-in-part of application No. 09/070,666, filed on Apr. 30, 1998, now abandoned, which is a continuation of application No. 08/910,593, filed on Jul. 31, 1997, said application No. 09/253,317 is a continuation-in-part of application No. 08/967,606, filed on Nov. 10, 1997, now abandoned, which is a continuation-in-part of application No. 08/937,336, filed on Aug. 19, 1997, now abandoned.

(60) Provisional application No. 60/044,121, filed on Apr. 22, 1997, provisional application No. 60/030,514, filed on Nov. 12, 1996, provisional application No. 60/031,741, filed on Nov. 25, 1996.

(51) Int. Cl.
| | |
|---|---|
| *A61K 31/235* | (2006.01) |
| *A61K 31/137* | (2006.01) |
| *A61K 9/24* | (2006.01) |
| *A61K 9/20* | (2006.01) |
| *A61K 9/70* | (2006.01) |
| *A61K 31/00* | (2006.01) |
| *A61K 31/4422* | (2006.01) |
| *A61K 31/4458* | (2006.01) |
| *A61K 9/50* | (2006.01) |
| *A61K 9/00* | (2006.01) |
| *A61K 31/421* | (2006.01) |

(52) U.S. Cl.
CPC ............ *A61K 9/2086* (2013.01); *A61K 31/137* (2013.01); *A61K 9/209* (2013.01); *A61K 9/70* (2013.01); *A61K 9/2072* (2013.01); *A61K 31/00* (2013.01); *A61K 31/4422* (2013.01); *A61K 31/4458* (2013.01); *A61K 9/5084* (2013.01); *A61K 9/0004* (2013.01); *A61K 9/0002* (2013.01); *A61K 31/421* (2013.01)

(58) Field of Classification Search
USPC .......................................................... 514/532
See application file for complete search history.

(56) References Cited

U.S. PATENT DOCUMENTS

| | | | |
|---|---|---|---|
| 2,507,631 | A | 5/1950 | Hartmann |
| 2,648,609 | A | 8/1953 | Wurster |
| 2,668,162 | A | 2/1954 | Lowe |
| 2,676,945 | A | 4/1954 | Higgins |
| 2,738,303 | A | 3/1956 | Blythe et al. |
| 2,798,053 | A | 7/1957 | Brown et al. |
| 2,799,241 | A | 7/1957 | Wurster et al. |
| 2,909,462 | A | 10/1959 | Warfield et al. |
| 2,957,880 | A | 10/1960 | Rometsch |
| 2,996,431 | A | 8/1961 | Barry |
| 3,074,852 | A | 1/1963 | Mayron |
| 3,139,383 | A | 6/1964 | Neville, Jr. |

(Continued)

FOREIGN PATENT DOCUMENTS

| | | |
|---|---|---|
| BE | 675 379 A | 5/1966 |
| CA | 1 169 090 A1 | 6/1984 |

(Continued)

OTHER PUBLICATIONS

"Complaint", In the United States District Court for the District of Delaware, Case No. 1:10-cv-00023-LPS, Filed Jan. 8, 2010, 48 pages.

(Continued)

*Primary Examiner* — Zohreh Fay
(74) *Attorney, Agent, or Firm* — Baker & Hostetler LLP

(57) ABSTRACT

Methods and devices for maintaining a desired therapeutic drug effect over a prolonged therapy period are provided. In particular, oral dosage forms that release drug within the gastrointestinal tract at an ascending release rate over an extended time period are provided. The dosage forms may additionally comprise an immediate-release dose of drug.

12 Claims, 2 Drawing Sheets

(56) References Cited

U.S. PATENT DOCUMENTS

| | | |
|---|---|---|
| 3,158,109 A | 11/1964 | Stott |
| 3,400,197 A | 9/1968 | Lippmann et al. |
| 3,625,214 A | 12/1971 | Higuchi |
| 3,634,584 A | 1/1972 | Poole |
| 3,773,919 A | 11/1973 | Boswell et al. |
| 3,811,444 A | 5/1974 | Heller et al. |
| 3,825,068 A | 7/1974 | Norton et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien et al. |
| 4,036,227 A | 7/1977 | Zaffaroni et al. |
| 4,036,228 A | 7/1977 | Theeuwes et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi |
| 4,083,949 A | 4/1978 | Benedikt |
| 4,088,864 A | 5/1978 | Theeuwes et al. |
| 4,093,709 A | 6/1978 | Choi et al. |
| 4,111,201 A | 9/1978 | Theeuwes |
| 4,111,202 A | 9/1978 | Theeuwes et al. |
| 4,137,300 A | 1/1979 | Sheth et al. |
| 4,142,526 A | 3/1979 | Zaffaroni et al. |
| RE30,053 E | 7/1979 | Bundy |
| 4,183,912 A | 1/1980 | Rosenthale |
| 4,200,098 A | 4/1980 | Ayer et al. |
| 4,248,847 A | 2/1981 | Derleth et al. |
| 4,285,987 A | 8/1981 | Ayer et al. |
| 4,290,426 A | 9/1981 | Luschen et al. |
| 4,304,591 A | 12/1981 | Mueller et al. |
| 4,327,725 A | 5/1982 | Cortese et al. |
| 4,434,153 A | 2/1984 | Urquhart et al. |
| 4,449,983 A | 5/1984 | Cortese et al. |
| 4,476,140 A | 10/1984 | Sears et al. |
| 4,519,801 A | 5/1985 | Edgren |
| 4,522,625 A | 6/1985 | Edgren |
| 4,576,604 A | 3/1986 | Guittard et al. |
| 4,591,500 A | 5/1986 | Scapinelli |
| 4,598,094 A | 7/1986 | Wurtman et al. |
| 4,612,008 A | 9/1986 | Wong et al. |
| 4,673,405 A | 6/1987 | Guittard et al. |
| 4,721,613 A | 1/1988 | Urquhart et al. |
| 4,743,247 A | 5/1988 | Wong |
| 4,751,071 A | 6/1988 | Magruder et al. |
| 4,752,470 A | 6/1988 | Mehta |
| 4,783,337 A | 11/1988 | Wong et al. |
| 4,811,549 A | 3/1989 | Usami et al. |
| 4,814,181 A | 3/1989 | Jordan et al. |
| 4,837,111 A | 6/1989 | Deters et al. |
| 4,853,229 A | 8/1989 | Theeuwes |
| 4,855,315 A | 8/1989 | Devlin |
| 4,859,469 A | 8/1989 | Baudier et al. |
| 4,871,549 A | 10/1989 | Ueda et al. |
| 4,874,388 A | 10/1989 | Wong et al. |
| 4,891,230 A | 1/1990 | Geoghegan et al. |
| 4,892,778 A | 1/1990 | Theeuwes et al. |
| 4,915,953 A | 4/1990 | Jordan et al. |
| 4,915,954 A | 4/1990 | Ayer et al. |
| 4,917,899 A | 4/1990 | Geoghegan et al. |
| 4,931,285 A | 6/1990 | Edgren et al. |
| 4,940,465 A | 7/1990 | Theeuwes et al. |
| 4,956,181 A | 9/1990 | Bayer et al. |
| 4,957,494 A | 9/1990 | Wong et al. |
| 5,002,776 A | 3/1991 | Geoghegan et al. |
| 5,017,381 A | 5/1991 | Maruyama et al. |
| 5,023,088 A | 6/1991 | Wong et al. |
| 5,030,456 A | 7/1991 | Ayer et al. |
| 5,051,262 A | 9/1991 | Panoz et al. |
| 5,082,668 A | 1/1992 | Wong et al. |
| 5,089,270 A | 2/1992 | Hampton et al. |
| 5,093,200 A | 3/1992 | Watanabe et al. |
| 5,094,786 A | 3/1992 | Nagashima et al. |
| 5,149,786 A | 9/1992 | Ramirez et al. |
| 5,156,850 A | 10/1992 | Wong et al. |
| 5,178,866 A | 1/1993 | Wright et al. |
| 5,183,807 A | 2/1993 | Della Valle et al. |
| 5,192,550 A | 3/1993 | Edgren et al. |
| 5,232,705 A | 8/1993 | Wong et al. |
| 5,256,850 A | 10/1993 | Maegawa et al. |
| 5,294,770 A | 3/1994 | Riddle et al. |
| 5,326,570 A | 7/1994 | Rudnic et al. |
| 5,399,828 A | 3/1995 | Riddle et al. |
| 5,413,572 A | 5/1995 | Wong et al. |
| 5,422,831 A | 6/1995 | Misra et al. |
| 5,464,631 A | 11/1995 | Hoover et al. |
| 5,474,786 A | 12/1995 | Kotwal et al. |
| 5,484,607 A | 1/1996 | Horacek |
| 5,512,593 A | 4/1996 | Dante |
| 5,558,231 A | 9/1996 | Weier |
| 5,558,879 A | 9/1996 | Chen et al. |
| 5,593,694 A | 1/1997 | Hayashida et al. |
| 5,613,958 A | 3/1997 | Kochinke et al. |
| 5,707,663 A | 1/1998 | Ayer et al. |
| 5,718,700 A | 2/1998 | Edgren et al. |
| 5,770,227 A | 6/1998 | Dong et al. |
| 5,785,994 A | 7/1998 | Wong et al. |
| 5,824,338 A | 10/1998 | Jacobs et al. |
| 5,837,284 A | 11/1998 | Mehta et al. |
| 5,869,097 A | 2/1999 | Wong et al. |
| 5,874,090 A | 2/1999 | Baker et al. |
| 6,919,373 B1 | 7/2005 | Lam et al. |
| 6,930,192 B2 | 8/2005 | Dalko et al. |
| 8,163,798 B2 | 4/2012 | Gupta et al. |

FOREIGN PATENT DOCUMENTS

| | | |
|---|---|---|
| EP | 0 094 123 A2 | 11/1983 |
| EP | 0 212 747 A2 | 3/1987 |
| EP | 0212747 A2 | 3/1987 |
| EP | 0 216 743 A2 | 4/1987 |
| EP | 0 348 808 A2 | 1/1990 |
| EP | 0 381 219 A2 | 8/1990 |
| EP | 0 621 032 A1 | 10/1994 |
| FR | 2 598 319 A1 | 11/1987 |
| FR | 2 620 025 A1 | 3/1989 |
| FR | 2 635 460 B1 | 2/1990 |
| GB | 1 113 860 A | 5/1968 |
| GB | 2 206 046 A | 12/1988 |
| GB | 2 206 047 B | 12/1988 |
| JP | 62-111923 A | 5/1987 |
| JP | 2-237918 A | 9/1990 |
| JP | 44-22517 A | 9/2005 |
| WO | WO 91/03247 A1 | 3/1991 |
| WO | WO 92/01445 A1 | 2/1992 |
| WO | WO 92/04012 A1 | 3/1992 |
| WO | WO 92/18102 A1 | 10/1992 |
| WO | WO 93/05769 A1 | 4/1993 |
| WO | WO 95/19174 A1 | 7/1995 |
| WO | WO 95/20946 A1 | 8/1995 |
| WO | WO 98/06380 A2 | 2/1998 |
| WO | WO 98/14168 A1 | 4/1998 |
| WO | WO 98/23263 A1 | 6/1998 |
| WO | WO 99/62496 A1 | 12/1999 |

OTHER PUBLICATIONS

"Answer, Defense and Counterclaims of Defendants Kremer's Urban, LLC and Kudco Ireland Ltd", In the United States District Court for the District of Delaware, Case No. 1:10-cv-00023-LPS, Filed Mar. 8, 2010, 18 pages.

"Defendants Kremers Urban, LLC and Kudco Ireland Ltd.'s Motion for Leave to File an Amended Answer", In the United States District Court for the District of Delaware, Case No. 1:10-cv-00023-LPS, Filed May 19, 2011, 51 pages.

"Defendants Kremers Urban, LLC and Kudco Ireland, Ltd.'s Opening Brief in Support of Their Motion for Leave to File an Amended Answer", In the United States District Court for the District of Delaware, Case No. 1:10-cv-00023-LPS, Filed May 19, 2011, 24 pages.

"Declaration of Richard L. Horwitz, Esq. in Support of Defendants Kremers Urban, LLC and Kudco Ireland, Ltd's Motion for Leave to File an Amended Answer", In the United States District Court for the

(56) References Cited

OTHER PUBLICATIONS

District of Delaware, Case No. 1:10-cv-00023-LPS, Filed May 19, 2011, 80 pages.
"Defendants Kremers Urban, LLC and Kudco Ireland, Ltd.'s Reply in Support of their Motion for Leave", In the United States District Court for the District of Delaware, Case No. 1:10-cv-00023-LPS, Filed Nov. 19, 2010, 14 pages.
"Declaration of Richard L. Horwitz in Support of Defendants Kremers Urban, LLC and Kudco Ireland, Ltd.'s Motion for Leave", In the United States District Court for the District of Delaware, Case No. 1:10-cv-00023-LPS, Filed Nov. 19, 2010, 28 pages.
"Plaintiffs' First Set of Interrogatories to Defendants' Kremers Urban, LLC and Kudco Ireland, Ltd.(Nos. 1-7)," In the United States District Court for the District of Delaware, Civil Action No. 10-23-LPS, Filed Dec. 1, 2010, 9 pages.
"Defendants Kremers Urban, LLC and Kudco Ireland, Ltd.'s Opposition to Plaintiffs' Motion for Leave to File Sur-Reply", In the United States District Court for the District of Delaware, Case No. 1:10-cv-00023-LPS, Filed Dec. 8, 2010, 5 pages.
"Plaintiffs' Responses and Objections to Defendants Kremers Urban, LLC, and Kudco Ireland, Ltd.'s First Set of Interrogatories (Nos. 1-11)", In the United States District Court for the District of Delaware, Civil Action No. 10-23-LPS, filed Jan. 18, 2011, 36 pages.
"Declaration of Richard L. Horwitz in Support of Defendants Kremers Urban, LLC and Kudco Ireland, Ltd.'s Opening Claim Construction Brief", In the United States District Court for the District of Delaware, Case No. 1:10-cv-00023-LPS, Filed Jan. 21, 2011, 128 pages.
"Plaintiffs ALZA Corporation and Ortho-McNeii-Janssen Pharmaceuticals, Inc.'s Opening Brief on Claim Construction", In the United States District Court for the District of Delaware, Case No. 1:10-cv-00023-LPS, Filed Jan. 21, 2011, 57 pages.
"Plaintiffs ALZA Corporation and Ortho-McNeii-Janssen Pharmaceuticals, Inc.'s Responsive Claim Construction Brief", In the United States District Court for the District of Delaware, Case No. 1:10-cv-00023-LPS, Filed Feb. 4, 2011, 16 pages.
"Defendants Kremers Urban, LLC and Kudco Ireland, Ltd.'s Supplemental Responses to Plaintiffs' Interrogatories (Nos. 1,2, and 6)", In the United States District Court for the District of Delaware, Civil Action No. 10-23-LPS, Filed Feb. 22, 2011, 18 pages.
"Defendants Kremers Urban, LLC and Kudco Ireland, Ltd.'s Revised Supplemental Responses to Plaintiffs' Interrogatories (Nos. 1,2, and 6)", In the United States District Court for the District of Delaware, Civil Action No. 10-23-LPS, Filed Feb. 24, 2011, 18 pages.
"Motion for Summary Judgment of Invalidity", In the United States District Court for the District of Delaware, Case No. 1:10-cv-00023-LPS, Filed Feb. 28, 2011, 3 pages.
"Defendants Kremers Urban, LLC and Kudco Ireland, Ltd.'s Brief in Support of their Motion for Summary Judgment of Invalidity for Lack of Enablement of U.S. Patent No. 6,930,129", In the United States District Court for the District of Delaware, Case No. 1:10-cv-00023-LPS, Filed Feb. 28, 2011, 19 pages.
"Declaration of Richard L. Horwitz in Support of Defendants Kremers Urban LLC and Kudco Ireland, Ltd.'s Motion for Summary Judgment of Invalidity due to Lack of Enablement of U.S. Patent No. 6,930,129", In the United States District Court for the District of Delaware, Case No. 1:10-cv-00023-LPS, Filed Mar. 8, 2011,97 pages.
"Wilmington, Delaware, Thursday Feb. 24, 2011, Claim Construction Hearing", In the United States District Court for the District of Delaware, Case No. 1:10-cv-00023-LPS, Filed Mar. 16, 2011,81 pages.
"Declaration of Peter S. Choi in Support of Plaintiffs' Answering Brief in Opposition to Defendants' Motion for Summary Judgment of Invalidity for Lack of Enablement of U.S. Patent No. 6,930,129", In the United States District Court for the District of Delaware, Case No. 1:10-cv-00023-LPS, Filed Mar. 21, 2011,56 pages.
"Declaration of Diane J. Burgess, Ph.D. in Support of Plaintiffs' Opposition to Defendants' Motion for Summary Judgment of Invalidity for Lack of Enablement U.S. Patent No. 6,930,129", In the United States District Court for the District of Delaware, Case No. 1:10-cv-00023-LPS, Filed Mar. 21, 2011, 79 pages.
"Defendants Kremers Urban, LLC and Kudco Ireland, Ltd.'s Reply in Support of their Motion for Summary Judgment of Invalidity", In the United States District Court for the District of Delaware, Case No. 1:10-cv-00023-LPS, Filed Mar. 28, 2011, 15 pages.
"Exhibit A—U.S. Patent No. 6,919,373 B 1", In the United States District Court for the District of Delaware, Case No. 1:05-cv-00642-JJF, Doc. 1-1, filed Sep. 1, 2005, 17 pages.
"Exhibit B—U.S. Patent No. 6,930,129 B 2", In the United States District Court for the District of Delaware, Case No. 1:05-cv-00642-JJF, Doc. 1-2, filed Sep. 1, 2005, 17 pages.
"Acknowledgment of Receipt for AO Form 85, Notice of Availability of a United States Magistrate Judge to Exercise Jurisdiction", In the United States District Court for the District of Delaware, Case No. 1:05-cv-00642-JJF, Doc. 1-4, filed Sep. 1, 2005, 1 page.
"Answer, Affirmative Defenses and Counterclaims", In the United States District Court for the District of Delaware, Case No. 1:05-cv-00642-JJF, Doc. 7, filed Oct. 25, 2005, 16 pages.
"Reply to Counterclaims", In the United States District Court for the District of Delaware, Case No. 1:05-cv-00642-JJF, Doc. 8, filed Nov. 4, 2005, 4 pages.
"Reply to Counterclaims", In the United States District Court for the District of Delaware, Case No. 1:05-cv-00642-JJF, Doc. 12, filed Dec. 6, 2005, 5 pages.
"Stipulated Order", In the United States District Court for the District of Delaware, Case No. 1:05-cv-00642-JJF, Doc. 75, filed Oct. 3, 2006, 1 page.
"Redacted Public Version First Amended Answer, Affirmative Defenses and Counterclaims", In the United States District Court for the District of Delaware, Case No. 1:05-cv-00642-JJF, Doc. 84, filed Nov. 10, 2006, 26 pages.
"Plaintiffs Alza Corporation and McNeii-PPC, Inc.'s Opening Brief on Claim Construction", In the United States District Court for the District of Delaware, Case No. 1:05-cv-00642-JJF, Doc. 87, filed Nov. 13, 2006, 47 pages.
"Exhibit A—U.S. Patent No. 6,919,373 B 1", In the United States District Court for the District of Delaware, Case No. 1:05-cv-00642-JJF, Doc. 87-1, filed Nov. 13, 2006, 17 pages.
"Exhibit B—U.S. Patent No. 6,930,129 B 2", In the United States District Court for the District of Delaware, Case No. 1:05-cv-00642-JJF, Doc. 87-2, filed Nov. 13, 2006, 17 pages.
"Exhibit D—Letter from Sidley Austin LLP dated Nov. 2, 2006", In the United States District Court for the District of Delaware, Case No. 1:05-cv-00642-JJF, Doc. 87-4, filed Nov. 13, 2006, 3 pages.
"Exhibit E—Letter from Alan B. Clement dated Nov. 2, 2006", In the United States District Court for the District of Delaware, Case No. 1:05-cv-00642-JJF, Doc. 87-5, filed Nov. 13, 2006, 3 pages.
"Exhibit F—Letter from Sidley Austin LLP dated Nov. 3, 2006", In the United States District Court for the District of Delaware, Case No. 1:05-cv-00642-JJF, Doc. 87-6, filed Nov. 13, 2006, 2 pages.
"Exhibit G—Email from Alan B. Clement dated Nov. 8, 2006", In the United States District Court for the District of Delaware, Case No. 1:05-cv-00642-JJF, Doc. 87-7, filed Nov. 13, 2006, 2 pages.
"Exhibit H—Greenhill et al., "A Double-Blind, Placebo-Controlled Study of Modified-Release Methylphenidate in Children With Attention-DefiiUHyperactivity Disorder" Pediatrics, Mar. 2002, vol. 109, No. 3" in the United States District Court for the District of Delaware, Case No. 1:05-cv-00642-JJF, Doc. 87-8, filed Nov. 13, 2006, 10 pages.
Exhibit I—Swanson et al., "Acute Tolerance to Methylphenidate in the Treatment of Attention Deficit Hyperactivity Disorder in Children", Clinical Pharmacology & Therapeutics, 1999, 66(3), In the United States District Court for the District of Delaware, Case No. 1:05-cv-00642-JJF, Doc. 87-9, filed Nov. 13, 2006, 12 pages.
"Exhibit J—U.S. Patent No. 6,124,355", In the United States District Court for the District of Delaware, Case No. 1:05-cv-00642-JJF, Doc. 87-10, filed Nov. 13, 2006,13 pages.
"Exhibit K—Final Judgment, Westlaw", In the United States District Court for the District of Delaware, Case No. 1:05-cv-00642-JJF, Doc. 87-11, filed Nov. 13, 2006, 10 pages.

(56) References Cited

OTHER PUBLICATIONS

Exhibit L—Hanson et al., "Handbook of Dissolution Testing, Third Edition, Revised, Chapter 1 Overall Considerations, copyright 2004", In the United States District Court for the District of Delaware, Case No. 1:05-cv-00642-JJF, Doc. 87-12, filed Nov. 13, 2006, 5 pages.
"Exhibit Q—Applied Biopharmaceutics & Pharmacokinetics Fourth Edition, Chapter 2 Introduction to Biopharmaceutics & Pharmacokinetics, copyright 1999", In the United States District Court for the District of Delaware, Case No. 1:05-cv-00642-JJF, Doc. 87-17, filed Nov. 13, 2006, 8 pages.
Redacted Public Version "Defendants' Opening Markman Brief on Claim Construction", In the United States District Court for the District of Delaware, Case No. 1:05-cv-00642-JJF, Doc. 88, filed Nov. 20, 2006, 44 pages.
"Exhibit A—U.S. Patent No. 6,919,373 81", In the United States District Court for the District of Delaware, Case No. 1:05-cv-00642-JJF, Doc. 88-1, filed Nov. 20, 2006, 17 pages.
"Exhibit B—U.S. Patent No. 6,930,129 82", In the United States District Court for the District of Delaware, Case No. 1:05-cv-00642-JJF, Doc. 88-2, filed Nov. 20, 2006, 17 pages.
"Exhibit C—U.S. Patent Application Publication 2004/0156896 A1", In the United States District Court for the District of Delaware, Case No. 1:05-cv-00642-JJF, Doc. 88-3, filed Nov. 20, 2006, 16 pages.
"Exhibit E—Redacted", In the United States District Court for the District of Delaware, Case No. 1:05-cv-00642-JJF, Doc. 88-5, filed Nov. 20, 2006, 2 pages.
"Exhibit G—Non-Final Office Action, In the United States Patent and Trademark Office, In re U.S. Appl. No. 09/253,317, filed Feb. 19, 1999", In the United States District Court for the District of Delaware, Case No. 1:05-cv-00642-JJF, Doc. 88-7, filed Nov. 20, 2006, 7 pages.
"Exhibit I—Supplemental Declaration of Suneel K. Gupta, In the United States Patent and Trademark Office, In re U.S. Appl. No. 09/253,317, filed Feb. 19, 1999", In the United States District Court for the District of Delaware, Case No. 1:05-cv-00642-JJF, Doc. 88-9, filed Nov. 20, 2006, 5 pages.
"Exhibit J—Redacted", In the United States District Court for the District of Delaware, Case No. 1:05-cv-00642-JJF, Doc. 88-10, filed Nov. 20, 2006, 2 pages.
"Exhibit K—Redacted", In the United States District Court for the District of Delaware, Case No. 1:05-cv-00642-JJF, Doc. 88-11, filed Nov. 20, 2006, 2 pages.
"Exhibit M—Redacted", In the United States District Court for the District of Delaware, Case No. 1:05-cv-00642-JJF, Doc. 88-13, filed Nov. 20, 2006, 2 pages.
"Exhibit N—Redacted", In the United States District Court for the District of Delaware, Case No. 1:05-cv-00642-JJF, Doc. 88-14, filed Nov. 20, 2006, 2 pages.
"Certificate of Service", In the United States District Court for the District of Delaware, Case No. 1:05-cv-00642-JJF, Doc. 88-15, filed Nov. 20, 2006, 2 pages.
Redacted Public Version "Declaration of Umesh V. Banakar, Ph.D. in Support of Opening Markman Brief Submitted by Andrx Pharmaceuticals, LLC and Andrx Corporation", In the United States District Court for the District of Delaware, Case No. 1:05-cv-00642-JJF, Doc. 89, filed Nov. 20, 2006, 29 pages.
"Exhibit A—Curriculum Vitae, Umesh V. Banakar, Ph.D.", In the United States District Court for the District of Delaware, Case No. 1:05-cv-00642-JJF, Doc. 89-1, filed Nov. 20, 2006, 35 pages.
"Exhibit B—U.S. Patent No. 6,919,373 B1", In the United States District Court for the District of Delaware, Case No. 1:05-cv-00642-JJF, Doc. 89-2, filed Nov. 20, 2006, 17 pages.
"Exhibit C—U.S. Patent No. 6,930,129 B2", In the United States District Court for the District of Delaware, Case No. 1:05-cv-00642-JJF, Doc. 89-3, filed Nov. 20, 2006, 17 pages.
"Exhibit E—Final Rejection, In the United States Patent and Trademark Office, in re U.S. Appl. No. 09/253,317, filed Feb. 19, 1999", In the United States District Court for the District of Delaware, Case No. 1:05-cv-00642-JJF, Doc. 89-5, filed Nov. 20, 2006, 5 pages.
"Exhibit F—Non-Final Office Action, In the United States Patent and Trademark Office, In re U.S. Appl. No. 09/253,317, filed Feb. 19, 1999", In the United States District Court for the District of Delaware, Case No. 1:05-cv-00642-JJF, Doc. 89-6, filed Nov. 20, 2006, 6 pages.
"Exhibit G—Declaration of Suneel K. Gupta, In the United States Patent and Trademark Office, In re U.S. Appl. No. 09/253,317, filed Feb. 19, 1999", In the United States District Court for the District of Delaware, Case No. 1:05-cv-00642-JJF, Doc. 89-7, filed Nov. 20, 2006, 5 pages.
"Exhibit H—Supplemental Declaration of Suneel K. Gupta, In the United States Patent and Trademark Office, In re U.S. Appl. No. 09/253,317, filed Feb. 19, 1999", In the United States District Court for the District of Delaware, Case No. 1:05-cv-00642-JJF, Doc. 89-8, filed Nov. 20, 2006, 5 pages.
"Exhibit I—Redacted", In the United States District Court for the District of Delaware, Case No. 1:05-cv-00642-JJF, Doc. 89-9, filed Nov. 20, 2006, 2 pages.
"Exhibit J—Redacted", In the United States District Court for the District of Delaware, Case No. 1:05-cv-00642-JJF, Doc. 89-10, filed Nov. 20, 2006, 2 pages.
"Exhibit K—Redacted", In the United States District Court for the District of Delaware, Case No. 1:05-cv-00642-JJF, Doc. 89-11, filed Nov. 20, 2006, 2 pages.
"Exhibit M—Redacted", In the United States District Court for the District of Delaware, Case No. 1:05-cv-00642-JJF, Doc. 89-13, filed Nov. 20, 2006, 2 pages.
"Reply to First Amended Counterclaims", In the United States District Court for the District of Delaware, Case No. 1:05-cv-00642-JJF, Doc. 90, filed Nov. 22, 2006, 11 pages.
"Letter from Rawle & Henderson LLP dated Nov. 22, 2006", In the United States District Court for the District of Delaware, Case No. 1:05-cv-00642-JJF, Doc. 91, filed Nov. 22, 2006, 1 page.
"To Be Filed Under Seal—Defendants' Opening Markman Brief on Claim Construction", In the United States District Court for the District of Delaware, Case No. 1:05-cv-00642-JJF, Doc. 91-1, filed Nov. 22, 2006, 2 pages.
"Redacted Public Version—Defendants' Opening Markman Brief on Claim Construction", In the United States District Court for the District of Delaware, Case No. 1:05-cv-00642-JJF, Doc. 91-2, filed Nov. 22, 2006, 2 pages.
"Exhibit A—U.S. Patent No. 6,919,373 B 1", In the United States District Court for the District of Delaware, Case No. 1:05-cv-00642-JJF, Doc. 97-1, filed Nov. 30, 2006, 17 pages.
"Exhibit B—U.S. Patent No. 6,930,129 B 2", In the United States District Court for the District of Delaware, Case No. 1:05-cv-00642-JJF, Doc. 97-1, filed Nov. 30, 2006, 17 pages.
"Exhibit C—Curriculum Vitae of Professor Martyn Christopher Davies BSc PhD", In the United States District Court for the District of Delaware, Case No. 1:05-cv-00642-JJF, Doc. 97-2, filed Nov. 30, 2006, 52 pages.
"Exhibit D—U.S. Department of Commerce Patent and Trademark Office Fee Record Sheet, U.S. Appl. No. 08/910,593", In the United States District Court for the District of Delaware, Case No. 1:05-cv-00642-JJF, Doc. 97-3, filed Nov. 30, 2006, 55 pages.
"Exhibit E—U.S. Department of Commerce Patent and Trademark Office Fee Record Sheet, U.S. Appl. No. 60/030,514", In the United States District Court for the District of Delaware, Case No. 1:05-cv-00642-JJF, Doc. 97-4, filed Nov. 30, 2006, 56 pages.
"Exhibit F—Robinson et al., Controlled Drug Delivery Fundamentals and Applications, Second Edition Revised and Expanded, Chapter 9 Design and Fabrication of Oral Controlled Release Drug Delivery Systems", In the United States District Court for the District of Delaware, Case No. 1:05-cv-000642-JJF, Doc. 97-5, filed Nov. 30, 2006, 34 pages.
"Exhibit G—Leong et al., "Polymeric Controlled Drug Delivery", Advanced Drug Delivery Reviews, Sep. 1988, vol. 1, Issue 3", In the United States District Court for the District of Delaware, Case No. 1:05-cv-00642-JJF, Doc. 97-5, filed Nov. 30, 2006, 37 pages.

(56) References Cited

OTHER PUBLICATIONS

"Plaintiffs Alza Corporation and McNeii-PPC, Inc.'s Reply Brief on Claim Construction", In the United States District Court for the District of Delaware, Case No. 1:05-cv-00642-JJF, Doc. 99, filed Dec. 6, 2006, 47 pages.

"U.S. Patent No. 6,930,129 82", In the United States District Court for the District of Delaware, Case No. 1:05-cv-00642-JJF, Doc. 100-1, filed Dec. 6, 2006, 60 pages.

"Declaration of Martin S. Angst, M.D. in support of Reply Markman Brief Submitted by Plaintiffs Alza Corporation and McNeil-PPC", In the United States District Court for the District of Delaware, Case No. 1:05-cv-00642-JJF, Doc. 100-2, filed Dec. 6, 2006, 52 pages.

"Exhibit B—Redacted", In the United States District Court for the District of Delaware, Case No. 1:05-cv-00642-JJF, Doc. 102-2, filed Dec. 7, 2006, 2 pages.

"Exhibit C—Supplemental Declaration of Suneel K. Gupta, In the United States Patent and Trademark Office, In re U.S. Appl. No. 09/253,317, filed Feb. 19, 1999", In the United States District Court for the District of Delaware, Case No. 1:05-cv-00642-JJF, Doc. 102-3, filed Dec. 7, 2006, 5 pages.

"Redacted Public Version Supplemental Declaration of Umesh V. Banakar, PH.D. In Support of Opposition to Plaintiffs' Opening Markman Brief", In the United States District Court for the District of Delaware, Case No. 1:05-cv-00642-JJF, Doc. 103, filed Dec. 7, 2006, 3 pages.

"Exhibit A—Redacted", In the United States District Court for the District of Delaware, Case No. 1:05-cv-00642-JJF, Doc. 103-1, filed Dec. 7, 2006, 2 pages.

"Exhibit B—Redacted", In the United States District Court for the District of Delaware, Case No. 1:05-cv-00642-JJF, Doc. 103-2, filed Dec. 7, 2006, 2 pages.

"Exhibit C—Supplemental Declaration of Suneel K. Gupta, In the United States Patent and Trademark Office, In re U.S. Appl. No. 09/253,317, filed Feb. 19, 1999", In the United States District Court for the District of Delaware, Case No. 1:05-cv-00642-JJF, Doc. 103-3, filed Dec. 7, 2006, 5 pages.

"*Alza Corporation and McNeil, PPC, Inc.* v. *Andrx Pharmaceuticals, LLC and Andrx Corp.*, Hearing, Dec. 15, 2006", In the United States District Court for the District of Delaware, Case No. 1:05-cv-00642-JJF, Doc. 109, 39 pages.

"Plaintiffs Alza Corporation and McNeil-PPC, Inc.'s Motion and Brief in Support to Preclude Testimony of Bruce H. Stoner, Jr.", In the United States District Court for the District of Delaware, Case No. 1:05-cv-00642-JJF, Doc. 123, filed Aug. 20, 2007, 6 pages.

"Expert Report of Bruce H. Stoner, Jr.", In the United States District Court for the District of Delaware, Case No. 1:05-cv-00642-JJF, Doc. 123-1, filed Aug. 20, 2007, 36 pages.

"Exhibit B—Memorandum Opinion, Westlaw.", In the United States District Court for the District of Delaware, Case No. 1:05-cv-00642-JJF, Doc. 123-2, filed Aug. 20, 2007, 36 pages.

"The Patents in Suit", In the United States District Court for the District of Delaware, Case No. 1:05-cv-00642-JJF, Doc. 125-2, filed Aug. 29, 2007, 15 pages.

"Alza Corporation, McNeil-PPC, Inc., Andrx Pharmaceuticals, L.L.C. and Andrx Corporation's Proposed Joint Pre-Trial Order", In the United States District Court for the District of Delaware, Case No. 1:05-cv-00642-JJF, Doc. 128, filed Aug. 31, 2007, 75 pages.

"Order", In the United States District Court for the District of Delaware, Case No. 1:05-cv-00642-JJF, Doc. 130, filed Oct. 5, 2007, 3 pages.

"Letter from Ashby & Geddes dated Dec. 11, 2007", In the United States District Court for the District of Delaware, Case No. 1:05-cv-00642-JJF, Doc. 144, filed Dec. 11, 2007, 1 page.

"Order", In the United States District Court for the District of Delaware, Case No. 1:05-cv-00642-JJF, Doc. 144-1, filed Dec. 11, 2007, 2 pages.

"*Alza Corporation and McNeil, PPC, Inc.* v. *Andrx Pharmaceuticals, LLC and Andrx Corp.* Trial vol. 1, Dec. 10, 2007", In the United States District Court for the District of Delaware, Case No. 1:05-cv-00642-JJF, Doc. 148, 100 pages.

"*Alza Corporation and McNeil, PPC, Inc.* v. *Andrx Pharmaceuticals, LLC and Andrx Corp.* Trial vol. 2, Dec. 11, 2007", In the United States District Court for the District of Delaware, Case No. 1:05-cv-00642-JJF, Doc. 149, 70 pages.

"*Alza Corporation and McNeil, PPC, Inc.* v. *Andrx Pharmaceuticals, LLC and Andrx Corp.* Trial vol. 3, Dec. 12, 2007", In the United States District Court for the District of Delaware, Case No. 1:05-cv-00642-JJF, Doc. 150, 64 pages.

"*Alza Corporation and McNeil, PPC, Inc.* v. *Andrx Pharmaceuticals, LLC and Andrx Corp.* Trial vol. 4, Dec. 13, 2007", In the United States District Court for the District of Delaware, Case No. 1:05-cv-00642-JJF, Doc. 151, 54 pages.

"*Alza Corporation and McNeil, PPC, Inc.* v. *Andrx Pharmaceuticals, LLC and Andrx Corp.* Trial vol. 5, Dec. 14, 2007", In the United States District Court for the District of Delaware, Case No. 1:05-cv-00642-JJF, Doc. 152, 77 pages.

"Letter from Rawle & Henderson LLP dated Dec. 12, 2007", In the United States District Court for the District of Delaware, Case No. 1:05-cv-00642-JJF, Doc. 153, filed Dec. 19, 2007, 5 pages.

"Final Judgment of Non-Infringement", In the United States District Court for the District of Delaware, Case No. 1:05-cv-00642-JJF, Doc. 153-1, filed Dec. 19, 2007, 2 pages.

"Redacted Public Version Defendants' Opening Pretrial Brief With Proposed Findings of Fact and Conclusions of Law", In the United States District Court for the District of Delaware, Case No. 1:05-cv-00642-JJF, Doc. 155, filed Jan. 4, 2008, 66 pages.

"Comparison of claims 1 to 4 and 6 to 7 of the '373 patent with the prior art, Rawle & Henderson LLP, Dec. 3, 2007", In the United States District Court for the District of Delaware, Case No. 1:05-cv-00642-JJF, Doc. 155-2, filed Jan. 4, 2008, 37 pages.

"Redacted Public Version of Exhibits, Defendants' Opening Pretrial Brief With Proposed Findings of Fact and Conclusions of Law", In the United States District Court for the District of Delaware, Case No. 1:05-cv-00642-JJF, Doc. 157, filed Jan. 7, 2008, 1 page.

"Exhibit 1—Prosecution History of Patents-In-Suit", In the United States District Court for the District of Delaware, Case No. 1:05-cv-00642-JJF, Doc. 157-1, filed Jan. 7, 2008, 2 pages.

"Exhibit 2—Background, Westlaw", In the United States District Court for the District of Delaware, Case No. 1:05-cv-00642-JJF, Doc. 157-2, filed Jan. 7, 2008, 10 pages.

"Exhibit 3—Background, Westlaw", In the United States District Court for the District of Delaware, Case No. 1:05-cv-00642-JJF, Doc. 157-3, filed Jan. 7, 2008, 10 pages.

"Exhibit 5—Motions, Pleadings and Filings, Westlaw", In the United States District Court for the District of Delaware, Case No. 1:05-cv-00642-JJF, Doc. 157-5, filed Jan. 7, 2008, 6 pages.

"Redacted Public Version of Exhibits, Defendants' Pretrial Reply Brief", In the United States District Court for the District of Delaware, Case No. 1:05-cv-00642-JJF, Doc. 158, filed Jan. 7, 2008, 1 page.

"Exhibit 6—The Angst 23: The Exemplary 8 Hour Profiles", In the United States District Court for the District of Delaware, Case No. 1:05-cv-00642-JJF, Doc. 158-1, filed Jan. 7, 2008, 2 pages.

"Exhibit 7—Kaufman, "Petitions to FDA Sometimes Delay Generic Drugs", washingtonpost.com, Jul. 3, 2006", In the United States District Court for the District of Delaware, Case No. 1:05-cv-00642-JJF, Doc. 158-2, filed Jan. 7, 2008, 4 pages.

"Exhibit 9—Cycle 1: Gray's Andrx 54 mg Release Rate Evaluation", In the United States District Court for the District of Delaware, Case No. 1:05-cv-00642-JJF, Doc. 158-4, filed Jan. 7, 2008, 8 pages.

"Redacted Public Version, Compendium of Exhibits to Defendants' Pretrial Submissions", In the United States District Court for the District of Delaware, Case No. 1:05-cv-00642-JJF, Doc. 159, filed Jan. 7, 2008, 476 pages.

"Redacted Public Version, Compendium of Exhibits to Defendants' Pretrial Submissions", In the United States District Court for the District of Delaware, Case No. 1:05-cv-00642-JJF, Doc. 160, filed Jan. 7, 2008, 1 page.

"Redacted DTX 73, DTX 106 and DTX 111 Confidential", In the United States District Court for the District of Delaware, Case No. 1:05-cv-00642-JJF, Doc. 160-1, filed Jan. 7, 2008, 16 pages.

(56) References Cited

OTHER PUBLICATIONS

"McNeil Docket No. 2004P-0139: Supplement Comments on Hellerehrman Response", In the United States District Court for the District of Delaware, Case No. 1:05-cv-00642-JJF, Doc. 160-2, filed Jan. 7, 2008, 16 pages.

"U.S. Department of Commerce Patent and Trademark Office, U.S. Appl. No. 60/030,514, File History in File Folder", In the United States District Court for the District of Delaware, Case No. 1:05-cv-00642-JJF, Doc. 160-4, filed Jan. 7, 2008, 54 pages.

"Clinical Pharmacology & Therapeutics, Feb. 1991, vol. 49, No. 2", In the United States District Court for the District of Delaware, Case No. 1:05-cv-00642-JJF, Doc. 160-5, filed Jan. 7, 2008, 3 pages.

"U.S. Department of Commerce Patent and Trademark Office Fee Record Sheet, U.S. Appl. No. 08/937,336", In the United States District Court for the District of Delaware, Case No. 1:05-cv-00642-JJF, Doc. 160-6, filed Jan. 7, 2008, 124 pages.

"Notice of Abandonment, U.S. Department of Commerce Patent and Trademark Office, in Re U.S. Appl. No. 08/937,336, filed Aug. 19, 1997", In the United States District Court for the District of Delaware, Case No. 1:05-cv-00642-JJF, Doc. 160-7, filed Jan. 7, 2008, 6 pages.

"Redacted DTX 176, DTX 232 and DTX 234 Confidential", In the United States District Court for the District of Delaware, Case No. 1:05-cv-00642-JJF, Doc. 160-9, filed Jan. 7, 2008, 1 page.

"Redacted DTX 176, DTX 232 and DTX 234 Confidential", In the United States District Court for the District of Delaware, Case No. 1:05-cv-00642-JJF, Doc. 160-10, filed Jan. 7, 2008, 1 page.

"Redacted DTX 176, DTX 232 and DTX 234 Confidential", In the United States District Court for the District of Delaware, Case No. 1:05-cv-00642-JJF, Doc. 160-11, filed Jan. 7, 2008, 1 page.

"Redacted DTX 324, DTX 361, DTX 371 and DTX 383 Confidential", In the United States District Court for the District of Delaware, Case No. 1:05-cv-00642-JJF, Doc. 160-13, filed Jan. 7, 2008, 1 page.

"Redacted DTX 324, DTX 361, DTX 371 and DTX 383 Confidential", In the United States District Court for the District of Delaware, Case No. 1:05-cv-00642-JJF, Doc. 160-14, filed Jan. 7, 2008, 1 page.

"Redacted DTX 324, DTX 361, DTX 371 and DTX 383 Confidential", In the United States District Court for the District of Delaware, Case No. 1:05-cv-00642-JJF, Doc. 160-15, filed Jan. 7, 2008, 1 page.

"Redacted DTX 324, DTX 361, DTX 371 and DTX 383 Confidential", In the United States District Court for the District of Delaware, Case No. 1:05-cv-00642-JJF, Doc. 160-16, filed Jan. 7, 2008, 1 page.

"Curriculum Vitae, Umesh V. Banakar, Ph.D.", In the United States District Court for the District of Delaware, Case No. 1:05-cv-00642-JJF, Doc. 160-17, filed Jan. 7, 2008, 34 pages.

"Redacted Public Version, Compendium of Exhibits to Defendants' Pretrial Submissions", In the United States District Court for the District of Delaware, Case No. 1:05-cv-00642-JJF, Doc. 161, filed Jan. 7, 2008, 253 pages.

"Redacted Public Version, Compendium of Exhibits to Defendants' Pretrial Submissions", In the United States District Court for the District of Delaware, Case No. 1:05-cv-00642-JJF, Doc. 162, filed Jan. 7, 2008, 1 page.

"Curriculam Vitae, Sanford M. Bolton, Ph.D.", In the United States District Court for the District of Delaware, Case No. 1:05-cv-00642-JJF, Doc. 162-4, filed Jan. 7, 2008, 17 pages.

"DTX 703", In the United States District Court for the District of Delaware, Case No. 1:05-cv-00642-JJF, Doc. 162-8, filed Jan. 7, 2008, 4 pages.

"Klein et al., "Development of Dissolution Tests on the Basis of Gastrointestinal Physiology", Pharmaceutical Dissolution Testing, copyright 2003, DTX 716", In the United States District Court for the District of Delaware, Case No. 1:05-cv-00642-JJF, Doc. 162-169, filed Jan. 7, 2008, 6 pages.

"USP 23 The United States Pharmacopeia NF 18 The National Formulary, 1995, Jan. 1, 1995, DTX 720", In the United States District Court for the District of Delaware, Case No. 1:05-cv-00642-JJF, Doc. 162-10, filed Jan. 7, 2008, 4 pages.

"Markowitz et al., "Pharmacokinetic and Pharmacodynamic Drug Interactions, Methylphenidate, Amphetamine, or Atomoxetine in ADHD", Attention Deficit Hyperactivity Disorder From Genes to Patients, DTX 930", In the United States District Court for the District of Delaware, Case No. 1:05-cv-00642-JJF, Doc. 162-11, filed Jan. 7, 2008, 13 pages.

"Klein et al., "Development of Dissolution Tests on the Basis of Gastrointestinal Physiology", Pharmaceutical Dissolution Testing, copyright 2003, DTX 1064", In the United States District Court for the District of Delaware, Case No. 1:05-cv-00642-JJF, Doc. 162-12, filed Jan. 7, 2008, 6 pages.

"Abrahamsson et al., "Biopharmaceutical Support in Formulation Development", Pharmaceutical Preformulation and Formulation, copyright 2000, DTX 1065", In the United States District Court for the District of Delaware, Case No. 1:05-cv-00642-JJF, Doc. 162-13, filed Jan. 7, 2008, 4 pages.

"FIP Guidelines for Dissolution Testing of Solid Oral Products, DTX 1067", In the United States District Court for the District of Delaware, Case No. 1:05-cv-00642-JJF, Doc. 162-14, filed Jan. 7, 2008, 14 pages.

"Redacted Public Version, Compendium of Exhibits to Defendants' Pretrial Submissions", In the United States District Court for the District of Delaware, Case No. 1:05-cv-00642-JJF, Doc. 163, filed Jan. 7, 2008, 1 page.

"U.S. Patent No. 6,919,373", In the United States District Court for the District of Delaware, Case No. 1:05-cv-00642-JJF, Doc. 163-1, filed Jan. 7, 2008, 17 pages.

"Pelham et al., "Relative Efficacy of Long-Acting Stimulants on Children With Attention Deficit-Hyperactivity Disorder: A Comparison of Standard Methylphenidate, Sustained-Release Methylphenidate, Sustained-Release Dextroamphetamine, and Pemoline", Pediatrics, Aug. 1990, vol. 86, No. 2", In the United States District Court For the District of Delaware, Case No. 1:05-cv-00642-JJF, Doc. 163-3, filed Jan. 7, 2008, 12 pages.

"Redacted PX 207 and PX 210 Confidential", In the United States District Court for the District of Delaware, Case No. 1:05-cv-00642-JJF, Doc. 163-4, filed Jan. 7, 2008, 1 page.

"Redacted PX 207 and PX 210 Confidential", In the United States District Court for the District of Delaware, Case No. 1:05-cv-00642-JJF, Doc. 163-5, filed Jan. 7, 2008, 1 page.

"Office Communication—Background of the invention, In the United States Patent and Trademark Office, in re U.S. Appl. No. 10/726,024, filed Dec. 12, 2003", In the United States District Court for the District of Delaware, Case No. 1:05-cv00642-JJF, Doc. 163-7, filed Jan. 7, 2008, 3 pages.

"Redacted Public Version, Plaintiffs' Responsive Pretrial Submission", In the United States District Court for the District of Delaware, Case No. 1:05-cv-00642-JJF, Doc. 165, filed Jan. 8, 2008, 273 pages.

"Letter from Rawle & Henderson LLP dated Jan. 30, 2008", In the United States District Court for the District of Delaware, Case No. 1:05-cv-00642-JJF, Doc. 169, filed Jan. 31, 2008, 1 page.

"Exhibit 1—Redacted" In the United States District Court for the District of Delaware, Case No. 1:05-cv-00642-JJF, Doc. 170-1, filed Feb. 6, 2008, 2 pages.

"Exhibit 4—Email from Todd Wagner dated Dec. 7, 2007" in the United States District Court for the District of Delaware, Case No. 1:05-cv-00642-JJF, Doc. 170-4, filed Feb. 6, 2008, 2 pages.

"Order" In the United States District Court for the District of Delaware, Case No. 1:05-cv-00642-JJF, Doc. 171, filed Feb. 6, 2008, 1 page.

"Letter from Rawle & Henderson LLP dated Apr. 2, 2008" in the United States District Court for the District of Delaware, Case No. 1:05-cv-00642-JJF, Doc. 172, filed Apr. 2, 2008, 2 pages.

"Decision", In the United States Court of Appeals for the Federal Circuit, In re 2007-1404 *Caraco Pharmaceutical Laboratories, Ltd.,* v *Forest Laboratories, Inc., Forest Laboratories Holdings, Ltd., and H. Lundbeck NS*, In the United States District Court for The District of Delaware, Case No. 1:05-cv-00642-JJF, Doc. 172-2, filed Apr. 2, 2008, 37 pages.

"Letter from Ashby & Geddes dated Apr. 15, 2008" in the United States District Court for the District of Delaware, Case No. 1:05-cv-00642-JJF, Doc. 173, filed Apr. 15, 2008, 3 pages.

"Confidential: Filed Under Seal, Stipulated Order" in the United States District Court for the District of Delaware, Case No. 1:05-cv-00642-JJF, Doc. 176, filed May 12, 2008, 88 pages.

(56) References Cited

OTHER PUBLICATIONS

"Defendants' Proposed Findings of Fact and Conclusions of Law, pp. 123-241" in the United States District Court for the District of Delaware, Case No. 1:05-cv-00642-JJF, Doc. 184-1, filed Jun. 24, 2008, 121 pages.
"Email from Rawle & Henderson LLP dated Jul. 2, 2008" in the United States District Court for the District of Delaware, Case No. 1:05-cv-00642-JJF, Doc. 186, filed Jul. 8, 2008, 2 pages.
"Exhibit A—Transcription of Court Hearing, Friday, Dec. 14, 2007, Courtroom 48" in the United States District Court for the District of Delaware, Case No. 1:05-cv-00642-JJF, Doc. 188-1, filed Jul. 9, 2008, 160 pages.
"Notice of Contingent Motion" in the United States District Court for the District of Delaware, Case No. 1:05-cv-00642-JJF, Doc. 190-1, filed Aug. 4, 2008, 2 pages.
"Highly Confidential: Filed Under Seal, Defendants' Memorandum in Opposition to Plaintiffs' Motion to Strike Portions of Defendants' Post-Trial Findings of Fact and in Support of Their Contingent Cross-Motion to Strike Portions of Plaintiffs' Post-Trial Findings of Fact and Conclusions of Law" in the United States District Court for the District of Delaware, Case No. 1:05-cv-00642-JJF, Doc. 190-2, filed Aug. 4, 2008, 18 pages.
"Certificate of Service" in the United States District Court for the District of Delaware, Case No. 1:05-cv-00642-JJF, Doc. 190-3, filed Aug. 4, 2008, 2 pages.
"Exhibit A—Email from Ann M. Mace dated Nov. 30, 2007" in the United States District Court for the District of Delaware, Case No. 1:05-cv-00642-JJF, Doc. 190-4, filed Aug. 4, 2008, 2 pages.
"Exhibit C—Redacted" in the United States District Court for the District of Delaware, Case No. 1:05-cv-00642-JJF, Doc. 190-6, filed Aug. 4, 2008, 2 pages.
"Exhibit D—Redacted" in the United States District Court for the District of Delaware, Case No. 1:05-cv-00642-JJF, Doc. 190-7, filed Aug. 4, 2008, 2 pages.
"Defendants' Reply Memorandum in Support of Their Contingent Cross-Motion to Strike Portions of Plaintiffs Post-Trial Findings of Fact and Conclusions of Law" in the United States District Court for the District of Delaware, Case No. 1:05-cv-00642-JJF, Doc. 192, filed Aug. 15, 2008, 8 pages.
"Exhibit F—Defendants' Proposed Supplemental Findings of Fact and Conclusions of Law Regarding the '129 Patent" in the United States District Court for the District of Delaware, Case No. 1:05-cv-00642-JJF, Doc. 192-1, filed Aug. 15, 2008, 8 pages.
"Certificate of Service" in the United States District Court for the District of Delaware, Case No. 1:05-cv-00642-JJF, Doc. 192-2, filed Aug. 15, 2008, 2 pages.
"Letter from Ashby & Geddes dated Dec. 13, 2007" in the United States District Court for the District of Delaware, Case No. 1:05-cv-00642-JJF, Doc. 193, filed Dec. 5, 2008, 4 pages.
"Order" in the United States District Court for the District of Delaware, Case No. 1:05-cv-00642-JJF, Doc. 195, filed Mar. 30, 2009, 2 pages.
"Final Judgment Order" in the United States District Court for the District of Delaware, Case No. 1:05-cv-00642-JJF, Doc. 204, filed May 6, 2009, 3 pages.
"Federal Circuit Opinion", In the United States Court of Appeals for the Federal Circuit, In re 2009-1350, *Alza Corporation and McNeil-PPC, Inc.,* v *Andrx Pharmaceuticals, LLC and Andrx Corporation* in the United States District Court for the District of Delaware, Case No. 1:05-cv-00642-JJF, Doc. 209-1, filed Jun. 4, 2010, 15 pages.
"Exhibit A—U.S. Patent No. 6,919,373 81" in the United States District Court for the District of Delaware, Case No. 1:05-cv-00642-JJF, Doc. 1-1, filed Jan. 8, 2010, 17 pages.
"Exhibit B—U.S. Patent No. 6,930,129 82" in the United States District Court for the District of Delaware, Case No. 1:05-cv-00642-JJF, Doc. 1-2, filed Jan. 8, 2010, 17 pages.
"Civil Cover Sheet" in the United States District Court for the District of Delaware, Case No. 1:05-cv-00642-JJF, Doc. 1-3, filed Jan. 8, 2010, 1 page.

Reply to Counterclaims in the United States District Court for the District of Delaware, Case No. 1:05-cv-00642-JJF, Doc. 13, filed Mar. 31, 2010, 4 pages.
"Defendants' Kremers Urban, LLC and Kudco Ireland, Ltd.'s Motion for Leave to File Their Motion for Summary Judgment of Invalidity for Lack of Enablement of U.S. Patent Nos. 6,919,373 and 6,930,129" in the United States District Court for the District of Delaware, Case No. 1:05-cv-00642-JJF, Doc. 33, filed Oct. 20, 2010, 4 pages.
Patrick et al., "The Absorption of Sustained-Release Methylphenidate Formulations Compared to an Immediate-Release Formulation," Biopharmaceutics & Drug Disposition, 1989, 10, 165-171.
In the United States District Court for the stated of Delaware, *Alza Corporation and McNeil-PPC, Inc.* vs. *Andrx Pharmaceuticals, LLC, and Andrx Corporation*, Order, Filed Mar. 30, 2009, 2 pages.
In the United States District Court for the stated of Delaware, *Alza Corporation and McNeil-PPC, Inc.* vs. *Andrx Pharmaceuticals, LLC, and Andrx Corporation*, Opinion, Filed Mar. 30, 2009, 106 pages.
"[Proposed] Order" in the United States District Court for the District of Delaware, Case No. 1:05-cv-00642-JJF, Doc. 33-3, filed Oct. 20, 2010, 1 page.
"Acknowledgment of Receipt for AO Form 85, Notice, Consent, and Reference of a Civil Case to a Magistrate Judge and AO Form 85A, Notice, Consent, and Reference of a Dispositive Motion to a Magistrate Judge" in the United States District Court for the District of Delaware, Case No. 1:05-cv-00642-JJF, Doc. 1-4, filed Jan. 8, 2010, 1 page.
"Answer, Defenses and Counterclaims of Defendants' Kremers Urban, LLC, and Kudco Ireland, Ltd." In the United States District Court for the District of Delaware, Case No. 1:05-cv-00642-JJF, Doc. 9, filed Mar. 8, 2010, 18 pages.
"Breadth of Claims", In the United States District Court for the District of Delaware, Case No. 1:05-cv-00642-JJF, Doc. 155-1, filed Jan. 4, 2008, 56 pages.
"Certificate of Service" in the United States District Court for the District of Delaware, Case No. 1:05-cv-00642-JJF, Doc. 170-5, filed Feb. 6, 2008, 2 pages.
"Certificate of Service", In the United States District Court for the District of Delaware, Case No. 1:05-cv-00642-JJF, Doc. 89-14, filed Nov. 20, 2006, 2 pages.
"Certificate of Service", In the United States District Court for the District of Delaware, Case No. 1:05-cv-00642-JJF, Doc. 84-1, filed Nov. 10, 2006, 2 pages.
"Certificate of Service", In the United States District Court for the District of Delaware, Case No. 1:05-cv-00642-JJF, Doc. 102-4, filed Dec. 7, 2006, 2 pages.
"Certificate of Service", In the United States District Court for the District of Delaware, Case No. 1:05-cv-00642-JJF, Doc. 103-4, filed Dec. 7, 2006, 2 pages.
"Certificate of Service", In the United States District Court for the District of Delaware, Case No. 1:05-cv-00642-JJF, Doc. 125-3, filed Aug. 29, 2007, 2 pages.
"Civil Cover Sheer", In the United States District Court for the District of Delaware, Case No. 1:05-cv-00642-JJF, Doc. 1-3, filed Sep. 1, 2005, 2 pages.
"Complaint" in the United States District Court for the District of Delaware, Case No. 1:05-cv-00642-JJF, Doc. 1, filed Jan. 8, 2010, 12 pages.
"Complaint", In the United States District Court for the District of Delaware, Case No. 1:05-cv-00642-JJF, Doc. 1, filed Sep. 1, 2005, 15 pages.
"Contingent Motion" in the United States District Court for the District of Delaware, Case No. 1:05-cv-00642-JJF, Doc. 190, filed Aug. 4, 2008, 1 page.
"Continuation of Transcription of Court Hearing, Friday, Dec. 14, 2007, Courtroom 48" in the United States District Court for the District of Delaware, Case No. 1:05-cv-00642-JJF, Doc. 188-2, filed Jul. 9, 2008, 163 pages.
"Declaration of Martyn C. Davies, Ph.D. In Support of Reply Markman Brief Submitted by Alza Corp. and McNeii-PPC, Inc.", In the

(56) References Cited

OTHER PUBLICATIONS

United States District Court for the District of Delaware, Case No. 1:05-cv-00642-JJF, Doc. 97, filed Nov. 30, 2006, 2 pages.
"Declaration of Vivian A. Gray in Support of Reply Markman Brief Submitted by Plaintiffs Alza Corporation and McNeil-PPC", In the United States District Court for the District of Delaware, Case No. 1:05-cv-00642-JJF, Doc. 101, filed Dec. 6, 2006, 69 pages.
"Defendants' Memorandum in Opposition to Plaintiffs' Motion in Limine to Preclude the Entire Testimony of Bruce H. Stoner, Jr.", In the United States District Court for the District of Delaware, Case No. 1:05-cv-00642-JJF, Doc. 125, filed Aug. 29, 2007, 5 pages.
"Defendants Kremers Urban, LLC and Kudco Ireland, Ltd.'s Opening Claim Construction Brief", In the United States District Court for the District of Delaware, Case No. 1:10-cv-00023-LPS, Filed Jan. 21, 2011, 19 pages.
"Defendants Kremers Urban, LLC and Kudco Ireland, Ltd.'s Response to Plaintiffs' First Set of Interrogatories (Nos. 1-7)", In the United States District Court for the District of Delaware, Civil Action No. 10-23-LPS, Filed Jan. 14, 2011, 14 pages.
"Defendants Kremers Urban, LLC and Kudco Ireland, Ltd.'s Response to Plaintiffs' Opening Claim Construction Brief", in the United States District Court for the District of Delaware, Case No. 1:10-cv-00023-LPS, Filed Feb. 4, 2011, 11 pages.
"Defendants Kremes Urban, LLC and Kudco Ireland, Ltd.'s Motion for Leave to File their Motion for Summary Judgment of Invalidity for Lack of Enablement of U.S. Patent Nos. 6,919,373 and 6,930,129", In the United States District Court for the District of Delaware, Case No. 1:10-cv-00023-LPS, Filed Oct. 20, 2010, 150 pages.
"DTX 143", In the United States District Court for the District of Delaware, Case No. 1:05-cv-00642-JJF, Doc. 160-3, filed Jan. 7, 2008, 1 page.
"DTX 277", In the United States District Court for the District of Delaware, Case No. 1:05-cv-00642-JJF, Doc. 160-12, filed Jan. 7, 2008, 1 page.
"DTX 701", In the United States District Court for the District of Delaware, Case No. 1:05-cv-00642-JJF, Doc. 162-7, filed Jan. 7, 2008, 1 page.
"Exhibit 0—Hubbard et al., "Enantioselective Aspects of the Disposition of dl-threo-Methylphenidate after the Administration of a Sustained-Release Formulation to Children with Attention Deficit-Hyperactivity Disorder", Journal of Pharmaceutical Sciences, Nov. 1989, vol. 78, No. 11", In the United States District Court for the District of Delaware, Case No. 1:05-cv-00642-JJF, Doc. 87-15, filed Nov. 13, 2006, 5 pages.
"Exhibit 2—Pages From Dr. Feifel's Deposition Transcript Cited in Defendants' Pretrial Submissions" in the United States District Court for the District of Delaware, Case No. 1:05-cv-00642-JJF, Doc. 170-2, filed Feb. 6, 2008, 2 pages.
"Exhibit 4—United States Court of Appeals for the Federal Circuit, In Re 2007-1093,-1134, *Pharmaceutical Resources, Inc. and Par Pharmaceuticals, Inc.* v *Roxane Laboratories, Inc.*, Decision, dated Oct. 26, 2007", In the United States District Court for the District of Delaware, Case No. 1:05-cv-00642-JJF, Doc. 157-4, filed Jan. 7, 2008, 11 pages.
"Exhibit B—IR Overcoat Study (Tested Every 15 min)", In the United States District Court for the District of Delaware, Case No. 1:05-cv-00642-JJF, Doc. 158-3, filed Jan. 7, 2008, 2 pages.
"Exhibit A—Motion for Summary Judgment of Invalidity" in the United States District Court for the District of Delaware, Case No. 1:05-cv-00642-JJF, Doc. 33-1, filed Oct. 20, 2010, 64 pages.
"Exhibit A—Redacted", In the United States District Court for the District of Delaware, Case No. 1:05-cv-00642-JJF, Doc. 102-1, filed Dec. 7, 2006, 2 pages.
"Exhibit B—Redacted" in the United States District Court for the District of Delaware, Case No. 1:05-cv-00642-JJF, Doc. 190-5, filed Aug. 4, 2008, 2 pages.
"Exhibit C—Briefs and Other Related Documents, Westlaw", In the United States District Court for the District of Delaware, Case No. 1:05-cv-00642-JJF, Doc. 87-3, filed Nov. 13, 2006, 23 pages.
"Exhibit C—Discussion, Westlaw", In the United States District Court for the District of Delaware, Case No. 1:05-cv-00642-JJF, Doc. 123-3, filed Aug. 20, 2007, 4 pages.
"Exhibit D—Physicians Desk Reference 591 Edition, 2005", In the United States District Court for the District of Delaware, Case No. 1:05-cv-00642-JJF, Doc. 89-4, filed Nov. 20, 2006, 6 pages.
"Exhibit D—Redacted", In the United States District Court for the District of Delaware, Case No. 1:05-cv-00642-JJF, Doc. 88-4, filed Nov. 20, 2006, 2 pages.
"Exhibit E—Redacted" in the United States District Court for the District of Delaware, Case No. 1:05-cv-00642-JJF, Doc. 190-8, filed Aug. 4, 2008, 2 pages.
"Exhibit F—Final Rejection, In the United States Patent and Trademark Office, in re U.S. Appl. No. 09/253,317, filed Feb. 19, 1999", In the United States District Court for the District of Delaware, Case No. 1:05-cv-00642-JJF, Doc. 88-6, filed Nov. 20, 2006, 5 pages.
"Exhibit H—Declaration of Suneel K. Gupta, In the United States Patent and Trademark Office, In re U.S. Appl. No. 09/253,317, filed Feb. 19, 1999",In the United States District Court for the District of Delaware, Case No. 1:05-cv-00642-JJF, Doc. 88-8, filed Nov. 20, 2006, 5 pages.
"Exhibit L—Redacted", In the United States District Court for the District of Delaware, Case No. 1:05-cv-00642-JJF, Doc. 89-12, filed Nov. 20, 2006, 2 pages.
"Exhibit L—USP 25 the United States Pharmacopeia NF 20 the National Formulary, 2002, Jan. 1, 2002", In the United States District Court for the District of Delaware, Case No. 1:05-cv-00642-JJF, Doc. 88-12, filed Nov. 20, 2006, 14 pages.
"Exhibit M—"Guidance for Industry Extended Release Oral Dosage Forms: Development, Evaluation, and Application of in Vitro/in Vivo Correlations", U.S. Department of Health and Human Services Food and Drug Administration Center for Drug Evaluation and Research (COER), Sep. 1997, BP 2" in the United States District Court for the District of Delaware, Case No. 1:05-cv-00642-JJF, Doc. 87-13, filed Nov. 13, 2006, 28 pages.
"Exhibit N—Non-Final Office Action, In the United States Patent and Trademark Office, In re U.S. Appl. No. 09/802,709, filed Mar. 8, 2001", In the United States District Court for the District of Delaware, Case No. 1:05-cv-00642-JJF, Doc. 87-14, filed Nov. 13, 2006, 7 pages.
"Exhibit P—Reply Pursuant to 37 CFR § 1.111, In the United States Patent and Trademark Office, In re U.S. Appl. No. 09/802,709, filed Mar. 8, 2001", In the United States District Court for the District of Delaware, Case No. 1:05-cv-00642-JJF, Doc. 87-16, filed Nov. 13, 2006, 11 pages.
"Judgment", In the United States Court of Appeals for the Federal Circuit, In re 2009-1350, *Alza Corporation and McNeil-PPC, Inc.,* v *Andrx Pharmaceuticals, LLC and Andrx Corporation*in the United States District Court for the District of Delaware, Case No. 1:05-cv-00642-JJF, Doc. 209, filed Jun. 4, 2010, 1 page.
"Laboratory Notebook BW 0392", In the United States District Court for the District of Delaware, Case No. 1:05-cv-00642-JJF, Doc. 160-8, filed Jan. 7, 2008, 5 pages.
"Impax Laboratories, Inc.'s Answer and Counterclaims", In the United States District Court for the District of Delaware, Case No. 1:05-cv-00642-JJF, Doc. 9, filed Nov. 16, 2005, 16 pages.
"Memorandum Order" in the United States District Court for the District of Delaware, Case No. 1:05-cv-00642-JJF, Doc. 174, filed Apr. 28, 2008, 4 pages.
"Opinion" in the United States District Court for the District of Delaware, Case No. 1:05-cv-00642-JJF, Doc. 194, filed Mar. 30, 2009, 106 pages.
"Plaintiffs' Answering Brief in Opposition to Defendants' Motion for Summary Judgment of Invalidity for Lack of Enablement of U.S. Patent No. 6,930,129", In the United States District Court for the District of Delaware, Case No. 1:10-cv-00023-LPS, Filed Mar. 21, 2011, 25 pages.
"Plaintiffs' Combined Reply Memorandum in Further Support of Their Motion to Strike Portions of Defendants' Post-Trial Findings of Fact, and Answering Memorandum in Response to Defendants' Contingent Motion" in the United States District Court for the District of Delaware, Case No. 1:05-cv-00642-JJF, Doc. 1901, filed Aug. 7, 2008,7 pages.

(56) References Cited

OTHER PUBLICATIONS

"Plaintiffs' Motion for Leave to File Sur-Reply in Opposition to Defendants' Motion for Leave to File Motion for Summary Judgment of Invalidity for Lack of Enablement of U.S. Patent Nos. 6,919,373 and 6,390,129", In the United States District Court for the District of Delaware, Case No. 1:10-cv-00023-LPS, Filed Nov. 24, 2010, 27 pages.
"Plaintiffs' Motion to Strike Portions of Defendants' Post-Trial Findings of Fact" In the United States District Court for the District of Delaware, Case No. 1:05-cv-00642-JJF, Doc. 188, filed Jul. 9, 2008, 8 pages.
"Plaintiffs' Opposition to Defendants' Motion for Leave to File Motion for Summary Judgment of Invalidity for Lack of Enablement of U.S. Patent Nos. 6,919,373 and 6,930,129", In the United States District Court for the District of Delaware, Case No. 1:10-cv-00023-LPS, Filed Nov. 12, 2010, 57 pages.
"Plaintiffs' Reply Brief in Support of Plaintiffs' Motion for Leave to File Sur-Reply in Opposition to Defendants' Motion for Leave to File Motion for Summary Judgment of Invalidity for Lack of Enablement of U.S. Patent Nos. 6,919,373 and 6,930,129", In the United States District Court for the District of Delaware, Case No. 1:10-cv-00023-LPS, Filed Dec. 14, 2010, 3 pages.
"Plaintiffs' Supplemental and Amended Responses to Defendants' Interrogatory Nos. 7 and 8", In the United States District Court for the District of Delaware, Civil Action No. 10-23-LPS, Filed Mar. 1, 2011, 7 pages.
"Plaintiffs' Sur-Reply in Opposition to Defendants' Motion for Leave to File Motion for Summary Judgment of Invalidity for Lack of Enablement of U.S. Patent Nos. 6,919,373 and 6,930,129", In the United States District Court for the District of Delaware, Case No. 1:10-cv-00023-LPS, Filed Jan. 5, 2011, 5 pages.
"Prosecution History of Patents-In-Suit", In the United States District Court for the District of Delaware, Case No. 1:05-cv-00642-JJF, Doc. 125-1, filed Aug. 29, 2007, 1 page.
"Redacted DTX 1136 Confidential", In the United States District Court for the District of Delaware, Case No. 1:05-cv-00642-JJF, Doc. 162-15, filed Jan. 7, 2008, 1 page.
"Redacted DTX 661 and DTX 663-672 Confidential", In the United States District Court for the District of Delaware, Case No. 1:05-cv-00642-JJF, Doc. 162-1, filed Jan. 7, 2008, 1 page.
"Redacted DTX 661 and DTX 663-672 Confidential", In the United States District Court for the District of Delaware, Case No. 1:05-cv-00642-JJF, Doc. 162-2, filed Jan. 7, 2008, 1 page.
"Redacted DTX 661 and DTX 663-672 Confidential", In the United States District Court for the District of Delaware, Case No. 1:05-cv-00642-JJF, Doc. 162-3, filed Jan. 7, 2008, 1 page.
"Redacted DTX 699 and DTX 700 Confidential", In the United States District Court for the District of Delaware, Case No. 1:05-cv-00642-JJF, Doc. 162-5, filed Jan. 7, 2008, 1 page.
"Redacted DTX 699 and DTX 700 Confidential", In the United States District Court for the District of Delaware, Case No. 1:05-cv-00642-JJF, Doc. 162-6, filed Jan. 7, 2008, 1 page.
"Redacted Public Version Defendants' Opposition to Plaintiffs' Markman Brief on Claim Construction", In the United States District Court for the District of Delaware, Case No. 1:05-cv-00642-JJF, Doc. 102, filed Dec. 7, 2006, 34 pages.
"Redacted Public Version Defendants' Pretrial Reply Brief", In the United States District Court for the District of Delaware, Case No. 1:05-cv-00642-JJF, Doc. 156, filed Jan. 4, 2008, 60 pages.
"Redacted Public Version, Defendants' Answering Post-Trial Brief Concerning Plaintiffs' Evidentiary Objections", In the United States District Court for the District of Delaware, Case No. 1:05-cv-00642-JJF, Doc. 170, filed Feb. 6, 2008, 12 pages.
"Redacted Public Version, Defendants' Proposed Findings of Fact and Conclusions of Law" in the United States District Court for the District of Delaware, Case No. 1:05-cv-00642-JJF, Doc. 184, filed Jun. 24, 2008, 134 pages.
"Redacted Public Version, Plaintiffs' Opening Post-Trial Brief Concerning Evidentiary Objections", In the United States District Court for the District of Delaware, Case No. 1:05-cv-00642-JJF, Doc. 167, filed Jan. 30, 2008, 22 pages.
"Redacted Public Version, Plaintiffs' Opening Pretrial Submission", In the United States District Court for the District of Delaware, Case No. 1:05-cv-00642-JJF, Doc. 164, filed Jan. 8, 2008, 135 pages.
"Redacted Public Version, Plaintiffs' Proposed Post-Trial Findings of Fact and Conclusions of Law" in the United States District Court for the District of Delaware, Case No. 1:05-cv-00642-JJF, Doc. 183, filed Jun. 23, 2008, 237 pages.
"Redacted PX 17 Confidential", In the United States District Court for the District of Delaware, Case No. 1:05-cv-00642-JJF, Doc. 163-2, filed Jan. 7, 2008, 1 page.
"Redacted PX 257 Confidential", In the United States District Court for the District of Delaware, Case No. 1:05-cv-00642-JJF, Doc. 163-6, filed Jan. 7, 2008, 1 page.
"Reply to Counterclaims", In the United States District Court for the District of Delaware, Case No. 1:10-cv-00023-LPS, Filed Mar. 31, 2010, 4 pages.
"Response", In the United States District Court for the District of Delaware, Case No. 1:05-cv-00642-JJF, Doc. 156-2, filed Jan. 4, 2008, 46 pages.
"Response", In the United States District Court for the District of Delaware, Case No. 1:05-cv-00642-JJF, Doc. 156-3, filed Jan. 4, 2008, 39 pages.
"The Individual Plasma Concentration Data in Defendants' ANDA Does Not Demonstrate that a Substantial Population of Individuals Will Exhibit a Substantially Ascending MPH Plasma Concentration for About 8 Hours", In the United States District Court for the District of Delaware, Case No. 1:05-cv-00642-JJF, Doc. 156-1, filed Jan. 4, 2008, 65 pages.
"Letter from Ashby & Geddes dated Aug. 20, 2007", In the United States District Court for the District of Delaware, Case No. 1:05-cv-00642-JJF, Doc. 124, filed Aug. 20, 2007, 1 page.
"Exhibit 3—Email from Todd Wagner dated Dec. 5, 2007" in the United States District Court for the District of Delaware, Case No. 1:05-cv-00642-JJF, Doc. 170-3, filed Feb. 6, 2008, 2 pages.
"Letter from Rawle & Henderson LLP dated Apr. 2, 2008" in the United States District Court for the District of Delaware, Case No. 1:05-cv-00642-JJF, Doc. 172-1, filed Apr. 2, 2008, 2 pages.
"U.S. Patent No. 6,930,129 82" in the United States District Court for the District of Delaware, Case No. 1:05-cv-00642-JJF, Doc. 33-2, filed Oct. 20, 2010, 81 pages.
"Defendants Osmotica Kereskedelmi Es Szolgaltato Kft's and Osmotica Pharmaceutical Corp.'s Preliminary Invalidity Contentions Under Paragraph 4(d) of the District of Delaware Default Standard for Discovery", In the United States District Court for the District of Delaware, Case No. 13/1104-RGA (Consolidated), filed Jan. 14, 2014, 106 pages.
"Par Pharmaceutical, Inc.'s Initial Invalidity Contentions Under Paragraph 4 of the District of Delaware Default Standard for Discovery", In the United States District Court for the District of Delaware, Case No. 13/1104-RGA (Consolidated), filed Jan. 14, 2014, 32 pages.
*Alza Corp. et al. v. Andrx Pharmaceuticals LLC et al.*, U.S. Court of Appeals for the Federal Circuit, Case No. 2009-1350, Apr. 26, 2010, 16 pages.
Chemical Engineer's Handbook, 1984, 6th Edition, 21-15.
Conley et al., "Clinical Spectrum of the Osmotic-Controlled Release Oral Delivery System (OROS), an Advanced Oral Delivery form", Current Medical Research and Opinion, Oct. 2006, 22(10):1879-1892.
Drill, Pharmacology in Medicine, *Third Edition*, 1965, 227, McGraw-Hill, New York, p. 798.
Goodman and Gilman, The Pharmacological Bases of Therapeutics, 1990, 8th Ed., 72.
Hubbard, J.W. et al., "Enantioselective Aspects of the Disposition of dl-threo-Methylphenidate after the Administration of a Sustained-Release Formulation to Children with Attention-Hyperactivity Disorder", *Journal of Pharmaceutical Sciences*, 1989, 78(11), 944-947.
In the United States District Court for the District of Delaware, *Alza Corporation, and McNeil-PPC, Inc., Plaintiffs,* v. *Impax Laborato-*

(56) References Cited

OTHER PUBLICATIONS ries, Inc., Andrx Pharmaceuticals, L.L.C., and, Andrx Corporation, Defendants, Civil Action No. 05-642, Answer, Affirmative Defenses and Counterclaims, Oct. 25, 2005, 16 pages.
In the United States District Court for the District of Delaware, *Alza Corporation, and McNeil-PPC, Inc., Plaintiffs*, v. *Impax Laboratories, Inc., Andrx Pharmaceuticals, L.L.C., and, Andrx Corporation*, Defendants, Civil Action No. 05-642-JJF, Reply to Counterclaims, Nov. 14, 2005, 4 pages.
In the United States District Court for the District ofDelaware, *Alza Corporation, and McNeil-PPC, Inc., Plaintiffs*, v. *Impax Laboratories, Inc., Andrx Pharmaceuticals, L.L.C., and, Andrx Corporation*, Defendants, Civil Action No. 05-642, Complaint, Sep. 1, 2005, 15 pages.
Journal of the American Pharmaceutical Association., 1959, 48, 451-454.
Journal of the American Pharmaceutical Association., 1960, 49, 82-84.
Letter from Mark C. Shaw, Vice-President, Regulatory Affairs and Compliance, Impax Laboratories, Inc., t' McNeil Consumer and Specialty Pharmaceuticals & Alza Corporation, Re: Notice under 21 U.S.C. § 355 G)(2)(B)(i) and (ii), With Reference to U.S. Patent No. 6,930,129, Aug. 16, 2005, 8 pages.
Letter from Mark C. Shaw, Vice-President, Regulatory Affairs and Compliance, Impax Laboratories, Inc., to McNeil Consumer and Specialty Pharmaceuticals & Alza Corporation, Re: Notice under 21 U.S.C. § 355 (j){2)(B)(i) and (ii), With Reference to U.S. Patent No. 6,919,373, Jul. 20, 2005, 13 pages.
Letter from Ted Whitlock, Intellectual Property Counsel, Andrx Pharmaceuticals, LLC to ALZA Corporation, Re: ANDA for Concerta® Extended-release Tablets 54 mg; Patent Certification Under 21 CFR § 314.94 and Notice of Certification of Invalidity or Noninfringement of a Patent Under 21 CFR § 314.95, in reference to U.S. Pat. Nos. 6,919,373 & 6,930,129, Aug. 16, 2005, 45 pages.
Letter from Ted Whitlock, Intellectual Property Counsel, Andrx Pharmaceuticals, LLC. to McNeil Consumers & Specialty Pharmaceuticals, Re: ANDA for Concerta® Extended-release Tablets 54 mg; Jul. 20, 2005, 39 pages.
Letter from Ted Whitlock, Intellectual Property Counsel, Andrx Pharmaceuticals, LLC. To McNeil Consumers & Specialty Pharmaceuticals, Re: ANDA for Concerta® Extended-release Tablets 18, 27 and 36 mg, Jul. 20, 2005, 11 pages.
Longer, M.A. et al., "Sustained Release Drug Delivery Systems", 1676-1686.
Medicine Abstract 92226085—Fitzpatrick,1992.
Merck Index, 11th Edition, Item 6025, 1989, p. 960.
Merck Index, 12th Edition, p. 1042, Entry 6189, 1996.
Modem Plastics Encyclopedia, 1969, 46, 62-70.
Park, K. et al., "Use of a Pharmacokinetic/Pharmacodynamic Model to Design an Optimal Dose Input Profile", Journal of Pharmacokinetics and Biopharmaceutics, 1998, 26(4), 471-492.
Physician's Desk Reference, 451, Edition, pp. 865-866, 1991.
Remington, Pharm. Sci., 1970, 14th Edition, 1626-1679.
Remington, Pharm. Sci., 1985, 17th Edition, Chapter 68, 1305-1306.
Remington, Pharm. Sci., 1985, 17th Edition, 342-345.
Remington, Pharm. Sci., 1985, 17th Edition,1603-1632.
Roff, et al., *Handbook of Common Polymers*, 1971, published by CRC Press, 164-173.
Voigt, R., "Theraputische Systeme", *Pharmazeutische Technologie*, 1993, 556-557.
"Defendant Sandoz's Answer, Affirmative Defenses and Counterclaims to Plaintiffs' Complaint", In the United States District Court for the District of Delaware, Case No. 1:14-cv-00744-RGA, Doc. No. 9, filed Aug. 27, 2014, 41 pages.
"Exhibit 1 to Answer", In the United States District Court for the District of Delaware, Case No. 1:14-cv-00744-RGA, Doc. No. 9-1, filed Aug. 27, 2014, 18 pages.
"Exhibit 2 to Answer", In the United States District Court for the District of Delaware, Case No. 1:14-cv-00744-RGA, Doc. No. 9-2, filed Aug. 27, 2014, 17 pages.
"Exhibit 3 to Answer", In the United States District Court for the District of Delaware, Case No. 1:14-cv-00744-RGA, Doc. No. 9-3, filed Aug. 27, 2014, 55 pages.
"Exhibit 4 to Answer", In the United States District Court for the District of Delaware, Case No. 1:14-cv-00744-RGA, Doc. No. 9-4, filed Aug. 27, 2014, 31 pages.
"Exhibit 5 to Answer", In the United States District Court for the District of Delaware, Case No. 1:14-cv-00744-RGA, Doc. No. 9-5, filed Aug. 27, 2014, 21 pages.
"Defendant Alza Corporation's Opening Claim Construction Brief Pursuant to Patent Local Rule 4-5", In the United States District Court for the Northern District of California, Case No. 4:12-cv-04579-PJH, Doc. No. 105, filed Nov. 27, 2013, 30 pages.
"Declaration of Kennerly S. Patrick, Ph.D. In Support of ALZA Corporation's Opening Claim Construction Brief", In the United States District Court for the Northern District of California, Case No. 4:12-cv-04579-PJH, Doc. No. 105-1, filed Nov. 27, 2013, 18 pages.
"Exhibit A of Declaration of Kennerly S. Patrick, Ph.D. in Support of ALZA Corporation's Opening Claim Construction Brief", In the United States District Court for the Northern District of California, Case No. 4:12-cv-04579-PJH, Doc. No. 105-2, filed Nov. 27, 2013, 25 pages.
"Exhibit B of Declaration of Kennerly S. Patrick, Ph.D. In Support of ALZA Corporation's Opening Claim Construction Brief", In the United States District Court for the Northern District of California, Case No. 4:12-cv-04579-PJH, Doc. No. 105-3, filed Nov. 27, 2013, 2 pages.
"Exhibit C of Declaration of Kennerly S. Patrick, Ph.D. in Support of ALZA Corporation's Opening Claim Construction Brief", In the United States District Court for the Northern District of California, Case No. 4:12-cv-04579-PJH, Doc. No. 105-4, filed Nov. 27, 2013, 2 pages.
"Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106, filed Nov. 27, 2013, 5 pages.
"Exhibit 1 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-2, filed Nov. 27, 2013, 17 pages.
"Exhibit 2 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-1, filed Nov. 27, 2013, 17 pages.
"Exhibit 3 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-2, filed Nov. 27, 2013, 24 pages.
"Exhibit 4 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-3, filed Nov. 27, 2013, 9 pages.
"Exhibit 5 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-4, filed Nov. 27, 2013, 13 pages.
"Exhibit 6 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-5, filed Nov. 27, 2013, 17 pages.
"Exhibit 7 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-7, filed Nov. 27, 2013, 11 pages.

(56) References Cited

OTHER PUBLICATIONS

"Exhibit 8 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-8, filed Nov. 27, 2013, 9 pages.

"Exhibit 9 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-9, filed Nov. 27, 2013, 8 pages.

"Exhibit 10 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-10, filed Nov. 27, 2013, 5 pages.

"Exhibit 11 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-11, filed Nov. 27, 2013, 12 pages.

"Exhibit 12 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-12, filed Nov. 27, 2013, 9 pages.

"Exhibit 13 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-13, filed Nov. 27, 2013, 29 pages.

"Exhibit 14 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-14, filed Nov. 27, 2013, 12 pages.

"Exhibit 15 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-15, filed Nov. 27, 2013, 9 pages.

"Exhibit 16 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-16, filed Nov. 27, 2013, 18 pages.

"Exhibit 17 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 106-17, filed Nov. 27, 2013, 2 pages.

"Exhibit 18 (Part 1) of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107, filed Nov. 27, 2013, 32 pages.

"Exhibit 18 (Part 2) of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-1, filed Nov. 27, 2013, 25 pages.

"Exhibit 19 (Part 1) of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-2, filed Nov. 27, 2013, 30 pages.

"Exhibit 19 (Part 2) of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-3, filed Nov. 27, 2013, 36 pages.

"Exhibit 20 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-4, filed Nov. 27, 2013, 5 pages.

"Exhibit 21 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-5, filed Nov. 27, 2013, 7 pages.

"Exhibit 22 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-6, filed Nov. 27, 2013, 4 pages.

"Exhibit 23 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-7, filed Nov. 27, 2013, 31 pages.

"Exhibit 24 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-8, filed Nov. 27, 2013, 32 pages.

"Exhibit 25 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-9, filed Nov. 27, 2013, 4 pages.

"Exhibit 26 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-10, filed Nov. 27, 2013, 5 pages.

"Exhibit 27 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-11, filed Nov. 27, 2013, 6 pages.

"Exhibit 28 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-12, filed Nov. 27, 2013, 19 pages.

"Exhibit 29 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-13, filed Nov. 27, 2013, 53 pages.

"Exhibit 30 of Declaration of Kurt G. Calia in Support of Alza Corp.'s Opening Claim Construction Brief Pursuant to Patent Local Rule 4-5", In the United States District Court for the Northern District of California, Case No. 4:12-cv-04579-PJH, Doc. No. 107-14, filed Nov. 27, 2013, 20 pages.

"Plaintiff Dr. James M. Swanson's Responsive Claim Construction Brief", In the United States District Court for the Northern District of California, Case No. 4:12-cv-04579-PJH, Doc. No. 112, filed Dec. 13, 2013, 30 pages.

"Exhibit A to Declaration of Plaintiff Swanson's in Support of Claim Construction Brief", In the United States District Court for the Northern District of California, Case No. 4:12-cv-04579-PJH, Doc. No. 113-1, filed Dec. 13, 2013, 31 pages.

"Declaration Gerald P. Dodson in Support of Dr. James M. Swanson's Responsive Claim Construction Brief", In the United States District Court for the Northern District of California, Case No. 4:12-cv-04579-PJH, Doc. No. 114, filed Dec. 13, 2013, 5 pages.

"Exhibit B to Declaration Gerald P. Dodson in Support of Dr. James M. Swanson's Responsive Claim Construction Brief", In the United

(56) References Cited

OTHER PUBLICATIONS

States District Court for the Northern District of California, Case No. 4:12-cv-04579-Pjh, Doc. No. 114-1, filed Dec. 13, 2013, 8 pages.
"Exhibit C to Declaration Gerald P. Dodson in Support of Dr. James M. Swanson's Responsive Claim Construction Brief", In the United States District Court for the Northern District of California, Case No. 4:12-cv-04579-PJH, Doc. No. 114-2, filed Dec. 13, 2013, 15 pages.
"Exhibit D to Declaration Gerald P. Dodson in Support of Dr. James M. Swanson's Responsive Claim Construction Brief", In the United States District Court for the Northern District of California, Case No. 4:12-cv-04579-PJH, Doc. No. 114-3, filed Dec. 13, 2013, 21 pages.
"Exhibit E to Declaration Gerald P. Dodson in Support of Dr. James M. Swanson's Responsive Claim Construction Brief", In the United States District Court for the Northern District of California, Case No. 4:12-cv-04579-PJH, Doc. No. 114-4, filed Dec. 13, 2013, 14 pages.
"Exhibit F to Declaration Gerald P. Dodson in Support of Dr. James M. Swanson's Responsive Claim Construction Brief", in the United States District Court for the Northern District of California, Case No. 4:12-cv-04579-PJH, Doc. No. 114-5, filed Dec. 13, 2013, 4 pages
"Exhibit G to Declaration Gerald P. Dodson in Support of Dr. James M. Swanson's Responsive Claim Construction Brief", In the United States District Court for the Northern District of California, Case No. 4:12-cv-04579-PJH, Doc. No. 114-6, filed Dec. 13, 2013, 2 pages.
"Exhibit H to Declaration Gerald P. Dodson in Support of Dr. James M. Swanson's Responsive Claim Construction Brief", In the United States District Court for the Northern District of California, Case No. 4:12-cv-04579-PJH, Doc. No. 114-7, filed Dec. 13, 2013, 10 pages.
"Exhibit J to Declaration Gerald P. Dodson in Support of Dr. James M. Swanson's Responsive Claim Construction Brief", In the United States District Court for the Northern District of California, Case No. 4:12-cv-04579-PJH, Doc. No. 114-8, filed Dec. 13, 2013, 38 pages.
"Exhibit K to Declaration Gerald P. Dodson in Support of Dr. James M. Swanson's Responsive Claim Construction Brief", In the United States District Court for the Northern District of California, Case No. 4:12-cv-04579-PJH, Doc. No. 114-9, filed Dec. 13, 2013, 5 pages.
"Exhibit L to Declaration Gerald P. Dodson in Support of Dr. James M. Swanson's Responsive Claim Construction Brief", In the United States District Court for the Northern District of California, Case No. 4:12-cv-04579-PJH, Doc. No. 114-10, filed Dec. 13, 2013, 2 pages.
"Exhibit M to Declaration Gerald P. Dodson in Support of Dr. James M. Swanson's Responsive Claim Construction Brief", In the United States District Court for the Northern District of California, Case No. 4:12-cv-04579-PJH, Doc. No. 114-11, filed Dec. 13, 2013, 2 pages.
"Exhibit N To Declaration Gerald P. Dodson in Support of Dr. James M. Swanson's Responsive Claim Construction Brief", In the United States District Court for the Northern District of California, Case No. 4:12-cv-04579-PJH, Doc. No. 114-12, filed Dec. 13, 2013, 21 pages.
"Exhibit O to Declaration Gerald P. Dodson in Support of Dr. James M. Swanson's Responsive Claim Construction Brief", In the United States District Court for the Northern District of California, Case No. 4:12-cv-04579-PJH, Doc. No. 114-13, filed Dec. 13, 2013, 4 pages.
"Exhibit P To Declaration Gerald P. Dodson in Support of Dr. James M. Swanson's Responsive Claim Construction Brief", In the United States District Court for the Northern District of California, Case No. 4:12-cv-04579-PJH, Doc. No. 115, filed Dec. 13, 2013, 19 pages.
"Exhibit Q to Declaration Gerald P. Dodson in Support of Dr. James M. Swanson's Responsive Claim Construction Brief", In the United States District Court for the Northern District of California, Case No. 4:12-cv-04579-PJH, Doc. No. 115-1, filed Dec. 13, 2013, 3 pages.
"Exhibit R to Declaration Gerald P. Dodson in Support of Dr. James M. Swanson's Responsive Claim Construction Brief", In the United States District Court for the Northern District of California, Case No. 4:12-cv-04579-PJH, Doc. No. 115-2, filed Dec. 13, 2013, 11 pages.
"Exhibit S to Declaration Gerald P. Dodson in Support of Dr. James M. Swanson's.Responsive Claim Construction Brief", In the United States District Court for the Northern District of California, Case No. 4:12-cv-04579-PJH, Doc. No. 115-3, filed Dec. 13, 2013, 17 pages.
"Exhibit T to Declaration Gerald P. Dodson in Support of Dr. James M. Swanson's Responsive Claim Construction Brief", In the United States District Court for the Northern.District of California, Case No. 4:12-cv-04579-PJH, Doc. No. 115-4, filed Dec. 13, 2013, 24 pages.
"Exhibit U (Filed Under Seal) to Declaration Gerald P. Dodson in Support of Dr. James M. Swanson's Responsive Claim Construction Brief", In the United States District Court for the Northern District of California, Case No. 4:12-cv-04579-PJH, Doc. No. 115-5, filed Dec. 13, 2013, 57 pages.
"Exhibit V to Declaration Gerald P. Dodson in Support of Dr. James M. Swanson's Responsive Claim Construction Brief", In the United States District Court for the Northern District of California, Case No. 4:12-cv-04579-PJH, Doc. No. 115-6, filed Dec. 13, 2013, 45 pages.
"Exhibit W to Declaration Gerald P. Dodson in Support of Dr. James M. Swanson's Responsive Claim Construction Brief", In the United States District Court for the Northern District of California, Case No. 4:12-cv-04579-PJH, Doc. No. 115-7, filed Dec. 13, 2013, 11 pages.
"Exhibit X (Part 1) to Declaration Gerald P. Dodson in Support of Dr. James M. Swanson's Responsive Claim Construction Brief", in the United States District Court for the Northern District of California, Case No. 4:12-cv-04579-PJH, Doc. No. 115-8, filed Dec. 13, 2013, 75 pages.
"Exhibit X (Part 2) to Declaration Gerald P. Dodson in Support of Dr. James M. Swanson's Responsive Claim Construction Brief", In the United States District Court for the Northern District of California, Case No. 4:12-cv-04579-PJH, Doc. No. 115-9, filed Dec. 13, 2013, 56 pages.
"Exhibit Y (Filed Under Seal) to Declaration Gerald P. Dodson in Support of Dr. James M. Swanson's Responsive Claim Construction Brief", In the United States District Court for the Northern District of California, Case No. 4:12-cv-04579-PJH, Doc. No. 115-12, filed Dec. 13, 2013, 167 page.
"Exhibit Z to Declaration Gerald P. Dodson in Support of Dr. James M. Swanson's Responsive Claim Construction Brief", In the United States District Court for the Northern District of California, Case No. 4:12-cv-04579-PJH, Doc. No. 115-13, filed Dec. 13, 2013, 19 pages.
"Exhibit AA (Filed Under Seal) to Declaration Gerald P. Dodson in Support of Dr. James M.Swanson's Responsive Claim Construction Brief", In the United States District Court for the Northern District of California, Case No. 4:12-cv-04579-PJH, Doc. No. 115-14, filed Dec. 13, 2013, 65 pages.
"Exhibit BB to Declaration Gerald P. Dodson in Support of Dr. James M. Swanson's Responsive Claim Construction Brief", In the United States District Court for the Northern District of California, Case No. 4:12-cv-04579-PJH, Doc. No. 116, filed Dec. 13, 2013, 48 pages.
"Exhibit CC (Part 1a) to Declaration Gerald P. Dodson in Support of Dr. James M.Swanson's Responsive Claim Construction Brief", In the United States District Court for the Northern District of California, Case No. 4:12-cv-04579-PJH, Doc. No. 116-1, filed Dec. 13, 2013, 70 pages.
"Exhibit CC (Part 1b) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-2, filed Dec. 13, 2013, 65 pages.
"Exhibit CC (Part 2a) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-3, filed Dec. 13, 2013, 60 pages.
"Exhibit CC (Part 2b) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-4, filed Dec. 13, 2013, 76 pages.
"Exhibit CC (Part 3a) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-5, filed Dec. 13, 2013, 70 pages.
"Exhibit CC (Part 3b) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-6, filed Dec. 13, 2013, 66 pages.

(56) References Cited

OTHER PUBLICATIONS

"Exhibit CC (Part 4a) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-7, filed Dec. 13, 2013, 70 pages.
"Exhibit CC (Part 4b) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-8, filed Dec. 13, 2013, 66 pages.
"Exhibit CC (Part 5a) to Declaration Gerald P. Dodson in Support of Dr. James M.Swanson's Responsive Claim Construction Brief", In the United States District Court for the Northern District of California, Case No. 4:12-cv-04579-PJH, Doc. No. 116-9, filed Dec. 13, 2013, 70 pages.
"Exhibit CC (Part 5b) to Declaration Gerald P. Dodson in Support of Dr. James M. Swanson's Responsive Claim Construction Brief", In the United States District Court for the Northern District of California, Case No. 4:12-cv-04579-PJH, Doc. No. 116-10, filed Dec. 13, 2013, 51 pages.
"Redacted Public Version—Defendants' Osmotica Kereskedelmi Es Szolgaltato Kft's and Osmotica Pharmaceutical Corp.'s Answer, Defenses, and Counterclaims to Plaintiffs' Amended Complaint", In the United States District Court for the District of Delaware, Case No. 1:13-cv-1104-RGA (Consolidated), Jury Demanded, Doc. No. 121, filed Apr. 4, 2014, 52 pages.
"Defendant Alza Corporation's Administrative Request to File Under Seal Portions of the Claim Construction Reply Brief", In the United States District Court for the Northern District of California, Case No. 4:12-cv-04579-PJH, Doc. No. 130, filed Dec. 20, 2013, 3 pages.
"Redacted Defendant Alza Corporation's Claim Construction Reply Brief Pursuant to Patent Local Rule 4-5", In the United States District Court for the Northern District of California, Case No. 4:12-cv-04579-PJH, Doc. No. 130-3, filed Dec. 20, 2013, 27 pages.
"Under Seal Defendant Alza Corporation's Claim Construction Reply Brief Pursuant to Patent Local Rule 4-5", In the United States District Court for the Northern District of California, Case No. 4:12-cv-04579-PJH, Doc. No. 130-4, filed Dec. 20, 2013, 20 pages.
"Confidential—Filed Under Seal Pursuant to Protective Order, Defendants' Osmotica Kereskedelmi Es Szolgaltato Kft's And Osmotica Pharmaceutical Corp.'s Amended Answer, Defenses, and Counterclaims to Plaintiffs' Amended Complaint", In the United States District Court for the District of Delaware, Case No. 1:13-cv-1104-RGA (Consolidated), Jury Demanded, Doc. No. 144, filed Jun. 6, 2014, 60 pages.
"Confidential Filed Under Seal—Defendant Par Pharmaceutical Inc.'s First Amended Answer and Counterclaims to Alza Corporation and Janssen Pharmaceuticals, Inc.'s Amended Complaint", In the United States District Court for the District of Delaware, Case No. 1:13-cv-1104-RGA (Consolidated), Doc. No. 145, filed Jun. 6, 2014, 141 pages.
"Public Exhibits to Par Pharmaceutical Inc.'s First Amended Answer and Counterclaims to Alza Corporation and Janssen Pharmaceuticals, Inc.'s Amended Complaint", In the United States District Court for the District of Delaware, Case No. 1:13-cv-1104-RGA (Consolidated), Doc. No. 146, filed Jun. 6, 2014, 173 pages.
"Plaintiff's Order Construing Claims Construction", In the United States District Court for the Northern District of California, Case No. 4:12-cv-04579-PJH, Doc. No. 157, filed Apr. 25, 2014, 30 pages.
"Proposed Order Granting Plaintiff Dr. James M. Swanson's Motion For Leave to Amend Inventorship and Invalidity Contentions", In the United States District Court for the Northern District of California, Oakland Division, Case No. 4:12-cv-04579-PJH, Doc. No. 191-1, filed Jul. 11, 2014, 1 page.
"Declaration of K. Brian Bathurst in Support of Plaintiff Dr. James M. Swanson's Notice of Motion and Motion for Leave to Amend his Inventorship and Invalidity Contentions (N.D.Cal. Patent L.R. 3-6)", In the United States District Court for the Northern District of California, Oakland Division, Case No. 4:12-cv-04579-PJH, Doc. No. 191-2, filed Jul. 11, 2014, 2 pages.
"Exhibit Claim Chart Invalidity Contentions", In the United States District Court for the Northern District of California, Oakland Division, Case No. 4:12-cv-04579-PJH, Doc. No. 191-3, filed Jul. 11, 2014, 17 pages.
"Exhibits to Defendants Osmotica's Complaint", 2013, 77 pages.
"Plaintiff Dr. James M. Swanson's Responses to Alza Corporation's Fourth Set of Interrogatories (Original Interrogatory No. 9/New Interrogatory No. 19", In the United States.District Court for the Northern District of California, Case No. 4:12-cv-04579-PJH, filed Dec. 13, 2013, 8 pages.
"Plaintiff Dr. James M. Swanson's Responses to Alza Corporation's Third Set of Interrogatories", In the United States District Court for the Northern District of California, Case No. 4:12-cv-04579-PJH, filed Oct. 30, 2013, 48 pages.
"Plaintiff Dr. James M. Swanson's Responses to Alza Corporation's Fifth Set of Interrogatories (Original Interrogatory Nos. 10-12/New Interrogatory Nos. 20-22)", In The United States District Court for the Northern District of California, Case No. 4:12-cv-04579- PJH, filed Apr. 7, 2014, 10 pages.
"Plaintiff Dr. James M. Swanson's Supplemental Responses to Alza Corporation's Fourth Set of Interrogatories (Original Interrogatory No. 9/New Interrogatory No. 19)", In The United States District Court for the Northern District of California, Case No. 4:12-cv-04579-PJH, filed Jan. 23, 2014, 9 pages.
"Plaintiff Dr. James M. Swanson's Supplemental Responses to Alza Corporation's Third Set of Interrogatories", In the United States District Court for the Northern District of California, Case No. 4:12-cv-04579-PJH, filed Jun. 4, 2014, 55 pages.
ALZA Corporation's Claim Construction Presentation, Feb. 3, 2014, 95 pages.
Letter from Amneal Pharmaceuticals, "Notice of Paragraph IV Certification of U.S. Patent 6,919,373, 6,930,129, 8,163,798 and 8,629,179, Concerning ANDA 207515 for Methylphenidate Hydrochloride Extended-Release Tablets USP, 18 mg, 27 mg, 36 mg and 54 mg", dated Aug. 22, 2014, 14 pages.
Plaintiff Swanson's Claim Construction Presentation, Feb. 3, 2014, 42 pages.
"A 14-Month Randomized Clinical Trial of Treatment Strategies for Attention-Deficit/Hyperactivity Disorder, The MTA Cooperative Group", Produced in 12-CV-04579, ALZ00004854-4867, Arch Gen. Psychiatry, 1999, 56, 1073-1086.
"*Alza Corp. and McNeil PPC, Inc.* v. *Andrx Pharmaceuticals, LLC and Andrx Corporation*, 603 F.3d 935 (Fed. Cir. 2010)", In the United States Court of Appeals, Federal Circuit, No. 2009-1350, Apr. 26, 2010, 935-943.
"*Alza Corp. and McNeil PPC, Inc.* v. *Andrx Pharmaceuticals, LLC and Andrx Corporation*, 607 F.Supp.2d 935 (D.Del. 2009)", In the United States District Court for the District of Delaware, Civil Action No. 05-642-JJF, Mar. 30, 2009, 614-660.
"Answer, Defenses and Counterclaims of Mylan Pharmaceuticals Inc. and Mylan Inc. to Plaintiffs' Complaint", In the United States District Court for the Northern District of West Virginia (at Clarksburg), Case No. 1:14-cv-00085-IMK, Doc. No. 11, filed Jul. 29, 2014, 25 pages.
"Birkett, Chapter 12—Designing Dose Regimens, Effects of Varying the Dose Interval, Pocket Guide: Pharmacokinetics Made Easy, 1998, p. 101", In the United States District Court for the Northern District of California, Oakland Division, Case No. 4:12-cv-04579-PJH, Doc. No. 114-11, filed Dec. 13, 2013, 1 page.
"Certified Copy of U.S. Appl. No. 60/028,726", In the United States Patent and Trademark Office, filed Sep. 30, 1996, 54 pages.
"Chan et al, Methylphenidate Hydrochloride Given With or Before Breakfast: II. Effects on Plasma Concentration of Methylphenidate and Ritalinic Acid, Pediatrics, 1983, 72(1), 56-59", In the United States District Court for the Northern District of California, Oakland Division, Case No. 4:12-cv-04579-PJH, Doc. No. 114-9, filed Dec. 13, 2013, 5 pages.
"Confidential—Attorneys Eyes Only Subject to the Protective Order, Video Deposition of Edward L. Mandell", In the United States Dis-

(56) References Cited

OTHER PUBLICATIONS trict Court for the Northern District of California, Oakland Division, Case No. 4:12-cv-04579-PJH, ALZ01491792-1900, dated Sep. 30, 2013, 109 pages.

"Declaration of Plaintiff, James M. Swanson, Ph.D. In Support of Dr. Swanson's Responsive Claim Construction Brief", In the United States District Court for the Northern District of California, Oakland Division, Case No. 4:12-cv-04579-PJH, Doc. No. 113, filed Dec. 13, 2013, 16 pages.

"Defendant Osmotica's Brief in Opposition to Plaintiffs' Motion to Strike Defenses and Dismiss Counterclaims Alleging Inequitable Conduct", In the United States District Court for the District of Delaware, C.A. No. 13-1104-RGA (Consolidated), filed Apr. 11, 2014, 8 pages.

"Defendant Osmotica's Brief in Opposition to Plaintiffs' Motion to Strike Defenses and Dismiss Counterclaims Alleging Inequitable Conduct", In the United States District Court for the District of Delaware, Case No. 1:13-1104-RGA (Consolidated), Doc. No. 132, filed Apr. 28, 2014, 8 pages.

"Defendant Par Pharmaceutical Inc.'s Answer and Counterclaims to Alza Corporation and Janssen Pharmaceuticals, Inc.'s Amended Complaint", In the United States District Court for the District of Delaware, Case No. 1:13-1104-RGA (Consolidated), Doc. No. 118, filed Mar. 28, 2014, 101 pages.

"Defendant Par Pharmaceutical, Inc.'s Initial Invalidity Contentions for U.S. Patent No. 8,629,179 And Supplemental Invalidity Contentions for U.S. Patent No. 8,163,798", In the United States District Court for the District of Delaware, C.A. No. 13-1104-RGA (Consolidated), filed Apr. 10, 2014, 54 pages.

"Defendant Par Pharmaceuticals Inc.'s Answer and Counterclaims", In the United States District Court for the District of Delaware, Case No. 1:13-cv-1104 (RGA), filed Sep. 9, 2013, 52 pages.

"Defendants Osmotica Kereskedelmi Es Szolgaltato Kft's and Osmotica Pharmaceutical Corp.'s Preliminary Invalidity Contentions for U.S. Patent No. 8,629,179 Under Paragraph 4(D) of the District of Delaware Default Standard for Discovery", In the United States District Court for the District of Delaware, C.A. No. 13-1104-RGA (Consolidated), filed Apr. 10, 2014, 151 pages.

"DTX-153—Perel, et al., Abstracts of Papers Presented at the Ninety-Second Annual Meeting of the American Society for Clinical Pharmacology and Therapeutics", Clinical Pharmacology and Therapeutics, Feb. 1991, 49(2), 3 pages.

"DTX-621—Pelham Jr., et al., Sustained Release and Standard Methylphenidate Effects on Cognitive and Social Behavior in Children With Attention Deficit Disorder", Pediatrics, 1987, 80, 491-501, In the United States District Court for the District of Delaware, Case No. 1:05-cv-000642-JJF, Doc. No. 161-2, filed Jan. 7, 2008, 11 pages.

"DTX-622—Pelham et al., Relative Efficacy of Long-Acting Stimulants on Children With Attention Deficit-Hyperactivity Disorder: A Comparison of Standard Methylphenidate, Sustained-Release Methylphenidate, Sustained-Release Dextroamphetamine, and Pemoline", Pediatrics, Aug. 1990, 86(2), 226-237, In the United States District Court for the District of Delaware, Case No. 1:05-cv-00642-JJF, Doc. 161-3, filed Jan. 7, 2008, 12 pages.

"DTX-624—Hubbard et al., Enantioselective Aspects of the Disposition of dl-threo-Methylphenidate after the Administration of a Sustained-Release Formulation to Children with Attention Deficit-Hyperactivity Disorder, Journal of Pharmaceutical Sciences, Nov. 1989, 78(11), 944-947", In the United States District Court for the District of Delaware, Case No. 1:05-cv-00642-JJF, Doc. 161-4, filed Jan. 7, 2008, 4 pages.

"DTX-626—Angrist, Brain Reward Systems and Abuse: Clinical Effects of Central Nervous System Stimulants: A Selective Update, Engle et al. (Eds)., Seventh International Berzelius Symposium Sponsored by the Swedish Society of Medicine, 1987", In the United States District Court for the District of Delaware, Case No. 1:05-cv-000642-JJF, Doc. No. 161-6, filed Jan. 7, 2008, 21 pages.

"DTX-627—Birmaher et al, Sustained Release Methylphenidate: Pharmacokinetic Studies in ADDH Males, Journal of the American Academy of Child and Adolescent Psychiatry, Sep. 1989, 28(5), 768-772", In the United States District Court for the District of Delaware, Case No. 1:05-cv-000642-JJF, Doc. No. 161-7, filed Jan. 7, 2008, 7 pages.

"DTX-628—Porchet et al., Pharmacodynamic Model of Tolerance: Application to Nicotine, Journal of Pharmacology and Experimental Therapeutics, 1987, 244(1), 231-236", In the United States District Court for the District of Delaware, Case No. 1:05-cv-00642-JJF, Doc. 161-8, filed Jan. 7, 2008, 6 pages.

DTX-629—Perkins et al., Acute Tolerance to the Cardiovascular Effects of Nicotine, Drug and Alcohol Dependence, 1991, 29, 77-86, In the United States District Court for the District of Delaware, Case No. 1:05-cv-00642-JJF, Doc. 161-9, filed Jan. 7, 2008, 9 pages.

"DTX-630—Greenhill, The Psychiatric Clinics of North America: Pediatric Psychopharmacology, Pharmacologic Treatment of Attention Deficit Hyperactivity Disorder", W.B. Saunders Co., Mar. 1992, 15(1), 29 pages, In the United States District Court for the District of Delaware, Case No. 1:05-cv-000642-JJF, Doc. No. 161-10, filed Jan. 7, 2008, 29 pages.

"DTX-631—Fung, Pharmacokinetic Determinants of Nitrate Action, The American Journal of Medicine, 1984, 22-28", In the United States District Court for the District of Delaware, Case No. 1:05-cv-000642-JJF, Doc. No. 161-11, filed Jan. 7, 2008, 5 pages.

"DTX-635—The Merck Index: An Encyclopedia of Chemicals, Drugs, and Biologicals", 12th Edition, Budavari et al. (Eds.), Merck and Co., Inc., 1996, 4 pages, In the United States.DistrictCourt for the District of Delaware, Case No. 1:05-cv-00642-JJF, Doc. No. 161-15, filed Jan. 7, 2008, 4 pages.

"Exhibit A—Joint Claim Construction Chart", In the United States District Court for the District of Delaware, C.A. No. 13-1104-RGA (Consolidated), Doc. No. 98-1, filed Mar. 4, 2014, 5 pages.

"Exhibit A to Declaration of James M. Swanson, Ph.D.—Curriculum Vitae", In the United States District Court for the Northern District of California, Oakland Division, Case No. 4:12-cv-04579-PJH, Doc. No. 113-1, filed Dec. 13, 2013, 31 pages.

"Exhibit A1—U.S. Appl. No. 12/581,699: Information Disclosure Statement Signed by Examiner Zohreh Fay", In the United States Patent and Trademark Office, Produced in 12-CV-04579, ALZ01176807-6810, dated Nov. 11, 2011, 5 pages.

"Exhibit A2—U.S. Appl. No. 12/581,699: Information Disclosure Statement Signed by Examiner Zohreh Fay", In the United States Patent and Trademark Office, ALZ01608191-8216, dated Sep. 26, 2012, 27 pages.

"Exhibit AA—U.S. Appl. No. 09/802,709: Reply Pursuant to 37 CFR §1.1116", In the United States Patent and Trademark Office, Doc. No. OSM(MET)017857-861, filed Oct. 15, 2003, 6 pages.

"Exhibit AAA—Defendants Osmotica Kereskedelmi Es Szolgaltato Kft's and Osmotica Pharmaceutical Corp.'s Preliminary Invalidity Contentions Under Paragraph 4( D) of the District of Delaware Default Standard for Discovery", In the United States District Court for the District of Delaware, C.A. No. 13-1104-RGA (Consolidated), filed 2014, 5 pages.

"Exhibit B—U.S. Patent No. 8,163,798 B2", In the United States Patent and Trademark Office, dated Apr. 24, 2012, 24 pages.

"Exhibit B1—Defendants Kremers Urban, LLC and Kudco Ireland, Ltd.'s Motion for Leave to File an Amended Answer", In the United States District Court for the District of Delaware, Case No. 10-23-LPS (1:10-cv-00023-LPS), Public Version, Doc. No. 107, filed May 19, 2011, 24 pages.

"Exhibit B2—Defendants Kremers Urban, LLC and Kudco Ireland, Ltd.'s Motion for Leave to File an Amended Answer", In the United States District Court for the District of Delaware, Case No. 10-23-LPS (1:10-cv-00023-LPS), Public Version, Doc. No. 107, filed May 19, 2011, 24 pages.

"Exhibit BB—U.S. Appl. No. 09/802,709: Reply Pursuant to 37 CFR § 1.111", In the United States Patent and Trademark Office, Doc. No. OSM(MET)01792-817, filed Jul. 14, 2004, 7 pages.

"Exhibit BBB—Opening Brief of Plaintiffs-Appellants Alza Corporation and McNeil-PPC, Inc.", In the United States Court of Appeals for the Federal Circuit, No. 2009-1350, filed Aug. 13, 2009, 6 pages.

"Exhibit C—U.S. Appl. No. 10/639,355: Reply Pursuant to 37 CFR § 1.114", In the United States Patent and Trademark Office, filed Oct. 15, 2009, 10 pages.

(56) References Cited

OTHER PUBLICATIONS

"Exhibit C1—Defendants Kremers Urban, LLC and Kudco Ireland, Ltd.'s Opening Brief in Support of Their Motion for Leave to File an Amended Answer", In the United States District Court for the District of Delaware, Case No. 10-23-LPS (1:10-cv-00023-LPS), Public Version, Doc. No. 108, filed May 19, 2011, 25 pages.
"Exhibit C2—Defendants Kremers Urban, LLC and Kudco Ireland, Ltd.'s Opening Brief in Support of Their Motion for Leave to File an Amended Answer", In the United States District Court for the District of Delaware, Case No. 10-23-LPS (1:10-cv-00023-LPS), Public Version, Doc. No. 108, filed May 19, 2011, 25 pages.
"Exhibit CC—U.S. Appl. No. 09/802,709: U.S. Patent No. 6,930,129 Claims", In the United States Patent and Trademark Office, Doc. No. ALZ00946924-30, filed Mar. 8, 2001, 8 pages.
"Exhibit CCC—Order Construing Claims", United States District Court, Northern District of California, No. 12-cv-04579 PJH, Doc. No. 157, filed Apr. 25, 2014, 31 pages.
"Exhibit D—U.S. Appl. No. 60/030,514", In the United States Patent and Trademark Office, Produced in Case No. 12-cv-04579, Doc. No. ALZ01166388-449, filed Nov. 12, 1996, 63 pages.
"Exhibit D1—Declaration of Richard L. Horwitz, Esq. In Support of Defendants Kremers Urban, LLC and Kudco Ireland, Ltd.'s Motion For Leave To File An Amended Answer", In the United States District Court for the District of Delaware, Case No. 10-23-LPS (1:10-cv-00023-LPS), Public Version, Doc. No. 109, filed May 19, 2011, 5 pages.
"Exhibit D2—Declaration of Richard L. Horwitz, Esq. In Support of Defendants Kremers Urban, LLC and Kudco Ireland, Ltd.'s Motion For Leave o File An Amended Answer", In the United States District Court for the District of Delaware, Case No. 10-23-LPS (1:10-cv-00023-LPS), Public Version, Doc. No. 109, filed May 19, 2011, 5 pages.
"Exhibit DD—U.S. Appl. No. 10/638,977: Reply Pursuant to 37 CFR § 1.111", In the United States Patent and Trademark Office, filed Sep. 12, 2012, 11 pages.
"Exhibit E—Swanson et al., Effects of Stimulant Medication on Learning in Children with ADHD, Journal of Learning Disabilities, Apr. 1991, 24(4), 14 pages", In the United States District Court for the Northern District of California, Oakland Division, Case No. 4:12-cv-04579-PJH, Doc. No. 114-4, filed Dec. 13, 2013, 14 pages.
"Exhibit E—U.S. Appl. No. 60/044,121", In the United Statement Patent and Trademark Office, Produced in Case No. 12-cv-04579, Doc. No. ALZ01166558-617, filed Apr. 22, 1997, 61 pages.
"Exhibit EE—U.S. Appl. No. 10/638,977: Reply Pursuant to 37 CFR § 1.111", In the United States Patent and Trademark Office, filed Jun. 27, 2013, 4 pages.
"Exhibit F—U.S. Appl. No. 60/031,741", In the United Statement Patent and Trademark Office, Produced in Case No. 12-cv-04579, Doc. No. ALZ01166473-530, filed Nov. 25, 1996, 59 pages.
"Exhibit FF—U.S. Patent No. 7,521,067 B1", In the United States Patent and Trademark Office, Produced in Case No. 12-cv-04579, Doc. No. ALZ00898306-313, dated Apr. 21, 2009, 9 pages.
"Exhibit G—U.S. Appl. No. 08/937,336", In the United States Patent and Trademark Office, Produced in Case No. 12-cv-04579, Doc. No. ALZ01164628-675, filed Aug. 19, 1997, 49 pages.
"Exhibit GG—U.S. Appeal No. 2008-4075: Board Decision on Appeal", In the United States Patent and Trademark Office, Produced in Case No. 12-cv-04579, Doc. No. ALZ00785597-614, decided Sep. 24, 2008, 19 pages.
"Exhibit H—U.S. Appl. No. 09/070,666", In the United States Patent and Trademark Office, Produced in Case No. 12-cv-04579, Doc. No. ALZ01165646-715, filed Apr. 30, 1998, 71 pages.
"Exhibit HH—Pre-Appeal Brief Request for Review", In the United States Patent and Trademark Office, Produced in Case No. 12-cv-04579, Doc. No. ALZ01169809-812, filed Oct. 6, 2010, 5 pages.
"Exhibit I—U.S. Appl. No. 08/910,593", In the United States Patent and Trademark Office, Produced in Case No. 12-cv-04579, Doc. No. ALZ01163888-979, filed Jul. 31, 1997, 93 pages.
Exhibit II—Proposed Constructions and Intrinsic Evidence for U.S. Patent Nos. 8,163,798 and 8,629,179, 2014, 8 pages.

"Exhibit J—U.S. Appl. No. 08/967,606", In the United States Patent and Trademark Office, Produced in Case No. 12-cv-04579, Doc. No. ALZ01163078-140, filed Nov. 10, 1997, 64 pages.
"Exhibit JJ—U.S. Patent No. 8,629,179 B2", In the United States Patent and Trademark Office, dated Jan. 14, 2014, 25 pages.
"Exhibit K—U.S. Patent No. 4,327,725", In the United States Patent and Trademark Office, dated May 4, 1982, 14 pages.
"Exhibit KK—U.S. Appl. No. 12/581,699: Preliminary Amendment", In the United States Patent and Trademark Office, Produced in Case No. 12-cv-04579, Doc. No. ALZ01605825-854, filed Apr. 26, 2010, 31 pages.
"Exhibit L—U.S. Patent No. 4,612,008", In the United States Patent and Trademark Office, dated Sep. 16, 1986, 22 pages.
"Exhibit LL—U.S. Appl. No. 12/581,699: Preliminary Amendment", In the United States Patent and Trademark Office, Doc. No. ALZ01605706-714, filed Oct. 19, 2009, 10 pages.
"Exhibit M—U.S. Patent No. 4,783,337", In the United States Patent and Trademark Office, dated Nov. 8, 1988, 28 pages.
"Exhibit MM—U.S. Appl. No. 12/581,699: Preliminary Amendment", In the United States Patent and Trademark Office, Doc. No. ALZ01605799-811, filed Oct. 19, 2009, 14 pages.
"Exhibit N—U.S. Patent No. 5,082,668", In the United States Patent and Trademark Office, dated Jan. 21, 1992, 29 pages.
"Exhibit NN—U.S. Appl. No. 12/581,699: Preliminary Amendment", In the United States Patent and Trademark Office, Doc. No. ALZ01606278-312, filed Jan. 21, 2011, 36 pages.
"Exhibit O—Preliminary Amendment", In the United States Patent and Trademark Office, Produced in Case No. 12-cv-04579, Doc. No. ALZ011669197-200, filed Aug. 12, 2003, 5 pages.
"Exhibit OO—U.S. Appl. No. 12/581,699: NonFinal Office Action", In the United States Patent and Trademark Office, Doc. No. ALZ01607858-866, dated Apr. 30, 2012, 10 pages.
"Exhibit P—U.S. Appl. No. 10/639,355: NonFinal Office Action", In the United States Patent and Trademark Office, Produced in Case No. 12-cv-04579, Doc. No. ALZ01169405-408, dated Jan. 22, 2007, 5 pages.
"Exhibit PP—U.S. Appl. No. 12/581,699: Reply Pursuant to 37 CFR § 1.111", In the United States Patent and Trademark Office, Doc. No. ALZ01608146-181, filed Jul. 25, 2012, 37 pages.
"Exhibit Q—U.S. Appl. No. 10/639,355: Reply Pursuant to 37 CFR § 1.116", In the United States Patent and Trademark Office, Produced in Case No. 12-cv-04579, Doc. Nos. ALZ01169437, ALZ01169439-440, ALZ0116943-444, filed Mar. 25, 2008, 6 pages.
"Exhibit QQ—U.S. Appl. No. 12/581,699: Final Office Action", In the United States Patent and Trademark Office, Doc. No. ALZ01608183, dated Oct. 2, 2012, 9 pages.
"Exhibit R—U.S. Appl. No. 10/639,355: NonFinal Office Action", In the United States Patent and Trademark Office, Produced in Case No. 12-cv-04579, Doc. No. ALZ01169450-554, dated Jun. 6, 2008, 6 pages.
"Exhibit RR—U.S. Appl. No. 12/581,699: Reply Pursuant to 37 CFR §1.114", In the United States Patent and Trademark Office, Doc. No. ALZ01608338-346, filed Jun. 6, 2013, 10 pages.
"Exhibit S—U.S. Appl. No. 10/639,355: Reply Pursuant to 37 CFR §1.111", In the United States Patent and Trademark Office, Produced in Case No. 12-cv-04579, Doc. Nos. ALZ01169516-519, ALZ01169529, filed Oct. 14, 2008, 6 pages.
"Exhibit SS—U.S. Appl. No. 12/581,699: Reply Pursuant to 37 CFR §1.114", In the United States Patent and Trademark Office, Doc. No. ALZ01608348-356, filed Jun. 7, 2013, 10 pages.
"Exhibit T—U.S. Appl. No. 10/639,355: Reply Pursuant to 37 CFR §1.111", In the United States Patent and Trademark Office, Produced in Case No. 12-cv-04579, Doc. No. ALZ01169561-565, filed Mar. 20, 2009, 6 pages.
"Exhibit TT—U.S. Appl. No. 12/581,699: NonFinal Office Acton", In the United States Patent and Trademark Office, Doc. No. ALZ01608358-363, dated Jul. 3, 2013, 7 pages.
"Exhibit U—U.S. Appl. No. 10/639,355: Reply Pursuant to 37 CFR §1.114", In the United States Patent and Trademark Office, Produced in Case No. 12-cv-04579, Doc. No. ALZ01169579-585, filed Oct. 15, 2009, 8 pages.
"Exhibit UU—Leong et al., Advanced Drug Delivery Reviews", Elsevier, 1988, 1(3), 37 pages.

(56) References Cited

OTHER PUBLICATIONS

"Exhibit V—U.S. Appl. No. 10/639,355: Reply Pursuant to 37 CFR § 1.111", In the United States Patent and Trademark Office, Produced in Case No. 12-cv-04579, Doc. No. ALZ01169608-612, filed Jan. 7, 2010, 6 pages.
"Exhibit VV—Martin et al., Physical Pharmacy, Physical Chemical Principles in Pharmaceutical Sciences: Chapter 19—Drug Product Design", Lea and Febiger, $4^{th}$ Edition, 1993, 10 pages.
"Exhibit W—U.S. Appl. No. 10/639,355: Reply Pursuant to 37 CFR § 1.116", In the United States Patent and Trademark Office, Produced in Case No. 12-cv-04579, Doc. Nos. ALZ01169789-791, ALZ01169794-796, filed Jul. 29, 2010, 7 pages.
"Exhibit WW—Ranade et al., Drug Delivery Systems: Chapter 5, Oral Drug Delivery", CRC Press, 1995, 50 pages.
"Exhibit X—U.S. Patent No. 6,919,373 B1", In the United States Patent and Trademark Office, Doc. No. OSM(MET)015525-542, dated Jul. 19, 2005, 19 pages.
"Exhibit XX—Abdou, Remington's Pharmaceutical Sciences: Chapter 31—Dissolution", Mack Publishing Company, $18^{th}$ Edition, 1990, 18 pages.
"Exhibit Y—U.S. Appl. No. 09/253,317: Reply Pursuant to 37 CFR § 1.116", In the United States Patent and Trademark Office, Doc. Nos. OSM(MET)016709-711, OSM(MET)016737-739, filed Aug. 4, 2003, 7 pages.
"Exhibit YY—Longer et al., Remington's Pharmaceutical Sciences: Chapter 91—Sustained-Release Drug Delivery Systems", Mack Publishing Company, $18^{th}$ Edition, 1990, 22 pages.
"Exhibit Z—U.S. Patent No. 6,930,129 B2", In the United States Patent and Trademark Office, Doc. No. OSM(MET)016849-865, dated Aug. 16, 2005, 18 pages.
"Exhibit ZZ—Final Report—Protocol C-94-007-01: Pilot Study to Determine-the Effects of Three Patterns of Methylphenidate Delivery on Attention and Behavior in Children with ADHD", Alza Corporation, Doc. No. ALZ00098901-9131, May 1995, 232 pages.
"Gualtieri et al., Clinical Correlates of Methylphenidate Blood Levels, Therapeutic Drug Monitoring, 1984, 6, 379-392", In the United States District Court for the Northern District of California, Oakland Division, Case No. 4:12-cv-04579-PJH, Doc. No. 114-2, filed Dec. 13, 2013, 15 pages.
"Highly Confidential—Deposition of Carol a Christopher, Ph.D. taken on Behalf of Defendants", In the United States District Court for the District of Delaware, Case No. 10-23-LPS (1:10-cv-00023-LPS), ALZ01177314-7457, Mar. 7, 2011, 144 pages.
"Highly Confidential—Under Protechtive Order—Deposition of Andrew C. Lam on Behalf of Defendants", In the United States District Court for the District of Delaware, Case No. 1:05-cv-00642-JJF, ALZ00932488-2542, dated Sep. 20, 2006, 55 pages.
"Memorandum and Order Granting Plaintiff's Motion to Dismiss the InEquitable Conduct Counterclaims", In the United States District Court for the District of Delaware, Case No. 1:13-1104-RGA (Consolidated), Doc. No. 139, filed May 27, 2014, 3 pages.
"Minutes Sep. 20, 1993-Sep. 22, 1993 Multimodal Treatment Study of Children with Adhd (MTA) Steering Committee, Twelfth Meeting", In the United States District Court for the Northern District of California, Oakland Division, Case No. 4:12-cv-04579-PJH, Doc. No. 114-8, dated Dec. 13, 2013, 37 pages.
"Modi et al., Dose-Proportional and Stereospecific Pharmacokinetics of Methylphenidate Delivered Using an Osmotic, Controlled-Release Oral Delivery System, Journal of Clinical Pharmacology, 2000, 40, 1141-1149", In the United States District Court for the Northern District of California, Oakland Division, Case No. 4:12-cv-04579-PJH, Doc. No. 115-2, dated Dec. 13, 2013, 10 pages.
"Modi et al., Single- and Multiple-Dose Pharmacokinetics of an Oral Once-a-Day Osmotic Controlled-Release Oros® (methylphenidate HCI) Formulation, Journal of Clinical Pharmacology, 2000, 40, 379-388", In the United States District Court for the Northern District of California, Oakland Division, Case No. 4:12-cv-04579-PJH, Doc. No. 115-7, dated Dec. 13, 2013, 10 pages.
"Patrick et al., the Absorption of Sustained-Release Methylphenidate Formulations Formulation Compared to an Immediate-Release, Biopharmaceutics and Drug Disposition, 1989, 10, 165-171", In the United States District Court for the Northern District of California, Oakland Division, Case No. 4:12-cv-04579-PJH, Doc. No. 114-1, dated Dec. 13, 2013, 7 pages.
"Physicians' Desk Reference, PDR", Medical Economics Data Production Co., 49th Edition, 1995, 15 pages.
"Physicians' Desk Reference, PDR", Medical Economics Data Production Co., 1996, 2 pages.
"Plaintiff Swanson's Complaint for Correction of Inventorship, Fraud, Breach of Fiduciary Duty, Unjust Enrichment, Invalidity, and Declaration of Unenforceability for Inequitable Conduct in Patent Procurement", In the United States District Court for the Northern District of California, San Fransico Division, Case No. 12-cv-04579, Doc. No. 1, E-Filing, filed Aug. 30, 2012, 15 pages.
"Plaintiff Swanson's First Amended Complaint for Correction of Inventorship, Fraud, Breach of Fiduciary Duty, Fraudulent Concealment, Unfair Competition, Unjust Enrichment, Invalidity, Declaration of Unenforceability for Inequitable Conduct in Patent Procurement, Declaration of Ownership and Constructive Trust", In the United States District Court for the Northern District of California, Oakland Division, Case No. 4:12-cv-04579-PJH, Doc. No. 31, filed Nov. 14, 2012, 54 pages.
"Plaintiff Swanson's Inventorship Contentions", In the United States District Court for the Northern District of California, Oakland Division, Case No. 4:12-cv-04579-PJH, Doc. No. 115-8, filed Dec. 13, 2013, 272 pages.
"Plaintiff Swanson's Inventorship Contentions", In the United States District Court for the Northern District of California, Oakland Division, Case No. 4:12-cv-04579-PJH, Doc. No. 115-9, filed Dec. 13, 2013, 56 pages.
"Plaintiff Swanson's Inventorship Contentions", In the United States District Court for the Northern District of California, Oakland Division, Case No. 4:12-cv-04579-PJH, Doc. No. 115-10, filed Dec. 13, 2013, 96 pages.
"Plaintiffs' Reply Brief in Support of Motion to Strike Defenses and Dismiss Counterclaims Alleging Inequitable Conduct", In the United States District Court for the District of Delaware, C.A. No. 13-1104-RGA (Consolidated), filed May 8, 2014, 10 pages.
"Plaintiffs' Motion to Strike Defenses and Dismiss Counterclaims Alleging Inequitable Conduct", In the United States District Court for the District of Delaware, C.A. No. 13-1104-RGA (Consolidated), filed Apr. 11, 2014, 4 pages.
"Plaintiffs' Opening Brief in Support of Motion to Strike Defenses and Dismiss Counterclaims Alleging Inequitable Conduct", In the United States District Court for the District of Delaware, C.A. No. 13-1104-RGA (Consolidated), filed Apr. 11, 2014, 18 pages.
"PX3—Certified Copy of U.S. Appl. No. 60/030,514", In the United States Patent and Trademark Office, dated Sep. 18, 2007, 84 pages.
"PX4—Certified Copy of U.S. Appl. No. 60/031,741", In the United States Patent and Trademark Office, dated Sep. 18, 2007, 82 pages.
"PX5—Certified Copy of U.S. Appl. No. 60/044,121", In the United States Patent and Trademark Office, dated Sep. 15, 2007, 83 pages.
"PX6—Certified Copy of U.S. Appl. No. 08/910,593", In the United States Patent and Trademark Office, dated Sep. 18, 2007, 745 pages.
"PX9—Certified Copy of U.S. Patent Application No. 09/070,666", In the United States Patent and Trademark Office, dated Oct. 5, 2007, 782 pages.
"Redacted Plaintiffs' Responses and Objections to Defendant Par Pharmaceutical, Inc.'s and Defendant Osmotica Kereskedelmi Es Szolgaltato Kft's First Set of Joint Rule 33 Interrogatories (Nos. 1-10)", In The United States District Court for the District of Delaware, C.A. No. 13-1104-RGA (Consolidated), filed Dec. 2, 2013, 25 pages.
"Redacted Public Version Jury Demanded—Defendants Osmotica Kereskedelmi Es Szolgaltato Kft's and Osmotica Pharmaceutical Corp.'s Answer, Defenses, and Counterclaims to Plaintiffs' Complaint", In the United States District Court for the District of Delaware, Case No. 1:13-cv-01126 (RGA), Doc. No. 22, filed Sep. 16, 2013, 92 pages.
"Ritalin (Methylphenidate Hydrochloride", FDA Drugs Approvals and Database, 2014, 5 pages.

(56) References Cited

OTHER PUBLICATIONS

"Ritalin Hydrochloride Methylphenidate Hydrochloride Tablets USP and Ritalin-SR Methylphenidate Hydrochloride USP Sustained-Release Tablets", Novartis, T2007-23, Apr. 2007, 41 pages.
"Ritalin LA (Methylphenidate Hydrochloride) Extended-Release Capsules", Novartis, 2012, 22 pages.
"Ritalin-SR", FDA Drugs Approvals and Database, 2014, 2 pages.
"Seeman, Pharmacokinetics, 1 page", In the United States District Court for the Northern District of California, Oakland Division, Case No. 4:12-cv-04579-PJH, Doc. No. 114-10, dated Dec. 13, 2013, 1 page.
"Sprague, Methylphenidate in Hyperkinetic Children: Differences in Dose Effects on Learning and Social Behavior, Science, 1977, 198, 1274-1276", In the United States District Court for the Northern District of California, Oakland Division, Case No. 4:12-cv-04579-PJH, Doc. No. 114-13, dated Dec. 13, 2013, 3 pages.
"Swanson et al., Blood Levels and Tolerance to Stimulants in ADDH Children, Clinical Neuropharmacology, 1986, 9(Suppl-4), S-215, 523-525", In the United States District Court for the Northern District of California, Oakland Division, Case No. 4:12-cv-04579-PJH, Doc. No. 114-5, filed Dec. 13, 2013, 3 pages.
"Swanson et al., Effects of Stimulant Medication on Learning in Children with ADHD, Journal of Learning Disabilities, Apr. 1991, 24(4), 14 pp.", In the United States District Court for the Northern District of California, Oakland Division, Case No. 4:12-cv-04579-PJH, Doc. No. 114-4, filed Dec. 13, 2013, 14 pages.
"Swanson et al., Intervention Strategies with Hyperactive Children: Task Specificity of Responses to Stimulant Drugs in Laboratory Tests", Gittleman (Ed.), Int'l Journal of Mental.Health, 1979, 8(1), 18 pages, In the United States District Court for the Northern District of California, Oakland Division, Case No. 4:12-cv-04579-PJH, Doc. No. 115, filed Dec. 13, 2013, 18 pages.
"Swanson et al., Serum Levels of Nethylphenidate in Hyper.active Children: 1. Half-life Following Oral Administration", In the United States District Court for the Northern District of California, Oakland Division, Case No. 4:12-cv-04579-PJH, Doc. No. 114-12, filed Dec. 13, 2013, 21 pages.
"Swanson, Effects of Stimulant Medication on Children with Attention Deficit Hyperactive Disorder: A Review of Reviews, Council for Exceptional Children, Oct. 1, 1993, 60(2), 9 pages", In the United States District Court for the Northern District of California, Oakland Division, Case No. 4:12-cv-04579-PJH, Doc. No. 114-7, filed Dec. 13, 2013, 9 pages.
"Swanson, Measurement of Serum Concentrations and Behavioral Response in ADDH Children to Acute Doses of Methylphenidate, 1988, 21 pages", In the United States District Court for the Northern District of California, Oakland Division, Case No. 4:12-cv-04579-PJH, Doc. No. 114-3, filed Dec. 13, 2013, 21 pages.
"Swanson, More Frequent Diagnosis of Attention Deficit-Hyperactivity Disorder, The New England Journal of Medicine, Oct. 5, 1995, 333(14), 1 page", In the United States District Court for the Northern District of California, Oakland Division, Case No. 4:12-cv-04579-PJH, Doc. No. 114-6, filed Dec. 13, 2013, 1 page.
Brown et al., "Attention Deficit Hyperactivity Disorder", Produced in 12-CV-04579, ALZ00016282-293, CNS Drugs, 1994, 1(2), 70-81.
Brown, "The Use of Methylphenidate for Cognitive Decline Associated with HIV Disease", Int'l J. Psychiatry in Medicine, 1995, 25(1), 21-37.
Chisum, "Chisum on Patents: A Treatise on the Law of Patentability, Validity and Infringement, vol. 1, Originality-Inventorship §2.03", Matthew Bender and Company, Inc., 2013, 36 pages.
Diener, "Ritalin Theory and Patient Management: Toxicology of Ritalin", Produced in 12-CV-04579, ALZ01109117-9118, Greenhill et al. (Eds.), Mary Ann Liebert, Inc., 1991, 11 pages.
Dulcan, "Using Psychostimulants to Treat Behavioral Disorders of Children and Adolescents", Produced in 12-CV-04579, PALZ007750-7763, Journal of Child and Adolescent Psychopharmacology, 1(1), 1990, 7-20.

Endicott et al., "Quality of Life Enjoyment and Satisfaction Questionnaire: A New Measure", Produced in 12-CV-04579, ALZ00015604-5609, Psychopharmacology Bulletin, 1993, 29(2), 321-326.
Fung, "Pharmacokinetic Determinants of Nitrate Action", The American Journal of Medicine, Proceedings of a Symposium, $2^{nd}$ North American Conference on Nitroglycering Therapy, Perspectives and Mechanisms, DTX288, Jun. 22, 1984, 76(6A), 6 pages.
Gill et al., "Immediate Communication: Confirmation of Association Between Attention Deficit Hyperactivity Disorder and a Dopamme Transporter Polymorphism", Produced in 12-CV-04579, ALZ00015657-5659, Molecular Psychiatry, 1997, 2, 311-313.
Greenhill, "Child and Adolescent Psychiatric Clinics of North America: Attention-Deficit Hyperactivity Disorders, the Stimulants", Produced in 12-CV-04579, ALZ00014659-4705, W.B. Saunders Co., Jan. 1995, 4(1), 47 pages.
Greenhill, "Strategic Interventions for Hyperactive Children: Stimulant-Related Growth Inhibition in Children: A Review", Gittelman (Ed.), M.E. Sharpe, Inc., 1979 and 1981, 27 pages.
Holmes et al., "Psychostimulant Response in AIDS•Related Complex Patients", J. Clin. Psychiatry, 1989, 50, 5-8.
Letter from Ashby and Geddes, "Redacted Plaintiffs' Responsive Discovery Dispute Letter", Feb. 14, 2014, 5 pages.
Letter from Mylan Pharmaceuticals, "Notification of Paragraph IV Certification Regarding U.S. Patent Nos. 6,919,373, 6,930,129, 8,163, 798, and 8,629,179 Pursuant to Section 505 G)(2)(B)(i)-(ii) of the Federal Food, Drug, and Cosmetic Act", Apr. 1, 2014, 122 pages.
Letter from Osmotica, "Methylphenidate Hydrochloride Extended Release Tablets, 54 mg: Notification of Certification of Invalidity, Unenforceability and/or Noninfringement for U.S. Patent No. 8,629,179 Pursuant to § 505U)(2)(B)(iv) of the Federal Food, Drug, and Cosmetic Act", Jan. 14, 2014, 84 pages.
Letter from Osmotica, "Methylphenidate Hydrochloride Extended Release Tablets, 54 mg: Notification of Certification of Invalidity, Unenforceability and/or Noninfringement for U.S. Patent Nos. 6,919,373 B1, 6,930,129 B2, and 8,163,798 B2 Pursuant to § 505G)(2)(B)(iv) of the Federal Food, Drug, and Cosmetic Act", May 17, 2013, 30 pages.
Letter from Osmotica, "Methylphenidate Hydrochloride Extended-Release Tablets, 18 mg, 27mg and 36 mg: Notification of Certification of Invalidity, Unenforceability and/or Noninfringement for U.S. Patent Nos. 6,919,373, 6,930,129, 8,163,798, and 8,629,179 Pursuant to § SOS(j)(2)(B)(iv) of the Federal Food, Drug, and Cosmetic Act", Apr. 29, 2014, 83 pages.
Letter from Par Pharmaceuticals, "Methylphenidate Hydrochloride Extended Release Tablets for Oral Administration (18 mg, 27 mg, 36 mg, and 54 mg) U.S. Patent No. 8,629,179, Notice of Paragraph IV Certification", Feb. 25, 2014, 21 pages.
Letter from Par Pharmaceuticals, "Methylphenidate Hydrochloride Extended Release Tablets for Oral Administration (18 mg, 27 mg, 36 mg, and 54 mg) U.S. Patent Nos. 6,919,373, 6,930,129, and 8,163,798, Notice of Paragraph IV Certification", May 6, 2013, 38 pages.
Letter from Sandoz, "Notice of Certification Under 21 U.S.C. § 355(j)(2)(B) (§ 505(j)(2)(B)) of Federal Food, Drug and Cosmetic Act) and 21 C.F.R. § 314.95 Sandoz Inc.'s Methylphenidate HCI, Tablet, Extended Release 54 mg, Sandoz Inc.'s ANDA 205714", May 5, 2014, 39 pages.
Letter from Sun Pharmaceuticals, "Notification Pursuant to the Federal Food, Drug, and Cosmetic Act (21 U.S.C. 355(j)(2)(B)(ii) and 21 C.F.R. § 314.95): ANDA No. 205135 and Concerta Methylphenidate Hydrochloride Extended Release Tablet", Mar. 19, 2014, 36 pages.
Longer et al., "Remington's Pharmaceutical Sciences: Chapter 91—Sustained-Release Drug Delivery Systems", Mack Publishing Company, 1990, $18^{th}$ Edition, 20 pages.
Parran et al., "Intravenous Methylphenidate Abuse: Prototype for Prescription Drug Abuse", Produced in 12-CV-04579, ALZ00016062-6064, Arch Intern Med., 1991, 151, 781-783.
Pere!, et al., "Correlates of Pharmacokinetics and Attentional Measures in Methylphenidate Treated Hyperactive Children", Produced in 12-CV-04579, ALZ00004759, Clinical Pharmacology and Therapeutics, 1991, 1 page.

(56) References Cited

OTHER PUBLICATIONS

Rapport et al., "Attention Deficit Hyperactivity Disorder and Methylphenidate: The Relationship Between Gross Body Weight and Drug Response in Children", Psychopharmacology Bulletin, National Institute of Mental Health, Special Feature: NCDEU Poster Summaries, 1989, 25(2), 8 pages.

Safer et al., "Absence of Tolerance to the Behavioral Effects of Methyiphenidate in Hyperactive and Inattentive Children", Pediatric Pharmacology and Therapeutics, Dec. 1989, 1003-1008.

Sannerud et al., "Ritalin Theory and Practice: Is Ritalin an Abused Drug? Does it Meet the Criteria of a Schedule II Substance?", Produced in 12-CV-04579, ALZ00005140-5157, $2^{nd}$ Edition, Greenhill et al. (Eds.), Mary Ann Liebert, Inc., 2000, 27 pages.

Solanto, "Neuropsychopharmacological Mechanisms of Stimulant Drug Action in Attention-Deficit Hyperactivity Disorder: A Review and Integration", Produced in 12-CV-04579, ALZ00005326-5351, Behavioural Brain Research, 1998, 94, 127-152.

Soldin et al., "A Liquid-Chromatographic Analysis for Ritalinic Acid [a-Phenyl-a(2-piperidyl) Acetic Acid] in Serum", Clinical Chemistry, 1979, 25(1), 5 pages.

Soldin et al., "Liquid-Chromatographic Analysis for Methylphenidate (Ritalin) in Serum", Clinical Chemistry, 1979, 25(3), 5 pages.

Spencer et al,. "A Double-blind, Crossover Comparison of Methylphenidate and Placebo in Adults with Childhood-Onset Attention-Deficit Hyperactivtty Disorder", Produced in 12-CV-04579, ALZ00015727-5736, Arch Gen Psychiatry, 1995, 52, 434-443.

Stevenson et al., "Stimulant Medication Therapy in the Treatment of Children with Attention Deficit Hyperactivity Disorder", Produced in 12-CV-04579, ALZ000162772-2786, Clinical Pharmacology, Pediatric Clinics of North America, Oct. 1989, 35(5), 1183-1197.

Swanson et al., "A Comparison of Once-Daily Extended-Release Methylphemdate Formulations in Children With Attention-Deficit/Hyperactivity Disorder in the Laboratory School (The Comacs Study)", Produced in Case No. 12-cv-04579, Doc. Nos. ALZ00004843-4853, Pediatrics, Mar. 2004, 113(3), 11 pages.

Swanson et al., "Pharmacokinetic and Pharmacodynamic Properties of Stimulants: Implications for the Design of New Treatments for ADHD", Produced in Case No. 12-cv-04579, Doc. Nos. ALZ00004837-4842, Behavioural Brain Research, 2002, 130, 73-78.

Swanson et al., "Should You Use Stimulants to Treat the Hyperactive Child?", Modern Medicine, Apr. 15, 1978, 11 pages.

Swanson et al., "Time-Response Analysis of the Effect of Stimulant Medication on the Learning Ability of Children Referred for Hyperactivity", Pediatrics, Jan. 1978, 61(1), 9 pages.

Swanson, "Stimulant-Related State-Dependent Learning in Hyperactive Children", American Association for the Advancement of Science, Jun. 1976, 192(4246), 5 pages.

Teicher et al., "Locomotor Activity in Depressed Children and Adolescents: I. Circadian Dysregulation", Journal of the American Academy Child and Adolescent Psychiatry, Jul. 1993, 32(4), 11 pages.

Theeuwes et al., "Systems for Triggered, Pulsed, and Programmed Drug Delivery", 1991, 14 pages.

Theeuwes, "Novel Drug Delivery and its Therapeutic Application: Chapter 30. Triggered, Pulsed and Programmed Drug Delivery", Prescott et al. (Eds.), John Wiley and Sons, 1989, 20 pages.

Voeller, "Clinical Management of Attention Deficit Hyperactivity Disorder", Journal of Child Neurology, 1991, 6, 18 pages.

Volkow et al., "Dopamine Transporter Occupancies in the Human Brain Induced by Therapeutic Doses of Oral Methylphenidate", Produced in Case No. 12-cv-04579, Doc. Nos. ALZ00004887-4893, Am J Psychiatry, 1998, 155, 1325-1331.

Volkow et al., "Is Methylphenidate Like Cocaine? Studies on Their Phannacokinetics and Distribution in the Human Brain", Produced in Case No. 12-cv-04579, Doc. Nos. ALZ00005352-5359, Arch Gen Psychiatry, 1995, 52, 456-463.

Volkow et al., "Temporal Relationships Between the Pharmacoklrletics of Methylphenidate in the Human Brain and its Behavioral and Cardiovascular Effects", Produced in Case No. 12-cv-04579, Doc. Nos. ALZ00004894-4901, Psychopharmacology, 1996, 123, 26-33.

Volkow et al., "Variables That Affect the Clinical Use and Abuse of Methylphenidate in the Treatment of ADHD", Produced in 12-CV-04579, ALZ00004877-4886, Am J. Psychiatry, 2003, 160, 1909-1918.

Wigal et al., "Reliability and Validity of the SKAMP at ng Scale in a Laboratory School Setting", Produced in Case No. 12-cv-04579, Doc. Nos. ALZ00004902-4908, Psychopharmacology Bulletin, 1998, 34(1), 47-53.

Wigal et al., "Reliability and Validity of the SKAMP at ng Scale in a Laboratory School Setting", Produced in Case No. 12-cv-04579, Doc. Nos. ALZ00021227-33, Psychopharmacology Bulletin, 1998, 34(1), 47-53.

*William T. Graham et al.* v. *John Deere Co. of Kansas City* v. *Cook Chemical and Colgate-Palmolive Co., et al.*, Nos. 11, 37, 43, 86 S.Ct. 684, 383 U.S. 101, 1966, 684-707.

METHODS AND DEVICES FOR PROVIDING PROLONGED DRUG THERAPY

CROSS-REFERENCE TO RELATED APPLICATIONS

This application is a divisional of U.S. Ser. No. 10/638,977, filed Aug. 12, 2003, which is a continuation of U.S. Ser. No. 09/802,709, filed Mar. 8, 2001; which is a continuation of U.S. Ser. No. 09/253,317, filed Feb. 19, 1999; which is a continuation-in-part of U.S. Ser. No. 09/070,666, filed Apr. 30, 1998; which is a continuation of U.S. Ser. No. 08/910,593, filed Jul. 31, 1997; which claims the benefit of U.S. Provisional App. Nos. 60/044,121 and 60/030,514, filed Apr. 22, 1997 and Nov. 12, 1996, respectively. U.S. Ser. No. 09/253,317 is also a continuation-in-part of Ser. No. 08/967,606, filed Nov. 10, 1997; which claims the benefit of U.S. Provisional App. No. 60/031,741, filed Nov. 25, 1996. U.S. application Ser. No. 09/253,317 is also a continuation-in-part of Ser. No. 08/937,336, filed Aug. 19, 1997.

All applications above are incorporated by reference in their entirety herein.

BACKGROUND

1. Field of the Invention

This invention pertains to methods and devices for maintaining a desired therapeutic drug effect over a prolonged therapy period. In particular, the invention is directed to methods and devices that provide drug release within the gastrointestinal tract at an ascending release rate over an extended time period. In this manner, drug is released at an ascending rate during a portion of the drug administration period sufficient to maintain a desired therapeutic drug effect throughout a prolonged therapy period.

2. Description of the Related Art

To produce its pharmacological effects, a drug must be made available in appropriate concentrations at its site of action within the body. This availability is affected by numerous factors including the quantity of the drug administered, the extent and rate of its absorption from its administration site, its distribution, binding or localization within tissues, its biotransformation and its excretion. One commonly-used indicator of drug availability is the concentration of drug that is obtained within the blood or plasma, or other appropriate body fluid or tissue, of a patient following administration of the drug. For convenience, this concentration may be referred to as "plasma drug concentration" hereinafter which is intended to be inclusive of drug concentration measured in any appropriate body fluid or tissue. Plasma drug concentration measurements provide very useful information including, for example, comparative information with regard to different drug dosage forms and/or different drug administration routes. In addition, for many drugs, various drug effects including both desired pharmacological effects, i.e., therapeutic drug effects, and undesired pharmacological effects, i.e., side effects, have been correlated with specific plasma drug concentrations or ranges of plasma drug concentrations.

For orally administered drug dosage forms, absorption occurs within the gastrointestinal ("g.i.") tract and is affected by many factors including the physicochemical properties of the local microenvironment, such as surface area, blood flow and membrane characteristics (which vary significantly in the different portions of the g.i. tract), the physicochemical properties of the drug entity, drug concentration, the existence and activity of drug-specific transport mechanisms, etc. One important factor in the rate of absorption of drug administered as an oral dosage form is the rate at which drug is released from the dosage form. Drug release rates for oral dosage forms are typically measured as an in vitro rate of dissolution, i.e., a quantity of drug released from the dosage form per unit time.

Conventional oral dosage forms can be described as "immediate-release" because, generally, essentially the entire dose of drug is released from the dosage form within a very short period, i.e., minutes, following administration. As this bolus of released drug is absorbed, the plasma drug concentration typically rapidly rises to a maximal or peak concentration and subsequently declines as the drug is distributed, bound or localized within tissues, biotransformed and/or excreted. The time period for this decline varies for different drugs and depends on many factors but this time period will be characteristic of a particular drug. Generally, during some portion of the time period in which the plasma drug concentration rises, peaks and declines, the drug provides its therapeutic effects, i.e., the plasma drug concentration achieves or exceeds an effective concentration. Moreover, at some point during this time period, the therapeutic effects disappear, i.e., when the plasma drug concentration declines to a level that is below an effective concentration. In addition, often, during a portion of this time surrounding the time the peak concentration is attained, i.e., when the plasma drug concentration is in its highest range, undesired side effects may become apparent.

In view of the above, it will be appreciated that continued drug effectiveness occurs during the time period when the plasma drug concentration is within the effective plasma drug concentration range. Because the plasma drug concentration declines over time, however, multiple doses of the immediate-release drug dosage form must be administered at appropriate intervals to ensure that the plasma drug concentration remains in or, again, rises to, the effective concentration range. At the same time, however, there is a need to avoid or minimize plasma drug concentrations that rise to, and/or that remain for too long within, the higher ranges where side effects become apparent. Accordingly, for many drugs, multiple, separate doses of the immediate-release dosage form must be administered at appropriate intervals to maintain a satisfactory balance of desired and undesired pharmacological effects over a prolonged therapy period.

One focus of efforts to improve drug therapy has been directed to providing non-immediate-release oral drug dosage forms that affect absorption of the drug primarily by altering the release rate of the drug from the dosage form. Examples of such non-immediate-release delivery systems include delayed-release and sustained-release systems. Sustained-release dosage forms generally release drug for an extended time period compared to an immediate-release dosage form. There are many approaches to achieving sustained release of drugs from oral dosage forms known in the art. These different approaches include, for example, diffusion systems such as reservoir devices and matrix devices, dissolution systems such as encapsulated dissolution systems (including, for example, "tiny time pills") and matrix dissolution systems, combination diffusion/dissolution systems, osmotic systems and ion-exchange resin systems as described in *Remington's Pharmaceutical Sciences,* 1990 ed., pp. 1682-1685.

It is believed to be particularly desirable to provide sustained-release oral dosage forms that provide drug release at a substantially constant release rate over an extended time period. In this manner, for many drugs, the plasma drug concentration initially ascends for a short period of time as drug release begins and then remains substantially constant over an extended time period as drug release continues at a constant rate. For many drugs, this substantially constant plasma drug concentration correlates with substantially constant drug effectiveness over a prolonged therapy period. In addition, because an initial relatively high peak plasma drug concentration is avoided, side effects may be less of a problem. Accordingly, advantages of constant-release dosage forms include decreasing the number of doses of a drug that need to be administered over time and providing a better balance of desired and undesired pharmacological effects of the drug.

Osmotic dosage forms, in particular, have been notably successful at providing constant-release of drugs over extended time periods. Osmotic dosage forms, in general, utilize osmotic pressure to generate a driving force for imbibing fluid into a compartment formed, at least in part, by a semipermeable wall that permits free diffusion of fluid but not drug or osmotic agent(s), if present. A substantially constant rate of drug release can be achieved by designing the system to provide a relatively constant osmotic pressure and having suitable exit means for the drug formulation to permit the drug formulation to be released at a rate that corresponds to the rate of fluid imbibed as a result of the relatively constant osmotic pressure. A significant advantage to osmotic systems is that operation is pH-independent and thus continues at the osmotically-determined rate throughout an extended time period even as the dosage form transits the gastrointestinal tract and encounters differing microenvironments having significantly different pH values.

Surprisingly simple but highly effective osmotic devices comprising drug in a mixture with excipients, optionally including osmotically active component(s), within the compartment are known in the art. Although effective for many drugs, the release rate in these devices often declines over time and complete delivery of the drug load may not occur. A more sophisticated type of osmotic device comprises two component layers within the compartment formed by the semipermeable wall. One component layer comprises drug in a mixture with excipients, optionally including osmotically active component(s), that will form a deliverable drug formulation within the compartment and the second component layer comprises osmotically active component(s) but does not contain drug. The osmotically active component(s) in the second component layer typically comprise osmopolymer(s) having relatively large molecular weights and which exhibit "swelling" as fluid is imbibed such that release of these components through the drug formulation exit means does not occur. The second component layer is referred to as a "push" layer since, as fluid is imbibed, the osmopolymer(s) swell and push against the deliverable drug formulation of the first component layer to thereby facilitate release of the drug formulation at a substantially constant rate. The above-described devices are known, for example, from the following US patents, owned by Alza Corporation: U.S. Pat. Nos. 4,327,725; 4,612,008; 4,783,337; and 5,082,668, each of which is incorporated in its entirety by reference herein.

Although constant-release dosage forms have proven effective for many different drug therapies, there are clinical situations where these have not been entirely satisfactory. It has been observed that for some patients being treated with constant-release dosage forms for some conditions or diseases, the therapeutic effectiveness of the drug decreases at time periods before the end of the desired therapy period despite the maintenance of substantially constant drug release that would be expected to provide continued effectiveness. Accordingly, there remains a need to provide methods and devices for maintaining a desired therapeutic drug effect over a desired prolonged therapy period when sustained-release dosage forms that release drug at a substantially constant rate over an extended time period are not satisfactory.

BRIEF SUMMARY OF THE INVENTION

One aspect of the present invention pertains to providing improved drug therapy for those clinical situations where therapeutic effectiveness of an administered drug therapy unexpectedly decreases at time periods before the end of the intended therapy period. It has been surprisingly discovered that, in an exemplary clinical situation, administration of drug at a release rate that is ascending, rather than substantially constant, over an extended time period provided therapeutic efficacy that did not decrease before the end of the prolonged therapy period.

With the discovery that administration of drug at a release rate that is substantially ascending provides improved drug therapy, a need arises for sustained-release oral dosage forms adapted to provide such a release rate over a suitable extended time period. Accordingly, other aspects of the present invention include providing oral sustained-release dosage forms that provide an ascending drug release rate over an extended time period, methods of making such dosage forms and methods of using such dosage forms to maintain therapeutic effectiveness for a desired prolonged therapy period.

It has been surprisingly discovered that oral osmotic dosage forms exhibiting an ascending drug release rate for an extended time period can be achieved. In particular, the present invention is directed to osmotic dosage forms having bi-layer or tri-layer tablet cores that are adapted to provide ascending drug release rates over an extended period. In addition, to provide for an initial rapid onset of drug action, the present invention is also related to dosage forms that additionally comprise a dose of drug for immediate release.

The bi-layer oral osmotic dosage forms of the present invention include a first component layer, comprising a selected drug and excipients for forming a deliverable drug composition when hydrated, and a second push layer, comprising a fluid-expandable osmopolymer and excipients, contained within a compartment formed by a semipermeable membrane and having exit means for drug release from the compartment. The two layers are compressed into bi-layer tablet cores before the semipermeable membrane is applied and a suitable orifice for drug release therethrough is formed. Importantly, the bi-layer tablet cores disclosed herein are formed when two component layers are compressed together to provide a longitudinally compressed tablet ("LCT") core having a "capsule-shaped" configuration with a different layer at each narrow end.

The combination of features including the osmotic properties of the component layers, the fluid flux properties of the semipermeable membrane and the configuration of the tablet core ensures that drug is released at an ascending rate over an extended time period. In a preferred embodiment, sufficient activity in the push layer is achieved by use of a relatively large concentration (at least about 35%) of osmotically effective solute, or osmagent, such as sodium chloride. In addition, sorbitol is preferably included in the first component layer.

The tri-layer oral osmotic dosage forms of the present invention include a novel tri-layer tablet core surrounded by a semipermeable membrane and having suitable exit means for releasing drug formulation through the semipermeable membrane. The novel tri-layer tablet core has a first drug-containing layer, a second drug-containing layer and a third push layer. In operation, through the cooperation of the dosage form components, drug is successively released from the first drug-containing layer and then from the second drug-containing layer. It has been discovered that a drug concentration gradient facilitates the achievement of an ascending drug release rate for an extended time period. Consequently, the other excipients in the drug-containing layers may be more flexibly varied and adjusted for other purposes such as manufacturing convenience and pharmaceutical elegance. In this manner, dosage forms that exhibit reliable drug release having the desired sustained and ascending rate over an extended time period can be reliably and efficiently manufactured.

It is preferred to use the LCT core configuration, as described above, to enhance hydration of the tri-layer core. In addition, a flux-enhancing agent is preferably included in the semipermeable wall composition. In a presently preferred embodiment, the combination of features including the LCT tri-layer core configuration, a suitable drug concentration gradient between the first and second component layers, the osmotic properties of the component layers and the fluid flux properties of the semipermeable membrane achieves the desired ascending rate of drug release over an extended time period.

There are numerous clinical situations and drug therapies that could be improved with the use of dosage forms that provide a sustained and ascending release rate over an extended time period. Exemplary dosage forms, as disclosed herein, comprise CNS-acting drugs and cardiovascular-acting drugs. It will be appreciated by persons of skill in the art that the invention is applicable to many other types of drugs and drug therapies. Examples of suitable types of drugs include, but are not limited to, anti-infectives, analgesics, anesthetics, antiarthritics, antiasthmatics, anticonvulsants, antidepressants, antidiabetics, antidiarrheals, antihistamines, antiinflammatories, antimigraines, antineoplastics, antiparkinsonisms, antipruritics, antipsychotics, antipyretics, antispasmodics, anticholinergics, sympathomimetics, calcium channel blockers, beta blockers, antiarrythmics, antihypertensives, ACE inhibitors, diuretics, vasodilators, decongestants, hormones, hypnotics, immunosuppresives, parasympathomimetics, prostaglandins, proteins, peptides, sedatives and tranquilizers.

The exemplary clinical situation described herein involves treatment of ADHD with methylphenidate therapy. Accordingly, the present invention also pertains to making oral methylphenidate sustained release dosage forms that provide a sustained and ascending release rate of a drug over an extended time period.

It has further been discovered that oral methylphenidate sustained release dosage forms that provide an ascending release rate of a drug over an extended time period can be used to provide effective once-a-day therapy for ADHD. Thus, the present invention also pertains to improving drug therapy for ADHD by eliminating the need for multiple daily doses of methylphenidate yet providing therapeutic efficacy throughout the day that compares to the therapeutic efficacy provided by multiple doses of immediate release methylphenidate.

The above-described features and advantages, as well as others, will become more apparent from the following detailed disclosure of the invention and the accompanying claims.

Although the present invention is illustrated herein by exemplary dosage forms containing specific exemplary drugs, methods of making such dosage forms and methods of using methylphenidate-containing dosage forms to provide a desired therapeutic outcome, the invention is not limited by the exemplary embodiments. The invention broadly embraces oral sustained-release dosage forms that provide an ascending drug release rate over an extended time period, methods of making such dosage forms and methods of using such dosage forms to maintain therapeutic effectiveness for a desired prolonged therapy period with respect to any appropriate drugs and drug therapies as would be apparent to a person of skill in the art in view of the disclosure herein.

DETAILED DESCRIPTION OF THE INVENTION

Figure 1:
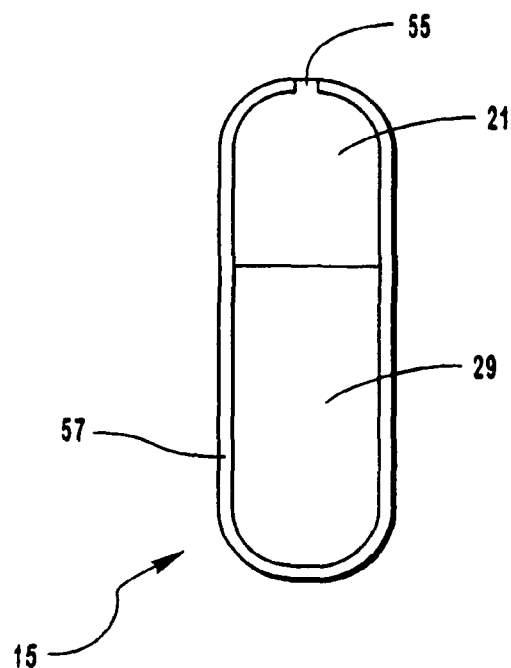
FIG. 1 is a cross-section view of a bi-layer osmotic dosage form in accord with the present invention.

Many effective drug therapies utilize immediate-release oral dosage forms administered at spaced intervals to provide and maintain a desired therapeutic effect over a prolonged therapy period. In addition, sustained-release dosage forms for many drugs are known and, in particular, constant-release oral dosage forms are known. There are many examples of effective drug therapies that utilize constant-release oral dosage forms to provide a desired therapeutic effect over a prolonged therapy period. In many cases, these drug therapies offer advantages over drug therapies that utilize immediate-release oral dosage forms administered at spaced intervals. There are clinical situations, however, where the constant-release dosage form has unexpectedly exhibited decreases in therapeutic effectiveness at time periods before the end of the desired prolonged therapy period.

One example of a clinical situation where drug therapy with sustained-release oral drug dosage forms that provide a substantially constant rate of drug release for an extended period has not been entirely satisfactory is with the use of central nervous system (CNS) stimulant drugs to treat various conditions and disorders including Attention Deficit Disorder (ADD) and Attention Deficit Hyperactivity Disorder (ADHD). These disorders are commonly diagnosed in children but can also occur in adults. Treatment of these and other psychological conditions with CNS stimulant drugs has a long history. About 25 years ago, methylphenidate replaced amphetamine as the primary stimulant prescribed to treat ADHD in children.

Methylphenidate therapy in children with ADHD has been extensively studied and the efficacy and safety of this treatment is well-established. Methylphenidate therapy has been shown to be very effective in reducing symptoms of hyperactivity, inattention and impulsivity in children with ADHD. The goal of drug therapy is to control the behavioral symptoms during the daytime while the patient is in school or otherwise involved in activities where symptom control benefits the patient's ability to learn and/or otherwise beneficially participate in activities. Because of concerns related to side effects, however, drug therapy is typically discontinued during at least a portion of the evening and through the night in most patients. Depending on the patient's particular circumstances, drug therapy may or may not be discontinued over the weekends as well.

Treatment commonly utilizes immediate-release methylphenidate administered two or three times during the day. For various reasons, patients often experience difficulty complying with this administration schedule. Because of abuse potential, methylphenidate is a controlled substance and thus drug access is a special concern. This dosage regimen generally requires that at least one dose is administered during the school day and, as a rule, children are not permitted to self-administer the drug at school. For this reason, authorized school personnel generally take on the responsibility for administering the drug to children during the school day, however, this approach raises issues of medical privacy and potential stigmatizing of the child by peers. In addition, the compliance issue becomes further complicated as transportation, storage and supply of the drug typically must be documented and/or monitored and the schedules of the different parties involved, i.e., the child, the educators and the authorized school personnel, must be coordinated and accommodated. The unfortunate result is that doses may be given late or missed altogether resulting in decreased efficacy of the therapy.

For all of the above reasons, it would appear that a sustained-release oral dosage form of methylphenidate that provided substantially constant drug release over an extended period to thereby eliminate the need for dose administration during the school day would be a welcome improvement. In fact, such a sustained-release dosage form of methylphenidate has been commercially available for several years. Clinical experience with this dosage form, however, has been disappointing in that behavioral symptoms in patients taking the controlled-release dosage form is less well-controlled later in the day compared to those patients taking multiple doses of the immediate-release dosage form. In addition, the slower onset of action of the controlled-release dosage form compared to the immediate-release dosage form is unsatisfactory for many patients.

It has been surprisingly discovered that administration of methylphenidate at a release rate that is substantially ascending, rather than substantially constant, over an extended time period provided therapeutic efficacy similar to the efficacy obtained with multiple doses of immediate-release methylphenidate dosage forms. Details of this discovery are disclosed in copending U.S. application Ser. No. 910,593, filed Jul. 31, 1997, of which the present application is a continuation-in-part application. To briefly review, in one clinical study, a comparison of the behavioral, attentional, and cognitive efficacy of placebo and methylphenidate administered according to three different release rate regimens, i.e., immediate-release, constant-release and ascending-release, was performed. The immediate-release methylphenidate was administered as two spaced-apart doses. The constant-release regimen was administered as an initial loading dose with the remaining total quantity administered in equal small doses at closely-spaced intervals extending past the time of administration of the second immediate-release dose. The ascending-release regimen was administered as an initial loading dose with the remaining total quantity administered in increasing small doses at closely-spaced intervals extending past the time of administration of the second immediate-release dose.

In this study, the constant-release regimen was observed to have decreased clinical effectiveness compared to the immediate-release regimen at evaluation periods following administration of the second immediate-release dose. On the other hand, the ascending-release regimen demonstrated comparable clinical efficacy to the immediate-release regimen during these evaluation periods. Thus, the ascending-release regimen avoided the decrease in therapeutic efficacy seen with the constant-release regimen at later time periods during the prolonged therapy period.

While not making any assertions with respect to mechanism(s) of action of the present invention, it is noted that the development of acute tolerance to methylphenidate has been proposed as an explanation for the unsatisfactory decrease in therapeutic effectiveness that has been observed in some cases. Support for this theory was demonstrated in a second clinical study wherein a decrease in effectiveness of methylphenidate was seen over a prolonged therapy period both when a constant-release regimen was utilized as well as when very closely-spaced doses of immediate-release methylphenidate dosage forms were administered. An ascending-release regimen, however, was shown to maintain therapeutic efficacy throughout the prolonged therapy period.

With the discovery that drug effectiveness over a prolonged therapy period may be improved in some circumstances with administration of drug in an ascending release rate over an extended period, a need arises for sustained-release oral dosage forms adapted to provide such a release rate. In one aspect of the present invention, it has been surprisingly discovered that bi-layer oral osmotic dosage forms can be adapted to meet this need. In another aspect, it has been surprisingly discovered that sustained-release oral osmotic dosage forms having novel tri-layer cores can be produced that also achieve sustained release of drug formulations at an ascending rate for an extended time period.

As is known in the prior art, osmotic dosage forms comprising compressed tablet cores require a short time period following administration in which to become hydrated sufficiently to begin releasing drug. For some drug therapies, the slight delay in initial drug release is unsatisfactory. This problem is overcome with the addition of an initial dose of drug supplied in an immediate-release overcoat applied to the surface of the semipermeable membrane. In preferred embodiments of the present invention, as disclosed herein, such an immediate-release drug overcoat is applied onto the surface of the bi-layer or tri-layer osmotic dosage forms.

For purposes of this disclosure, the following definitions shall apply:

For clarity and convenience herein, the convention is utilized of designating the time of drug administration as zero hours (t=0 hours) and times following administration in appropriate time units, e.g., t=30 minutes or t=2 hours, etc.

As used herein, the term "drug" generally refers to a pharmacologically active substance that, when delivered into a living organism, produces a desired, usually beneficial, effect. Drug compositions are generally utilized clinically in the form of a pharmaceutically acceptable salt thereof. In addition, some drug compositions exhibit chirality and, thus, have more than one optical isomer. Because the different optical isomers may exhibit different pharmacological effects, it may be advantageous to utilize a substantially pure form of one optical isomer of a drug, or a pharmaceutically acceptable salt thereof. Accordingly, the term "drug" refers to a clinically useful form of a drug composition including a pharmaceutically acceptable salt thereof and including a substantially pure isomer of the drug composition and a pharmaceutically acceptable salt thereof. Although a limited number of drugs are represented in the exemplary embodiments herein, the invention is not to be limited by the exemplary embodiments but is fully applicable to other suitable drugs as would be understood by persons of skill in the art.

The amount of drug incorporated in the dosage forms of the present invention varies depending on the particular drug, the therapeutic indication and the desired administration period, e.g., every 12 hours, every 24 hours, etc. Depending on the dose of drug desired to be administered, one or more of the dosage forms may be administered.

A drug "release rate" refers to the quantity of drug released from a dosage form per unit time, e.g., milligrams of drug released per hour (mg/hr). Drug release rates are calculated under in vitro dosage form dissolution testing conditions known in the art. As used herein, a drug release rate obtained at a specified time "following administration" refers to the in vitro drug release rate obtained at the specified time following implementation of an appropriate dissolution test. The dissolution test utilized in the Examples described herein were performed on dosage forms placed in metal coil sample holders attached to a USP Type VII bath indexer and immersed in about 50 ml of acidified water (pH=3) equilibrated in a constant temperature water bath at 37° C. Aliquots of the release rate solutions were injected into a chromatographic system to quantify the amounts of drug released during the testing intervals.

A commonly-used reference measurement for evaluating drug release from oral dosage forms is the time at which 90% of drug within a dosage form has been released. This measurement is referred to as the "$T_{90}$" for the dosage form.

An "immediate-release" dose of a drug refers to a dose that is substantially completely released within a time period of about 1 hour or less and, preferably, about 30 minutes or less. An immediate-release dose of drug applied as a coating on the surface of a dosage form, as used herein, refers to a dose of a drug prepared in a suitable pharmaceutically acceptable carrier to form a coating solution that will dissolve rapidly upon administration to thereby provide an immediate-release dose of drug. As is known in the art, such immediate-release drug overcoats may contain the same or a different drug or drugs as is contained within the underlying dosage form.

A "periodic release rate" refers to the quantity of drug released from a dosage form during a specified periodic interval as determined at the end of that specified periodic interval, i.e., at each periodic interval when a determination is made, the quantity of drug released represents the periodic release rate during that periodic interval. For example, the quantity of drug released as determined at t=1 h represents the periodic release rate from the dosage form during the first hour following administration and the quantity of drug released as determined at t=2 h represents the periodic release rate during the second hour following administration, etc.

An "ascending release rate" refers to a periodic release rate that is increased over the immediately-preceding periodic release rate, where the periodic intervals are the same. For example, when the quantity of drug released from a dosage form is measured at hourly intervals and the quantity of drug released during the fifth hour following administration (determined at t=5 hours) is greater than the quantity of drug released from the dosage form during the fourth hour following administration (determined at t=4 hours), an ascending release rate from the fourth hour to the fifth hour has occurred.

It will be appreciated that the first periodic release rate measured, e.g., the periodic release rate at t=1 hour (unless equal to 0), will always be greater than the release rate during the preceding period, e.g., the hour before the dosage form was administered, and, thus, the first periodic release rate always constitutes an occurrence of an ascending release rate.

The ascending release rates described herein refer to the release rate from a dosage form adapted to provide sustained release of drug and do not include release of drug from any immediate-release drug coating that may be applied to the dosage form. In dosage form embodiments additionally comprising an immediate-release dose of a drug applied as a coating onto the underlying dosage form, the drug release measured at t=1 hour will generally reflect both the drug released from the immediate-release drug coating and any drug released from the underlying dosage form, however, the quantity of drug released from the drug overcoat is disregarded in determining whether the drug release rate at t=2 hours is greater than the drug release at t=1 hour.

As used herein with reference to the time period during which an ascending release rate is provided, "an extended time period" refers to a time period beginning at t=0 hours and continuing through at least the mid-point, and preferably beyond the mid-point, of the relevant $T_{90}$ of the dosage form. Because the dosage forms of the present invention are intended to provide sustained release of drug, a suitable $T_{90}$ for purposes of this invention is at least about 6 hours and, consequently, the "extended time period" during which an ascending release rate is provided is at least 3 hours.

In accord with the above-recited definitions, an "ascending release rate over an extended time period" refers to ascending release rates of drug obtained from the time of administration of the dosage form through, and preferably beyond, the mid-point of the relevant $T_{90}$ for the dosage form. To illustrate, consider a situation where a dosage form has a $T_{90}$ of about 8 hours. In this situation, an "ascending release rate over an extended time period" is achieved when the release rate at each hour through t=4 hours is greater than the release rate in the immediately-preceding hour. Preferably, the release rate continues to ascend during time periods beyond t=4 hours.

Bi-layer oral osmotic dosage forms and methods of making and using such dosage forms are known in the art, for example, as described and claimed in the following US patents, owned by Alza Corporation: U.S. Pat. Nos. 4,327,725; 4,612,008; 4,783,337; and 5,082,668, each of which is incorporated in its entirety by reference herein. The prior art bi-layer osmotic dosage forms achieve sustained release of drug formulations wherein a relatively brief initial period of ascending release rates is followed by substantially constant release rates over a major portion of the $T_{90}$ period. The achievement of an ascending release rate for an extended time period of at least 50% of the $T_{90}$ period is not found within the prior art. The dosage forms of the present invention are useful for providing continuous effective drug therapy over a prolonged therapy period without exhibiting a decrease in effectiveness during the latter portion of the prolonged therapy period.

The bi-layer oral osmotic dosage forms of the present invention include a first component layer, comprising a selected drug and excipients for forming a deliverable drug composition when hydrated, and a second push layer, comprising a fluid-expandable osmopolymer and excipients, wherein the two layers are compressed into bi-layer tablet cores before the semipermeable membrane is applied and a suitable orifice for drug release therethrough is formed. The combination of features including the osmotic properties of the component layers, the fluid flux properties of the semipermeable membrane and the configuration of the tablet core ensures that drug is released at an ascending rate over an extended time period.

Importantly, the bi-layer tablet cores of the present invention are configured such that each component layer is substantially round in cross-dimension with a circumferential width and a length between a top and a bottom end. The two layers are compressed together longitudinally such that the resulting bi-layer tablet core has the same circumferential width as the component layers and a length that combines the lengths of the component layers. The overall configuration can be described as "capsule-shaped" wherein the bi-layer tablet core has a circumferential width that is less than its length and has a rounded "narrow" top end and a rounded "narrow" bottom end and wherein each narrow end comprises a different component tablet layer.

For purposes of this disclosure, the above-described tablet cores are referred to as longitudinally compressed tablet ("LCT") cores. This LCT configuration ensures that, as the push layer expands longitudinally within the compartment formed by the semipermeable membrane, the surface area of the push layer in contact with the semipermeable membrane is increased more than when other configurations are used.

In a preferred embodiment, sufficient activity in the push layer is achieved by use of a relatively large concentration (at least about 35%) of osmotically effective solute, or osmagent, such as sodium chloride. Consequently, the size of the push layer is relatively large and may be slightly larger than the first component layer containing the drug and excipients. In addition, for certain embodiments, sorbitol was found to be a useful excipient in the first component layer. It has been surprisingly discovered that the combination of features described above, including the LCT core configuration, the relatively high percent of osmagent and, in some exemplary embodiments, the use of sorbitol as an excipient provides the desired ascending release rate over an extended time period from bi-layer oral osmotic dosage forms. Exemplary embodiments of such bi-layer osmotic dosage forms are detailed below in Examples 1-3.

An embodiment of a bi-layer oral osmotic dosage form 15 is shown in cross-section in FIG. 1. The components are not drawn to scale. The bi-layer LCT core comprises a first component layer 21, containing drug and selected excipients, and a second push layer 29, containing at least one fluid-expandable osmopolymer and optionally containing at least one osmagent along with selected excipients. Suitable excipients are known in the art and include diluents, carriers, binders, fillers and processing aids. A semipermeable membrane 57 surrounds the bi-layer tablet core to form a compartment and a suitably sized orifice 55 is formed through the semipermeable membrane and into the first component layer 21 to permit drug formulation to be released from within the compartment. As illustrated, the orifice 55 is preferably formed in the narrow end of the dosage form comprising the first component layer. In operation, through cooperation of the bi-layer osmotic dosage form components, drug is released from the first drug-containing layer at an ascending release rate for an extended time period. Although not shown in FIG. 1, an immediate-release dose of a drug may be provided by applying a drug-containing overcoat to a bi-layer dosage form, if desired, as described elsewhere herein.

In addition to the above-described bi-layer osmotic dosage forms, it has been surprisingly discovered that oral osmotic dosage forms exhibiting an ascending drug release rate for an extended time period can also be achieved with a novel tri-layer tablet core surrounded by a semipermeable membrane and having suitable exit means for releasing drug formulation through the semipermeable membrane. The novel tri-layer tablet core has a first drug-containing layer, a second drug-containing layer and a third push layer. In operation, through the cooperation of the dosage form components, drug is successively released, in a sustained and controlled manner, from the first drug-containing layer and then from the second drug-containing layer such that an ascending release rate over an extended time period is achieved.

It has been discovered that a drug concentration gradient between the first and second drug-containing layers of the tri-layer core facilitates the achievement of an ascending drug release rate for an extended time period from the tri-layer osmotic dosage form. Consequently, the other excipients in the drug-containing layers may be more flexibly varied and adjusted for other purposes such as manufacturing convenience and pharmaceutical elegance. For example, the tri-layer osmotic dosage forms preferably avoid the use of sorbitol as an excipient. This provides manufacturing efficiency and product shelf-life advantages since sorbitol is very hygroscopic and attracts moisture during storage which can pose difficulties in handling and manufacturing as well as longer-term stability concerns. In addition, sufficient activity in the push layer may be achieved with the use of a relatively lower concentration (less than about 25%) of osmotically effective solute such that the size of the push layer can be smaller relative to the size of the two drug-containing layers. Preferably, the push layer is smaller than the combined size of the first and second drug-containing layers. An advantage to a smaller-sized push layer is that larger doses of drug, if desired, can be accommodated without the overall size of the dosage form becoming so large as to engender manufacturing challenges and/or to become unpalatable to patients.

In a presently preferred embodiment, the hydration rate of the tri-layer osmotic dosage form is improved with the inclusion of a flux-enhancing agent in the semipermeable membrane. In addition, it is preferred to use the longitudinally compressed tablet ("LCT") core configuration, as described above, for the tri-layer osmotic dosage forms to also enhance hydration. In a presently preferred embodiment, the combination of features including the LCT tri-layer core configuration, a suitable drug concentration gradient between the first and second component layers, the osmotic properties of the component layers and the fluid flux properties of the semipermeable membrane achieves the desired ascending rate of drug release over an extended time period. Advantageously, such preferred embodiments exhibit consistent and reliable operation and can be efficiently manufactured on a large-scale basis.

Figure 2:
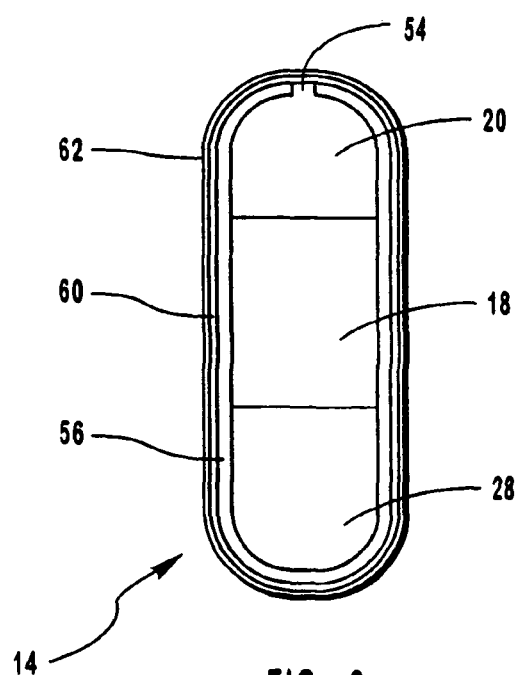
FIG. 2 is a cross-section view of a tri-layer osmotic dosage form, additionally comprising an immediate-release drug overcoat and an aesthetic overcoat, in accord with the present invention.

A preferred embodiment of a tri-layer oral osmotic dosage form additionally comprising an immediate-release dose of drug applied as an overcoat and an aesthetic overcoat 14 is shown in cross-section in FIG. 2. The tri-layer LCT core comprises a first component layer 20, containing a selected drug in a pharmaceutically acceptable form along with selected excipients; a second component layer 18, containing a higher concentration of drug along with selected excipients; and a third push layer 28, containing at least one osmopolymer and optionally containing at least one osmagent along with selected excipients. A semipermeable membrane 56 surrounds the tri-layer tablet core to form a compartment and a suitably sized orifice 54 is formed through the semipermeable membrane and into the first component layer to permit drug formulation to be released from within the compartment. As illustrated, the orifice 54 is preferably formed in the narrow end of the dosage form comprising the first component layer. In operation, through cooperation of the tri-layer osmotic dosage form components, drug is successively released, in a sustained and controlled manner, from the first drug-containing layer and then from the second drug-containing layer at an ascending release rate for an extended time period.

As shown in FIG. 2, the preferred embodiment further comprises an immediate-release dose of drug contained within an overcoat 60 applied onto the surface of the tri-layer osmotic dosage form. The drug is mixed with suitable excipients such as, for example, hydroxypropylmethylcellulose, to prepare a solution for coating onto the surface of the semi-permeable membrane of the tri-layer osmotic dosage form that will rapidly dissolve and release drug following administration.

As shown in FIG. 2, it is also preferred to provide an optional aesthetic overcoat 62 applied onto the surface of the drug-containing overcoat 60. As known in the art, such aesthetic overcoats provide advantages including taste-masking, improved appearance and "glidability" for facilitating swallowing and further processing steps such as printing, packaging, etc. Exemplary embodiments of tri-layer osmotic dosage forms that exhibit a substantially ascending release rate over an extended time period are detailed below in Examples 4-6 and Examples 8 and 9.

The continued maintenance of therapeutic effectiveness over a prolonged therapy period by the administration of the oral osmotic dosage forms that exhibit an ascending release rate over an extended time period of the present invention has been demonstrated. An exemplification is described below in Example 7. In particular, it has been discovered that such osmotic dosage forms containing methylphenidate can be used to provide effective once-a-day therapy for ADHD. This discovery represents an important improvement in drug therapy for ADHD by eliminating the need for multiple daily doses of methylphenidate yet providing therapeutic efficacy throughout the day that compares to the therapeutic efficacy provided by multiple doses of immediate release methylphenidate.

The following examples are illustrative of the present invention, and the exampled should not be considered as limiting the scope of the invention in any way, as these examples, and other equivalents thereof, will become apparent to those versed in the art in the light of the present disclosure and the accompanying claims.

Example 1

Bi-layer oral osmotic dosage forms were made in accord with conventional manufacturing processes known in the art and disclosed in detail in copending U.S. application Ser. No. 967,606, filed Nov. 10, 1997, of which the present application is a continuation-in-part application. Briefly, a first component layer, containing methylphenidate hydrochloride and selected excipients, and a second push layer, containing suitable osmopolymers, 40% by weight of an osmagent and selected excipients, were separately prepared by granulation methods. Next, the first component layer and the second push layer granulation preparations were longitudinally compressed together to form bi-layer LCT cores. A selected semipermeable membrane was then coated around the bi-layer LCT cores and a suitable 30 mil orifice for drug release was formed therethrough and into the first component layer.

Each dosage form as prepared comprised:

| First component layer | |
|---|---|
| 14.08 mg | methylphenidate hydrochloride |
| 90.26 mg | poly(ethylene)oxide (200,000 number-average molecular weight) |
| 5.5 mg | poly(vinylpyrrolidone) (40,000 number-average molecular weight) |
| 0.11 mg | magnesium stearate |
| 0.555 mg | butylated hydroxy toluene |

| Second push layer | |
|---|---|
| 71.032 mg | poly(ethylene)oxide (7,000,000 number-average molecular weight) |
| 52.8 mg | sodium chloride |
| 6.6 mg | poly(vinylpyrrolidone) (40,000 number-average molecular weight) |
| 1.32 mg | red ferric oxide |
| 0.132 mg | magnesium stearate |
| 0.555 mg | butylated hydroxy toluene |

| Semipermeable Membrane | |
|---|---|
| 15.3 mg | cellulose acetate (39.8% acetyl content) |
| 1.7 mg | poly(ethylene glycol) (3350 number-average molecular weight) |

The periodic release rates from the dosage form were determined hourly for ten hours using in vitro dissolution testing. A residual quantity of drug of 0.72 mg remained in the dosage form. The results are shown in Table 1 along with an indication of whether an ascending release rate occurred.

TABLE 1

| Time (hours) | Quantity of drug released (mg) | Ascending Release Rate Occurrence |
|---|---|---|
| 1 | 0.22 | YES |
| 2 | 1.45 | YES |
| 3 | 1.72 | YES |
| 4 | 1.84 | YES |
| 5 | 2.05 | YES |
| 6 | 2.21 | YES |
| 7 | 2.13 | NO |
| 8 | 1.26 | NO |
| 9 | 0.39 | NO |
| 10 | 0.09 | NO |

As seen from Table 1, drug was released from the dosage forms at an ascending rate for an extended time period, i.e., more than 90% of the drug was released by t=8 hours and ascending release rates occurred through t=6 hours, an extended period of time well beyond the mid-point of the $T_{90}$.

Example 2

Bi-layer oral osmotic dosage forms were made in accord with conventional manufacturing processes known in the art and disclosed in detail in copending U.S. application Ser. No. 967,606, filed Nov. 10, 1997, of which the present application is a continuation-in-part application. Briefly, a first component layer, containing methylphenidate hydrochloride, sorbitol and selected excipients, and a second push layer, containing suitable osmopolymers, 40% by weight of an osmagent and selected excipients, were separately prepared by granulation methods. Next, the first component layer and the second push layer granulation preparations were longitudinally compressed together to form bi-layer LCT cores. A selected semipermeable membrane was then coated around the bi-layer LCT cores and a suitable 30 mil orifice for drug release was formed therethrough.

Each dosage form as prepared comprised:

| First component layer (110 mg) | |
|---|---|
| 12.8% | methylphenidate hydrochloride |
| 54.75% | poly(ethylene)oxide (200,000 number-average molecular weight) |
| 25.4% | sorbitol |
| 5% | hydroxypropylmethylcellulose (11,200 number-average molecular weight) |
| 2% | magnesium stearate |
| 0.05% | butylated hydroxy toluene |

| Second push layer (132 mg) | |
|---|---|
| 53.85% | poly(ethylene)oxide (7,000,000 number-average molecular weight) |
| 40% | sodium chloride |
| 5% | hydroxypropylmethylcellulose (11,200 number-average molecular weight) |
| 1% | red ferric oxide |
| 0.1% | magnesium stearate |
| 0.05% | butylated hydroxy toluene |

| Semipermeable Membrane (42 mg) | |
|---|---|
| 47.5% | cellulose acetate (39.8% acetyl content) |
| 47.5% | cellulose acetate (32% acetyl content) |
| 5% | poly(ethylene glycol) (3350 number-average molecular weight |

The periodic release rates from the dosage form were determined hourly for twelve hours. No residual quantity of drug remained in the dosage form. The results are shown in Table 2 along with an indication of the occurrences of an ascending release rate.

TABLE 2

| Time (hours) | Quantity of drug released (mg) | Ascending Release Rate Occurrence |
|---|---|---|
| 1 | 0.13 | YES |
| 2 | 1.16 | YES |
| 3 | 1.53 | YES |
| 4 | 1.61 | YES |
| 5 | 1.75 | YES |
| 6 | 1.79 | YES |
| 7 | 2.13 | YES |
| 8 | 2.18 | YES |
| 9 | 1.07 | NO |
| 10 | 0.43 | NO |
| 11 | 0.17 | NO |
| 12 | 0.13 | NO |

As seen from Table 2, more than 90% of the drug was released by t=9 hours and ascending release rates occurred through t=8 hours, an extended time period well beyond the mid-point of the T.

Example 3

Bi-layer oral osmotic dosage forms additionally comprising an immediate-release dose of drug applied as an overcoat onto the semipermeable membrane were made in accord with conventional manufacturing processes known in the art and disclosed in detail in copending U.S. application Ser. No. 967,606, filed Nov. 10, 1997, of which the present application is a continuation-in-part application. Briefly, a first component layer, containing methylphenidate hydrochloride, sorbitol and selected excipients, and a second push layer, containing suitable osmopolymers, 39.8% by weight of an osmagent and selected excipients, were separately prepared by granulation methods. Next, the first component layer and the second push layer granulation preparations were longitudinally compressed together to form bi-layer LCT cores. A selected semipermeable membrane was then coated around the bi-layer LCT cores and a suitable 30 mil orifice for drug release was formed therethrough. A drug-containing overcoat mixture was prepared and coated onto the semipermeable membrane of the osmotic dosage form. Optionally, a taste-masking overcoat is also applied.

Each osmotic bi-layer dosage form as prepared comprised:

| First component layer | |
|---|---|
| 14 mg | methylphenidate hydrochloride |
| 61 mg | poly(ethylene)oxide (2,000,000 number-average molecular weight) |
| 27.5 mg | sorbitol |
| 5.5 mg | polyvinylpyrrolidone |
| 2.2 mg | magnesium stearate |
| 0.055 mg | butylated hydroxy toluene |

| Second push layer | |
|---|---|
| 72 mg | poly(ethylene)oxide (7,000,000 number-average molecular weight) |
| 53 mg | sodium chloride |
| 6.6 mg | polyvinylpyrrolidone |
| 1.3 mg | red ferric oxide |
| 0.132 mg | magnesium stearate |
| 0.066 mg | butylated hydroxy toluene |

| Semipermeable Membrane | |
|---|---|
| 20 mg | cellulose acetate (39.8% acetyl content) |
| 20 mg | cellulose acetate (32% acetyl content) |
| 2 mg | poly(ethylene glycol) (4000 number-average molecular weight) |

An immediate-release drug-containing overcoat comprising 60% hydroxypropylmethylcellulose and 40% methylphenidate hydrochloride is prepared and a final solution of 10 mg (i.e., containing 4 mg of methylphenidate salt) is coated onto the semipermeable membrane of the osmotic dosage form.

The periodic release rates from the drug overcoat and the osmotic dosage form were determined at 30 minutes, 1 hour and then hourly for the next nine hours. The 4 mg of methylphenidate contained within the drug overcoat was released within the first 30 minutes and the periodic release rate shown at t=1 hour of 0.41 mg constitutes drug released from the bi-layer osmotic dosage form during the second 30-minute interval. No residual quantity of drug remained in the dosage form. The hourly results are shown in Table 3 along with an indication of the occurrences of an ascending release rate.

TABLE 3

| Time (hours) | Quantity of drug released (mg) | Ascending Release Rate Occurrence |
|---|---|---|
| 1 | 0.41 | YES |
| 2 | 1.05 | YES |
| 3 | 1.49 | YES |
| 4 | 1.57 | YES |
| 5 | 1.71 | YES |
| 6 | 1.75 | YES |
| 7 | 2.09 | YES |
| 8 | 2.14 | YES |
| 9 | 1.32 | NO |
| 10 | 0.48 | NO |

As seen from Table 3, exclusive of the immediate-release drug overcoat, more than 90% of the drug was released by t=9 hours and ascending release rates occurred through t=8 hours, an extended period of time well beyond the mid-point of the $T_{90}$.

Example 4

Tri-layer oral osmotic dosage forms were made in accord with conventional manufacturing processes known in the art and disclosed in detail in copending U.S. application Ser. No. 937,336, filed Aug. 19, 1997, of which the present application is a continuation-in-part application. Briefly, a first component layer, containing pseudoephedrine hydrochloride and selected excipients, a second component layer, containing a higher concentration of pseudoephedrine hydrochloride and selected excipients, and a third push layer, containing suitable osmopolymers, an osmagent and selected excipients, were separately prepared by granulation methods. Next, the first component layer, second component layer and the third push layer granulation preparations were longitudinally compressed together to form tri-layer LCT cores. A selected semipermeable membrane was then coated around the tri-layer LCT cores and a suitable 30 mil orifice for drug release was formed therethrough.

Each dosage form as prepared comprised:

| First component layer | |
|---|---|
| 4.4 mg | pseudoephedrine hydrochloride |
| 15.3 mg | poly(ethylene)oxide (300,000 number-average molecular weight) |
| 1.1 mg | hydroxypropylmethylcellulose (9,200 number-average molecular weight) |
| 1.1 mg | polyoxyethylene 40 stearate |
| 0.11 mg | magnesium stearate |

| Second component layer | |
|---|---|
| 13.5 mg | pseudoephedrine hydrochloride |
| 2.59 mg | poly(ethylene)oxide (300,000 number-average molecular weight) |
| 0.9 mg | hydroxypropylmethylcellulose (9,200 number-average molecular weight) |
| 0.9 mg | polyoxyethylene 40 stearate |
| 0.018 mg | red ferric oxide |
| 0.09 mg | magnesium stearate |

| Third push layer | |
|---|---|
| 22.2 mg | poly(ethylene)oxide (7,000,000 number-average molecular weight) |
| 12 mg | sodium chloride |
| 2 mg | hydroxypropylmethylcellulose (9,200 number-average molecular weight) |
| 2 mg | polyoxyethylene 40 stearate |
| 1.2 mg | cross-linked acrylic acid polymer |
| 0.4 mg | red ferric oxide |
| 0.2 mg | magnesium stearate |

| Semipermeable Membrane | |
|---|---|
| 11.4 mg | cellulose acetate (39.8% acetyl content) |
| 0.6 mg | polyethylene glycol (3350 average number molecular weight) |

The periodic release rates from the osmotic dosage form were determined hourly for 7 hours and results are shown in Table 4 along with an indication of the occurrences of an ascending release rate.

TABLE 4

| Time (hours) | Quantity of drug released (mg) | Ascending Release Rate Occurrence |
|---|---|---|
| 1 | 0.13 | YES |
| 2 | 0.65 | YES |
| 3 | 2.2 | YES |
| 4 | 2.78 | YES |
| 5 | 3.24 | YES |
| 6 | 3.14 | YES |
| 7 | 3.43 | YES |

As seen from Table 4, about 87% of drug was released during the first 7 hours and ascending release rates were achieved throughout this period.

Example 5

Tri-layer oral osmotic dosage forms having a drug concentration gradient wherein the drug concentration was greater in the second component layer than the first component layer and also having viscosity gradients wherein the viscosity of the first component layer was less than the viscosity of the second component layer and the viscosity of the second component layer was lower than the viscosity of the third push layer were made in accord with conventional manufacturing processes known in the art and disclosed in detail in copending U.S. application Ser. No. 937,336, filed Aug. 19, 1997, of which the present application is a continuation-in-part application.

Each dosage form as prepared comprised:

| First component layer (350 mg) | |
|---|---|
| 8.6% | nicardipine |
| 54.8% | sorbitol |
| 36.8% | poly(ethylene)oxide (200,000 number-average molecular weight) |

| Second component layer (120 mg) | |
| --- | --- |
| 45% | nicardipine |
| 50% | poly(ethylene)oxide (300,000 number-average molecular weight) |
| 5% | hydroxypropylmethylcellulose (9,200 number-average molecular weight) |

| Third push layer (350 mg) | |
| --- | --- |
| 68.75% | poly(ethylene)oxide (7,000,000 number-average molecular weight) |
| 20% | sodium chloride |
| 5% | hydroxypropylmethylcellulose (9,200 number-average molecular weight) |
| 5% | cross-linked acrylic acid polymer |
| 1% | ferric oxide |
| 0.25% | magnesium stearate |

| Semipermeable Membrane (43.5 mg) | |
| --- | --- |
| 95% | cellulose acetate (39.8% acetyl content) |
| 5% | polyethylene glycol (3350 average number molecular weight) |

The dosage forms had 25 mil exit orifices formed through the semipermeable membrane to permit release of drug formulation from within the compartment. An ascending release rate for an extended time period of about 16 hours was achieved with the dosage forms of Example 5.

Example 6

Preferred embodiments of the tri-layer osmotic dosage forms of the present invention additionally comprising an immediate-release dose of drug applied as an overcoat, as shown in FIG. 2, were prepared in accord with conventional osmotic tablet manufacturing processes.

The first component layer contained the following (by weight percent): 9.40% methylphenidate hydrochloride, 83.71% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.34% succinic acid; 0.5% stearic acid; and 0.05% butylated hydroxy toluene.

The second component layer contained the following (by weight percent): 13.65% methylphenidate hydrochloride, 78.80% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.95% succinic acid; 0.5% stearic acid; 0.05% butylated hydroxy toluene; and 0.05% yellow ferric oxide, as coloring agent.

The third push layer contained the following (by weight percent): 73.7% high molecular weight polyethylene oxide (Polyox 303 brand product of Union Carbide, Danbury, Conn.), 20% sodium chloride; 5% polyvinylpyrrolidone (Kolidon 29-32 brand product of BASF Corp., Mt. Olive, N.J.); 0.25% stearic acid; 0.05% butylated hydroxy toluene; and 1% green ferric oxide, as coloring agent.

Each of the first component layer, second component layer and third push layer were separately prepared into granulated compositions in a fluid bed granulator. The granulated compositions were then compressed sequentially and longitudinally on a rotary tablet press to produce the tri-layer LCT cores. For each dosage form, 40 mg of the first component layer granulation and 75 mg of the second component layer granulation were first sequentially filled and tamped at 100 newtons into the die. Then, 90 mg of the third push layer granulation was added to the die and the final compression was performed at 1500 newtons.

The composition of the semipermeable membrane was 83% by weight cellulose acetate (CA 398-10, having an acetyl content of 39.8%, product of Eastman Chemical, Kingsport, Tenn.) and 17% by weight copolymer of ethylene and propylene oxide (Poloxamer 188 brand product of BASF Corp., Mt. Olive, N.J., added as a flux-enhancer. The two ingredients were dissolved in a blend of 99.5% acetone and 0.5% water to form a 5% solids solution. In a pan coater, the solution was then sprayed onto the tri-layer LCT cores to a weight of 25.7 mg and a thickness of 4-5 mil.

After the semipermeable membrane had been applied to form a compartment containing the tri-layer LCT cores, a 0.76 mm (40 mil) orifice was drilled through the semipermeable membrane at the narrow end of the compartment proximate to the first component layer to thereby form the preferred tri-layer osmotic dosage forms, each containing 14 mg of methylphenidate. Each dosage form was approximately 12 mm long with an approximate diameter of 5.3 mm.

The drug overcoat for providing an immediate-release initial dose of drug contains approximately 30% by weight methylphenidate hydrochloride, approximately 70% by weight hydroxypropylmethylcellulose (Methocel E3 brand name product of Dow Chemical Co., Midland, Mich.), and a trace amount of phosphoric acid (i.e., 20 ml of phosphoric acid added to 87 kg of drug in solution). An aqueous coating solution is prepared by dissolving and mixing the ingredients in water to form a solution with a 10% solids composition. In a pan coater, the solution was then sprayed onto the semipermeable membranes of the tri-layer osmotic dosage forms to a weight of about 14.0 mg comprising an immediate-release dose of methylphenidate of about 4 mg.

The final aesthetic overcoat composition weighed 16.9 mg and contained an underlayer of Opadry II, yellow (brand name product of Colorcon, West Point, Pa. and an overlayer of Opadry, clear, with a trace amount of carnauba wax, a glidant, prepared and applied as follows: first, Opadry II (10%) is suspended in water (90%) and sprayed onto the drug-overcoated dosage forms; next, clear Opadry (5%) is suspended in water (95%) and sprayed onto the drug- and Opadry II-overcoated dosage forms; finally, the dosage forms are tumbled in the coater with the carnauba wax for ten minutes to allow about 100 ppm of wax to be uniformly distributed onto the clear Opadry overcoat.

Many pharmaceutical dosage forms utilize drug in salt form such as the hydrochloride salt of methylphenidate utilized herein. Such salt forms of drugs prepared in aqueous solution, however, are prone to degradation and, thus, often have stability and shelf-life problems. It has been discovered that the addition of an appropriate pH-adjusting agent to the aqueous solution decreases undesired degradation and improves the stability of the product. In particular, in preferred embodiments tri-layer osmotic dosage forms comprising methylphenidate hydrochloride, it has been discovered that degradation of the drug ingredient can be minimized by the addition of suitable antidegradation agents, i.e., succinic acid in the first and second component layers and phosphoric acid in the drug overcoat. Other suitable antidegradation agents include compounds that dissolve in an aqueous medium are pharmaceutically acceptable, i.e., nontoxic and suitable for oral administration to humans, and that exhibit sufficient pH-adjusting ability, i.e., have a pH no greater than 4 and preferably of 3 or below. Additional examples include potassium phosphate, sodium phosphate, fumaric acid, citric acid, tartaric acid, malic acid, hydrochloric acid, aspartic acid, glutamic acid, oxalic acid, lactic acid, malonic acid, glyceric acid and ascorbic acid.

Figure 3:
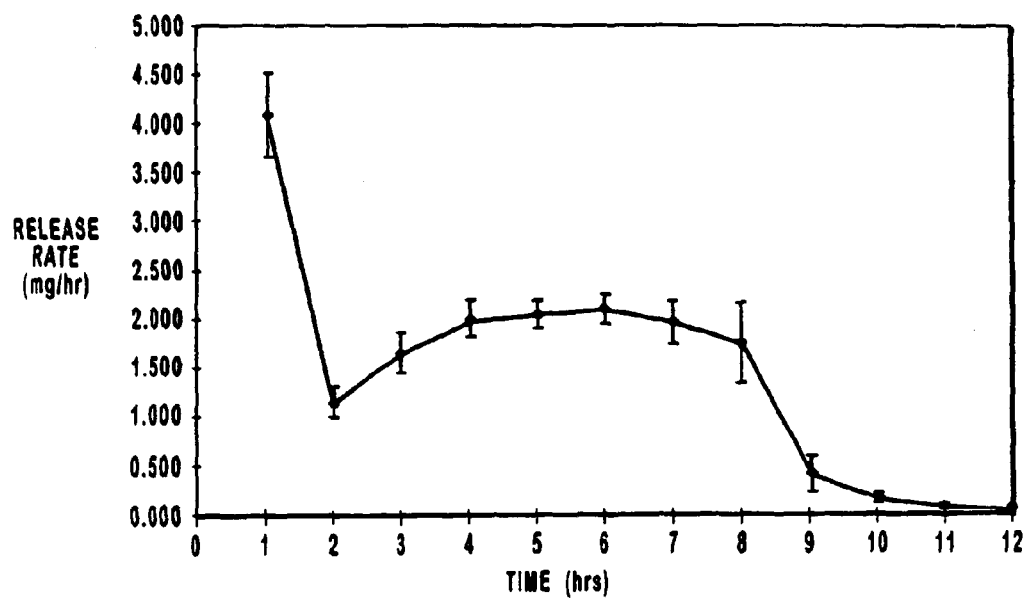
FIG. 3 is a graph illustrating the quantity of drug released over time from a preferred embodiment of the present invention as described in Example 6.

Periodic release rates for twenty-four sample dosage forms prepared as described were determined hourly for 12 hours and are presented in graph form in FIG. 3. The mean quantities released each hour are shown in Table 5 along with an indication of the occurrences of an ascending release rate. It is noted that the entire 4 mg immediate-release dose was essentially released within the first hour and this quantity is disregarded with respect to the determination that an ascending release rate occurred at t=2 hours, i.e., the mean quantity at t=2 hours was compared to the mean quantity at t=1 hours less 4 mg representing the immediate-release dose.

TABLE 5

| Time (hours) | Quantity of drug released (mg) | Ascending Release Rate Occurrence |
| --- | --- | --- |
| 1 | 4.098 | YES |
| 2 | 1.138 | YES |
| 3 | 1.650 | YES |
| 4 | 1.993 | YES |
| 5 | 2.043 | YES |
| 6 | 2.099 | YES |
| 7 | 1.966 | NO |
| 8 | 1.763 | NO |
| 9 | 0.428 | NO |
| 10 | 0.174 | NO |
| 11 | 0.084 | NO |
| 12 | 0.061 | NO |

As seen from Table 5, exclusive of the immediate-release drug overcoat, more than 90% of the drug was released by t=8 hours and ascending release rates occurred through t=6 hours, an extended period of time well beyond the mid-point of the $T_{90}$.

Example 7

Therapeutic effectiveness of single doses of tri-layer osmotic dosage forms containing 14 mg of methylphenidate and additionally comprising an immediate-release drug overcoat containing 4 mg of methylphenidate was studied and compared to multiple doses of immediate-release methylphenidate. Safety and therapeutic efficacy parameters were evaluated for a 12-hour period in the same subjects treated with the following regimens on different days: the experimental regimen wherein the tri-layer osmotic dosage form was administered once at t=0 hours and the standard regimen wherein immediate-release methylphenidate (Ritalin®) was administered three times, at t=0 hours, t=4 hours, and t=8 hours. Because the subjects were current methylphenidate users, the doses of methylphenidate administered during each regimen varied somewhat to match as closely as possible the "usual dose" each subject was routinely administered. For comparative purposes, the actual doses were normalized to a single 18 mg dose of the tri-layer osmotic dosage and to 15 mg of Ritalin® administered as three 5 mg doses.

Plasma drug concentrations were determined in all subjects at the same times during the study periods for each regimen. The selected times corresponded to the time just prior to, and 1.5 hours and 2.5 hours following, administration of the first two doses of immediate-release methylphenidate (i.e., at t=0 hours, t=1.5 hours, t=2.5 hours, t=4 hours, t=5.5 hours, t=6.5 hours), and just prior to, and 1.5 hours and 3.5 hours following, administration of the third dose (i.e., at t=8 hours, t=9.5 hours and t=11.5 hours).

Figure 4:
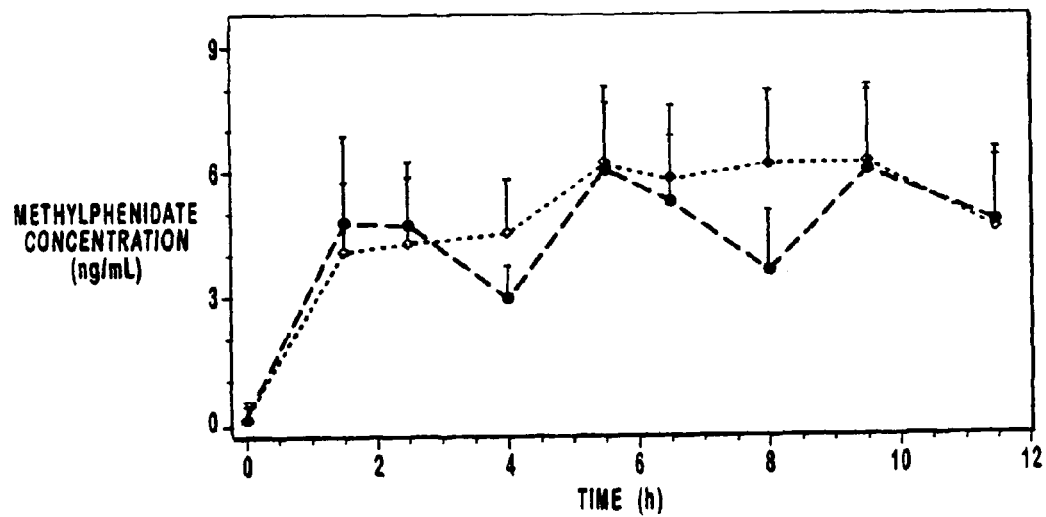
FIG. 4 is a graph illustrating the plasma drug concentration over time obtained following administration of methylphenidate in accord with an experimental regimen (open diamonds) and a standard regimen (closed circles) as described in Example 7.

In FIG. 4, plasma drug concentrations obtained from one group of study participants (n=16) while treated with the experimental regimen (represented by open diamonds) and while treated with the standard regimen (represented by closed circles) are shown in graph form. A comparison of FIGS. 3 and 4 demonstrates a correlation between the in vitro release rates through about t=8 hours and the in vivo plasma drug concentrations through about t=9.5 hours.

As shown in FIG. 4, the plasma drug concentration following each administration of an immediate-release dose rises relatively rapidly and then declines at a generally characteristic rate until the next dose is administered. The plasma drug concentration following administration of the tri-layer osmotic dosage form also exhibits an initial relatively rapid rise due largely to release of drug from the immediate-release drug overcoat. Subsequently, however, the plasma drug concentration does not decline but continues to substantially ascend (save for a slight "dip" between t=5.5 hours and t=6.5 hours) through a time period of 9.5 hours. Particularly striking is the difference during the time periods within about 1 hour before and about 1.5 hours following administration of the second and the third immediate-release dose. With the standard regimen, during these periods, the plasma drug concentration declines to a trough concentration and then rises again to a peak concentration. With the experimental regimen, during these same time periods, the plasma drug concentration is substantially smoothly ascending and exhibits no peaks and troughs.

Safety and therapeutic parameters, including behavioral, attentional and cognitive functions, were assessed hourly during the first three hours and the last three hours of the study period and at two-hour intervals in between. The clinical effectiveness of the experimental regimen was closely comparable to the clinical effectiveness of the standard regimen throughout the twelve-hour study period. An effective once-a-day therapy for ADHD provides many advantages and offers a significant improvement in drug therapy by eliminating the need for multiple daily doses of methylphenidate while providing continued therapeutic efficacy throughout the day.

Example 8

Tri-layer oral osmotic dosage forms were made in accord with the manufacturing processes of Example 6 but comprising twice as much methylphenidate, i.e., a total of 28 mg of methylphenidate contained within the first and second component layers and 8 mg of methylphenidate in the drug overcoat. All of the remaining ingredients are also doubled so that the weight percents are the same as in Example 6. The third push layer is also doubled. The semipermeable membrane had the same composition as in Example 6 but was applied to a weight of about 34 mg.

These dosage forms exhibit release of 36 mg of methylphenidate with about 8 mg released immediately and the remaining 28 mg released at an ascending release rate over an extended time period.

Example 9

Tri-layer oral osmotic dosage forms were made in accord with the manufacturing processes of Example 6 but comprising a total of 42 mg of methylphenidate contained within the first and second component layers and 12 mg of methylphenidate in the drug overcoat. The first component layer contained the following (by weight percent): 11.5% methylphenidate hydrochloride, 81.6% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.3% succinic acid; 0.5% stearic acid; 0.05% butylated hydroxy toluene; and 0.05% yellow ferric oxide, as coloring agent. The second component layer contained the following (by weight percent): 19.8% methylphenidate hydrochloride, 72.7% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.95% succinic acid; 0.5% stearic acid; and 0.05% butylated hydroxy toluene. The third push layer is doubled from Example 6 and the semipermeable membrane had the same composition as in Example 6 but was applied to a weight of about 34 mg.

These dosage forms exhibit release of 54 mg of methylphenidate with about 12 mg released immediately and the remaining 42 mg released at an ascending release rate over an extended time period.

While there has been described and pointed out features and advantages of the invention, as applied to present embodiments, those skilled in the art will appreciate that various modifications, changes, additions, and omissions in the descriptions within the specification can be made without departing from the spirit of the invention.

What is claimed:

1. A method for treating Attention-Deficit Hyperactivity Disorder in a subject comprising:
    administering to said subject an osmotic dosage form comprising
    a capsule-shaped longitudinally compressed tablet core containing a plurality of layers wherein drug is contained in at least one layer and at least one other layer comprises a suitable fluid-expandable polymer, wherein said drug comprises methylphenidate hydrochloride;
    a semipermeable wall that surrounds said longitudinally compressed tablet core to form a compartment that has an osmotic gradient that drives fluid from an external fluid environment contacting said semipermeable wall into said compartment; and
    an orifice that is formed through said semipermeable wall at a location adjacent to the first layer that permits drug to be released from the compartment into said external fluid environment,
    wherein the dosage form releases the drug over a period comprising a first, second, and third sequential time intervals of equal duration, and
    wherein the dosage form releases more of said drug during said second interval than during said first interval and more of said drug during said third interval than during said second interval.

2. The method according to claim 1 wherein said period of release comprises a fourth sequential time interval, and wherein the dosage form releases more of said drug during said fourth interval than during said third interval.

3. The method according to claim 1 further comprising an outer surface and an immediate-release dosage of the drug applied as a coating onto the outer surface.

4. The method according to claim 3 wherein the dosage form releases more of said drug during said second interval than during said first interval, not including drug released from said coating during said first interval.

5. The method according to claim 4 wherein each of said time intervals is 30 minutes.

6. The method according to claim 4 wherein each of said time intervals is 1 hour.

7. The method according to claim 5 wherein the drug released during said first interval does not include any drug released from said first layer of said dosage form.

8. The method according to claim 6 wherein the drug released during said first interval does not include any drug released from said first layer of said dosage form.

9. The method according to claim 1 wherein said dosage form is administered orally.

10. The method according to claim 1 wherein said dosage form is administered one time per day for multiple days.

11. The method according to claim 1 wherein said dosage form is administered to a non-adult subject.

12. The method according to claim 1 wherein said dosage form further comprises a third layer comprising an additional portion of said drug, wherein said third layer is disposed between said other drug containing layer and said fluid-expandable polymer layer.

* * * * *